United States Patent
Ehrlich

(10) Patent No.: US 12,377,074 B2
(45) Date of Patent: Aug. 5, 2025

(54) TREATMENT FOR WOLFRAM SYNDROME

(71) Applicant: YALE UNIVERSITY, New Haven, CT (US)

(72) Inventor: Barbara Ehrlich, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 800 days.

(21) Appl. No.: 17/610,041

(22) PCT Filed: May 26, 2020

(86) PCT No.: PCT/US2020/034539
§ 371 (c)(1),
(2) Date: Nov. 9, 2021

(87) PCT Pub. No.: WO2020/251748
PCT Pub. Date: Dec. 17, 2020

(65) Prior Publication Data
US 2022/0347159 A1 Nov. 3, 2022

Related U.S. Application Data

(60) Provisional application No. 62/860,033, filed on Jun. 11, 2019.

(51) Int. Cl.
*A61K 31/4162* (2006.01)
*A61P 3/10* (2006.01)
*A61P 7/12* (2006.01)
*A61P 27/00* (2006.01)

(52) U.S. Cl.
CPC ............ *A61K 31/4162* (2013.01); *A61P 3/10* (2018.01); *A61P 7/12* (2018.01); *A61P 27/00* (2018.01)

(58) Field of Classification Search
CPC .................................................. A61K 31/4162
See application file for complete search history.

(56) References Cited

PUBLICATIONS

Crouzier, Lucie et el.,Convolamine, a tropane alkaloid extracted from Convolvulus plauricalis, is a potent sigma-1 receptor-positive modulator with cognitive and neuroprotective properties., Phytotherapy Research published by John Wiley & Sons Ltd., 2024;38:694-712. USA.
CME Clinical Guidance, FDA grants rare pediatric disease status to ibudilast for Krabbe disease, Healio, Jan. 19, 2016, 1 Page.
Rui Hu et al., ISR inhibition reverses pancreatic B-cell failure in Wolfram syndrome models., www.nature.com/cdd, CCD Press, Feb. 6, 2024.
Crouzier, Lucie et el., Activation of the sigma-1 receptor chaperone alleviates symptoms of Wolfram syndrome in preclinical models., Sci Transl Med. Author manuscript; available in PMC Feb. 9, 2023. USA.
K. Batjargal et al., Effect of 4-phenylbutyrate and valproate on dominant mutations of WFS1 gene in Wolfram syndrome., Journal of Endocrinological Investigation, Mar. 26, 2020.

*Primary Examiner* — Paul V Ward
(74) *Attorney, Agent, or Firm* — Henry D. Coleman; R. Neil Sudol

(57) ABSTRACT

The present invention is directed to a novel treatment for Wolfram Syndrome or heterozygous wolframin, to methods of treatment in order to delay, inhibit, ameliorate and/or reduce the likelihood of symptomology of a patient with Wolfram Syndrome or heterozygous wolframin.

28 Claims, 40 Drawing Sheets

FIGURE 18 B

B    Deep Sequencing Results

| | Sample | Total | WT_g1 | #1-Indel | #1-Reads(%) | #2-Indel | #2-Reads(%) |
|---|---|---|---|---|---|---|---|
| WFS1 KO #1 | 1E11 | 1525 | 0 (0.0%) | 1 | 889 (58.3%) | 32 | 625 (41.0%) |
| WFS1 KO #2 | 4F1 | 2022 | 0 (0.0%) | -4 | 1012 (50.0%) | 1 | 1004 (49.7%) |
| WFS1 WT | 787 | 1605 | 1513 (94.3%) | 0 | 1578 (98.3%) | | |

FIGURE 1S C

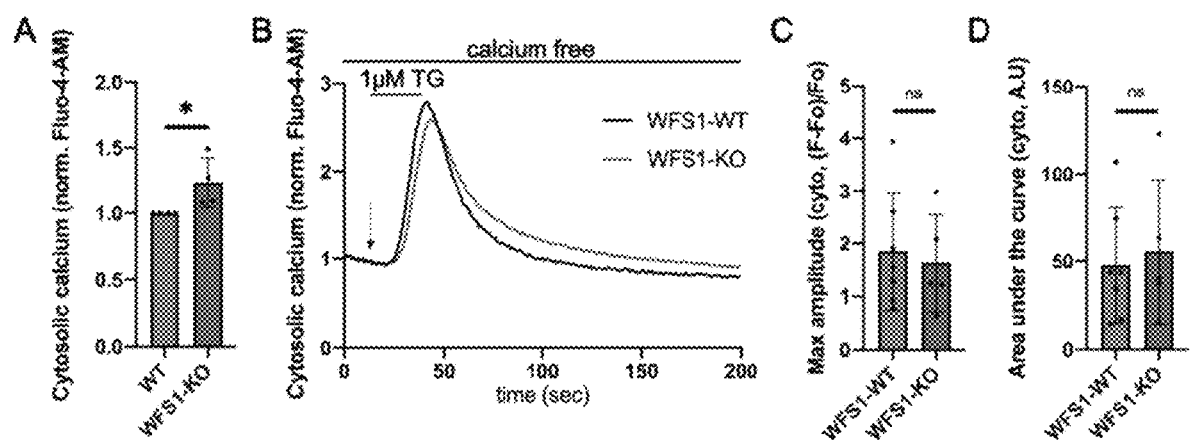
FIGURE 2S A, B, C, D

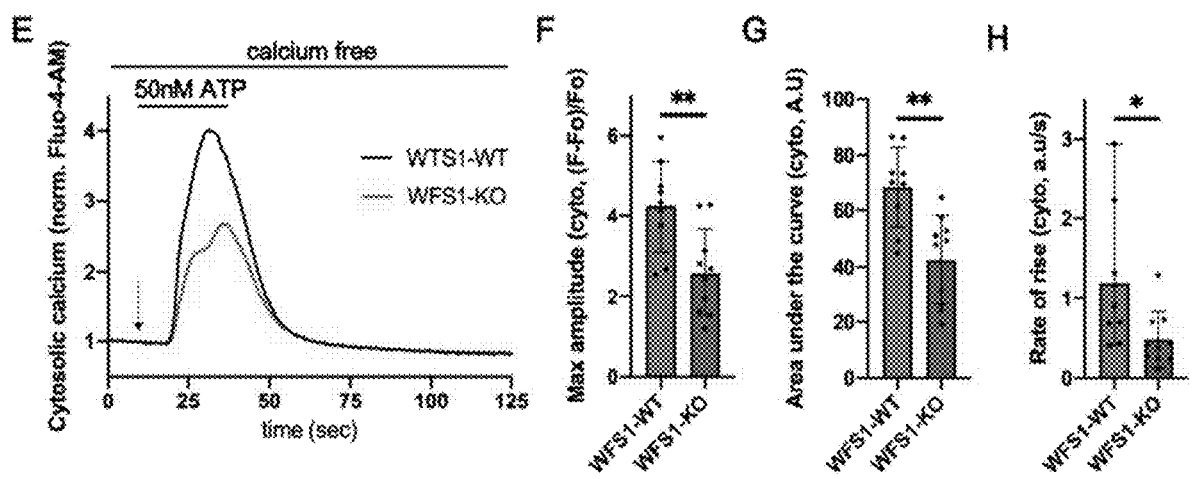
FIGURE 2S E, F, G, H

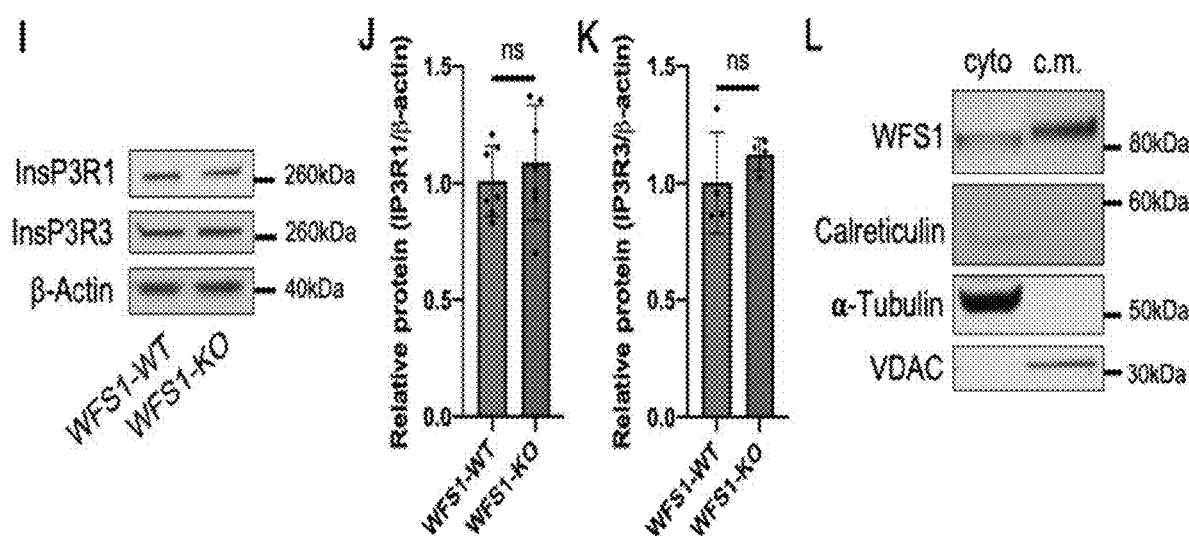
FIGURE 2S I, J, K, L

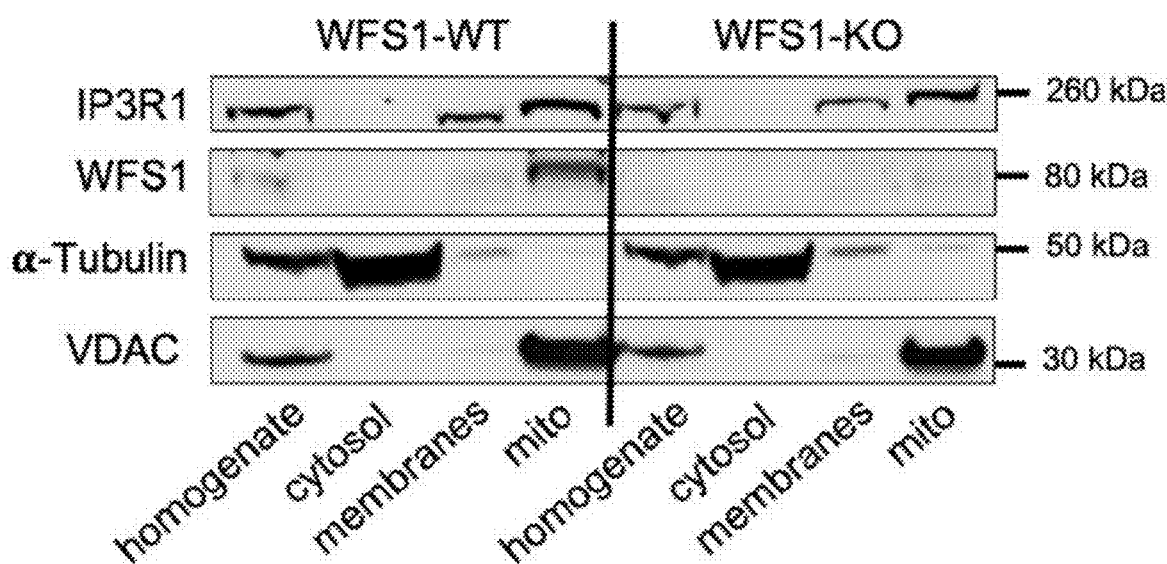
FIGURE 2S M

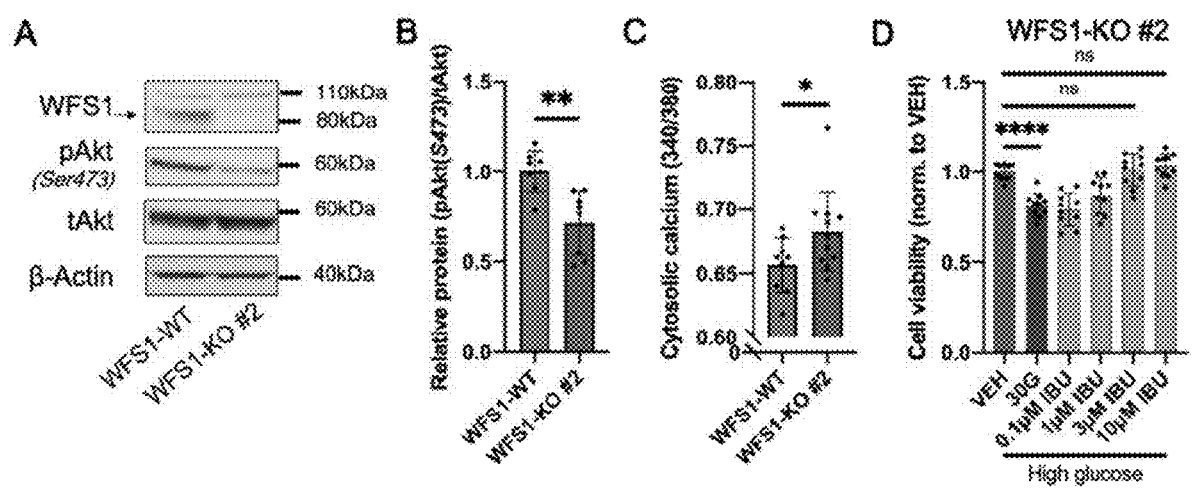
FIGURE 38 A, B, C, D

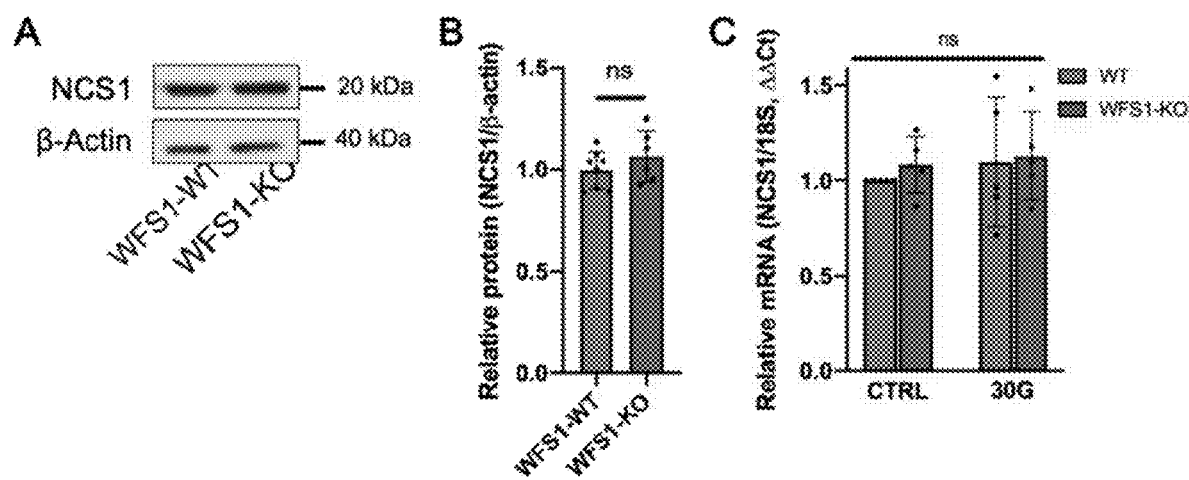
FIGURE 48 A, B, C

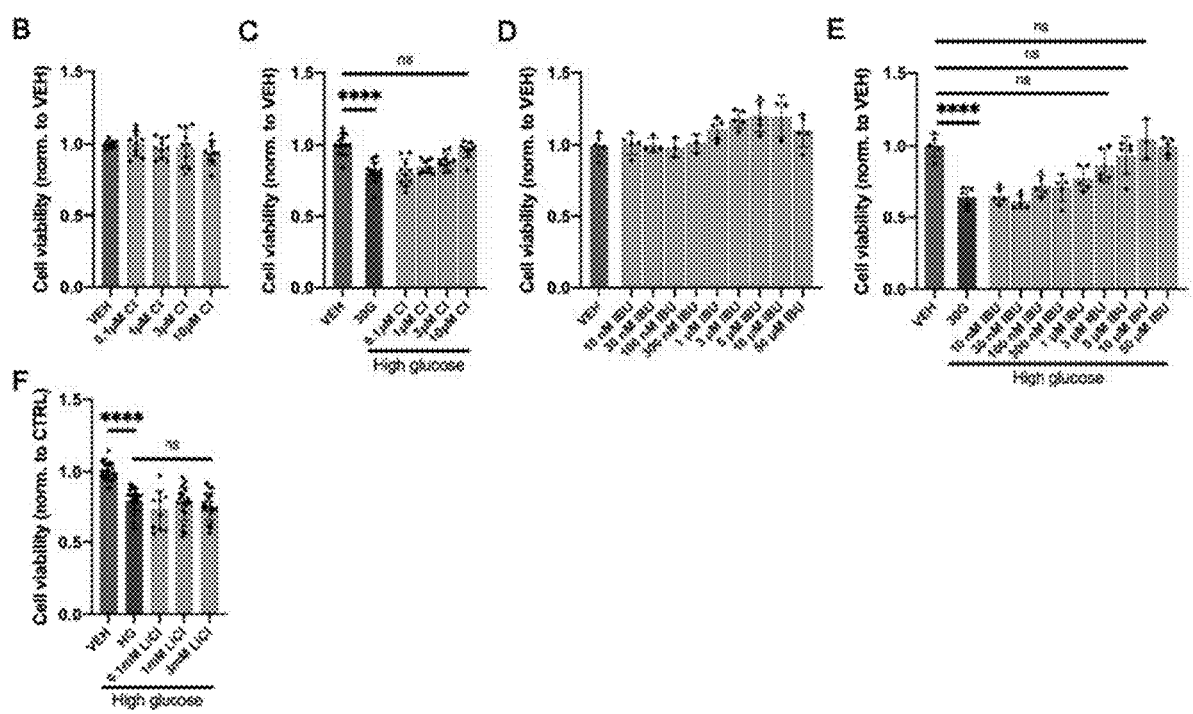

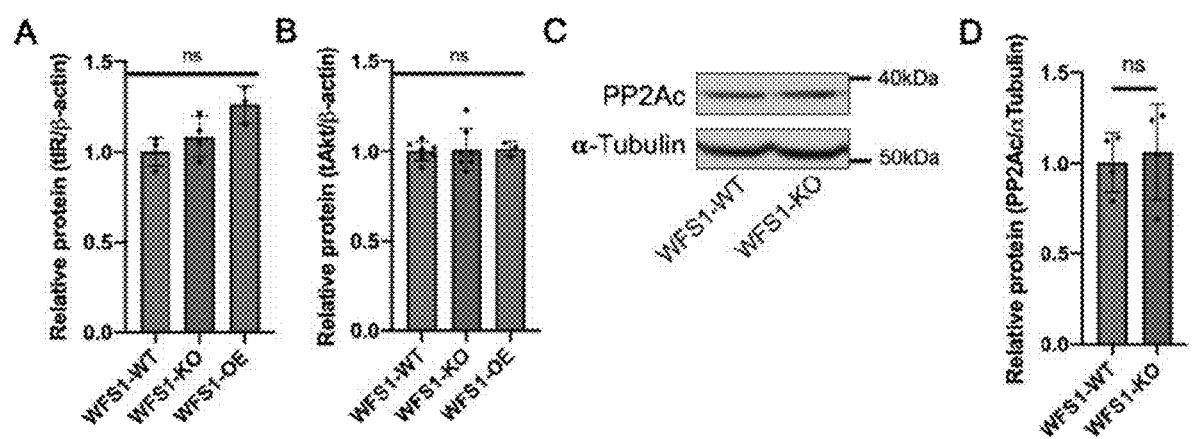
FIGURE 6S A, B, C, D

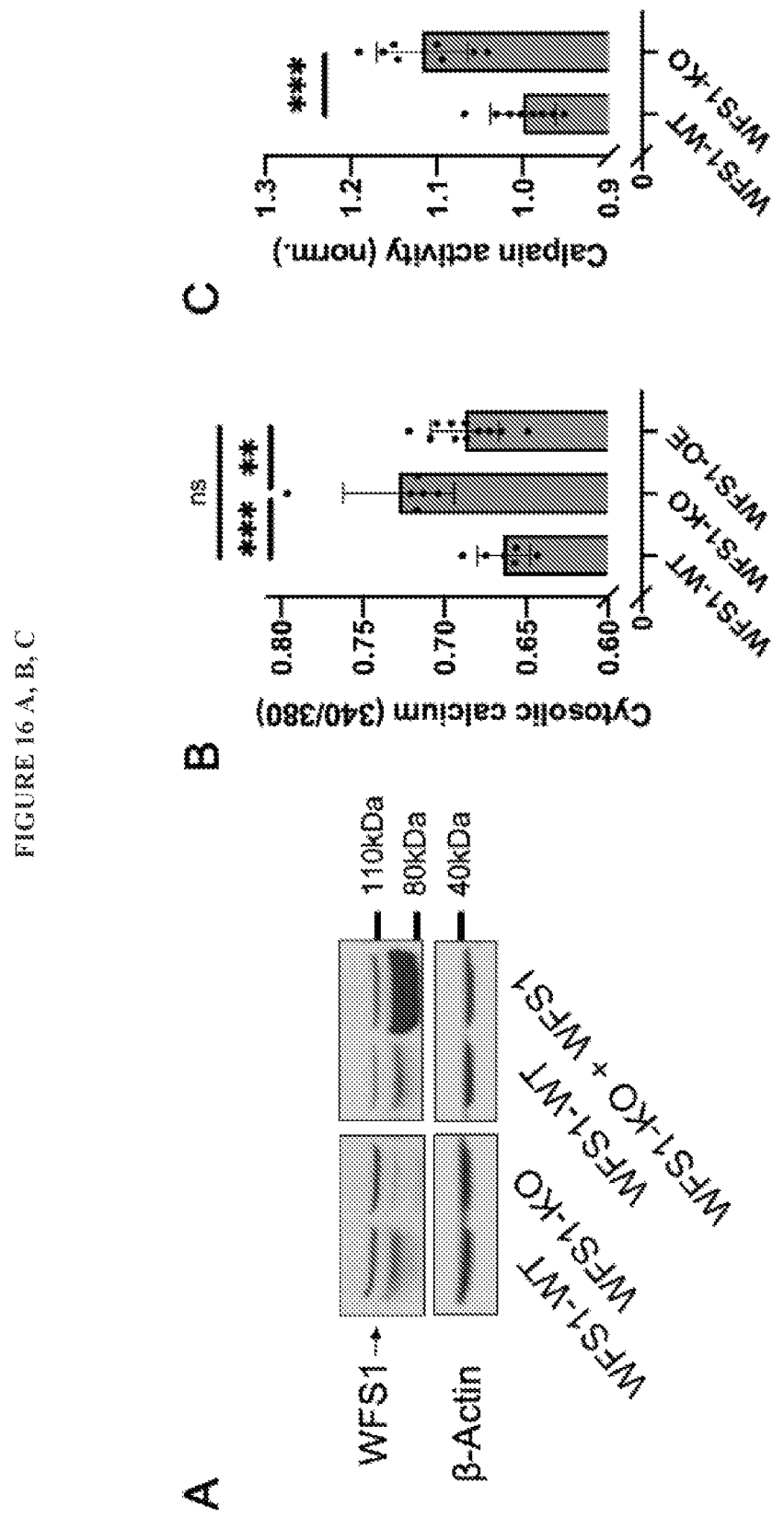
FIGURE 16 A, B, C

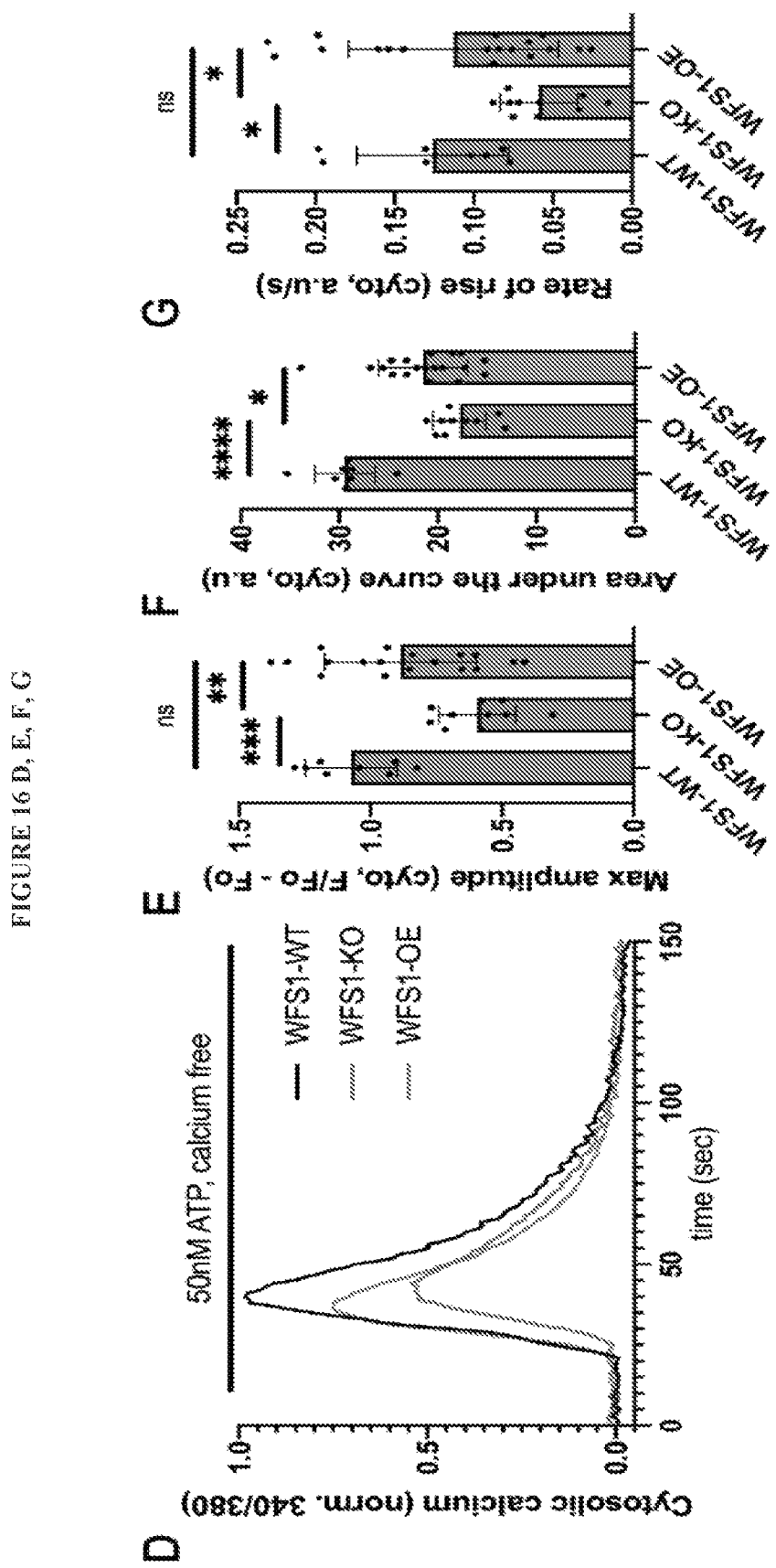
FIGURE 16 D, E, F, G

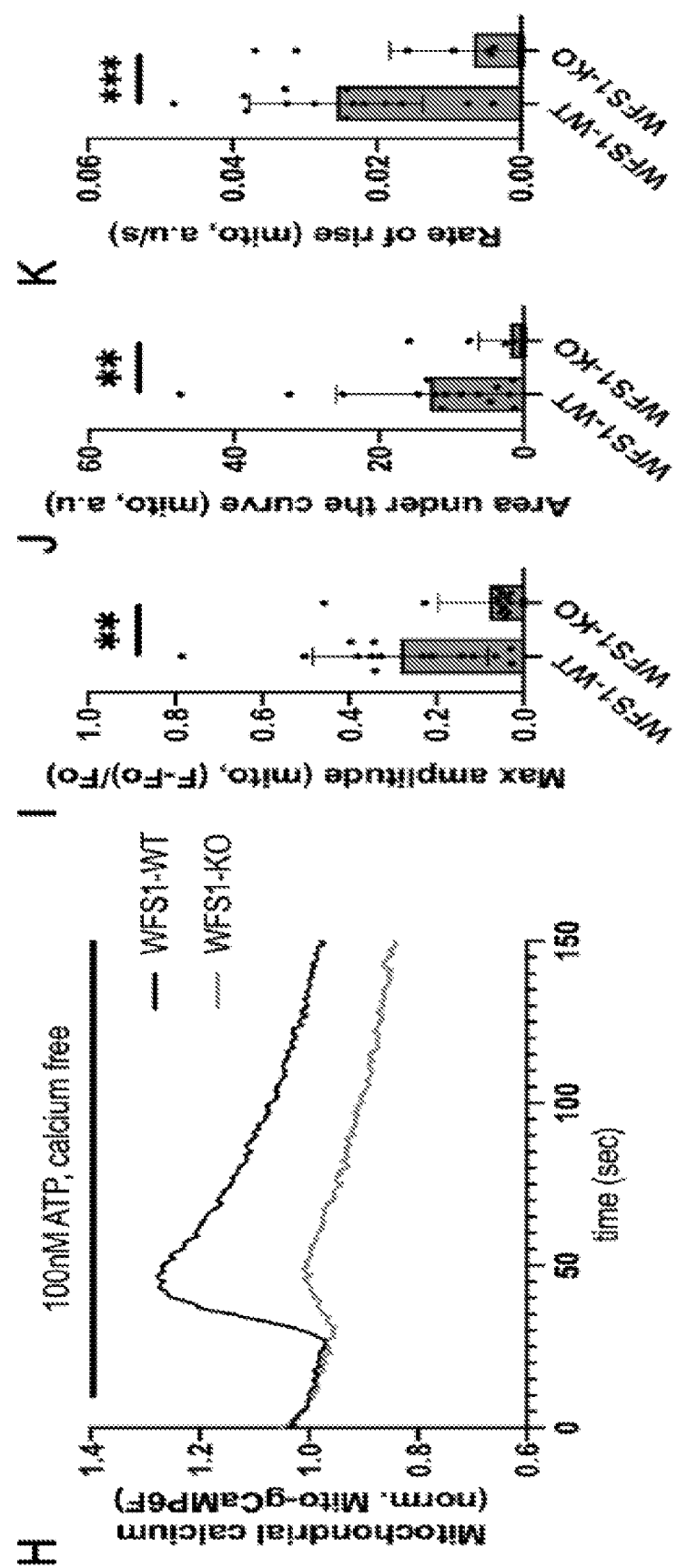
FIGURE 16 H, I, J, K

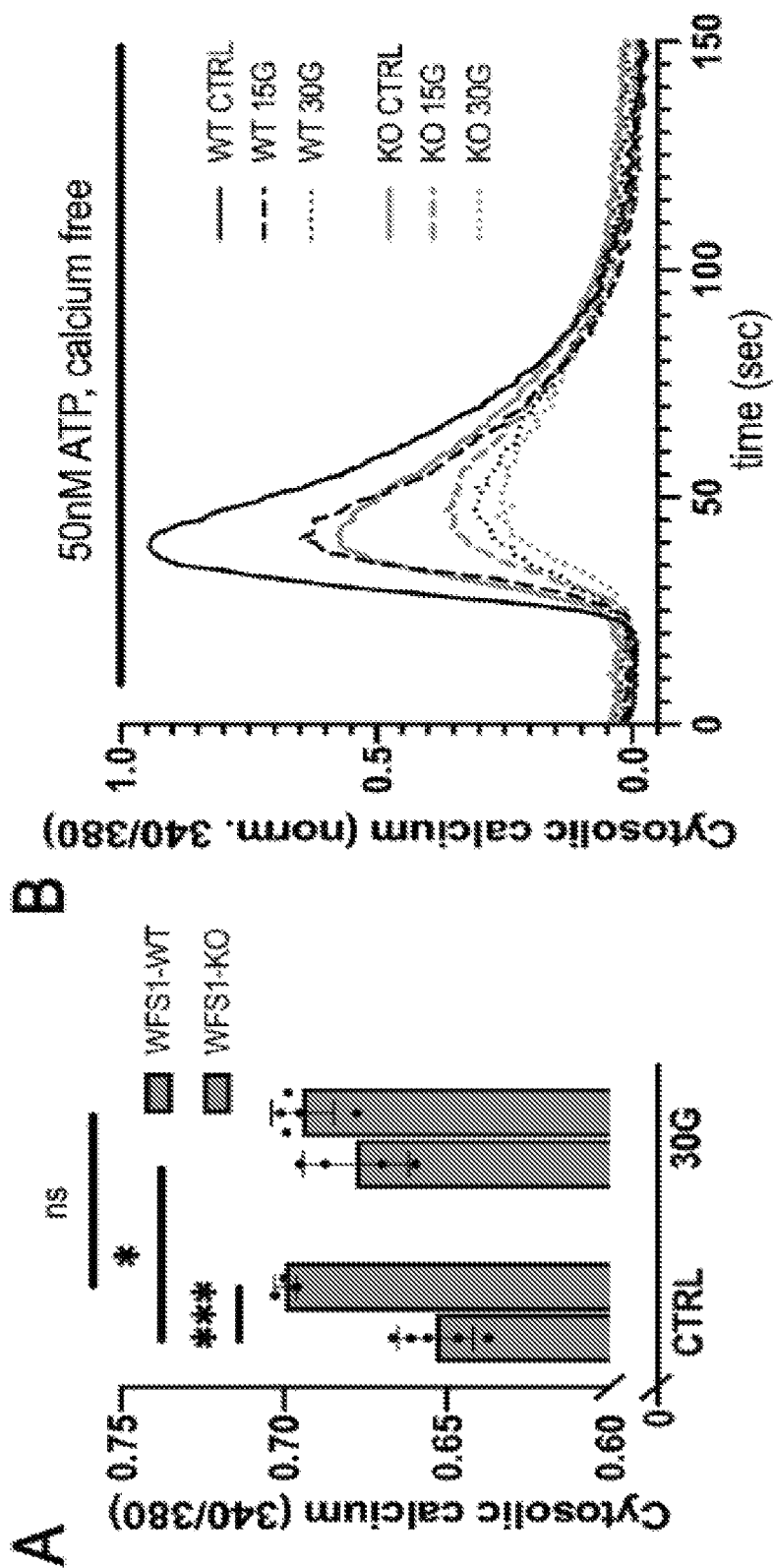
FIGURE 17 A, B

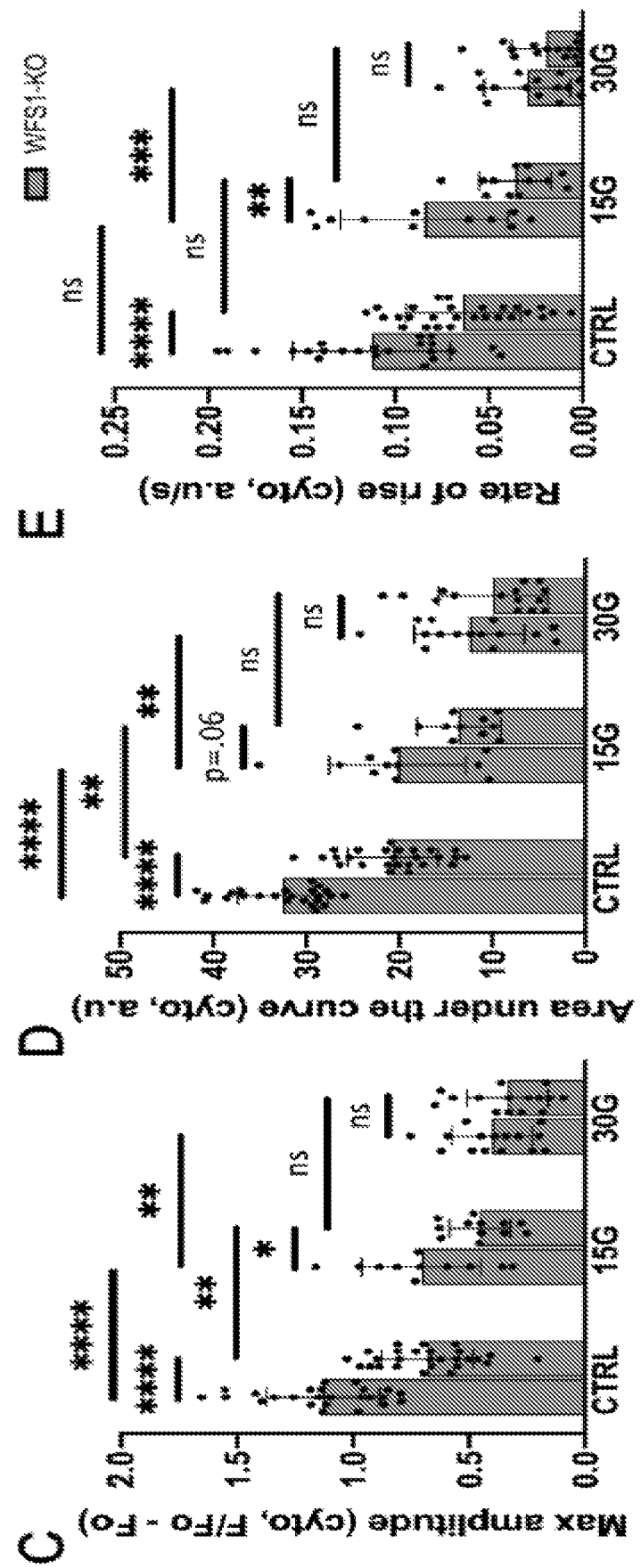
FIGURE 17 C, D, E

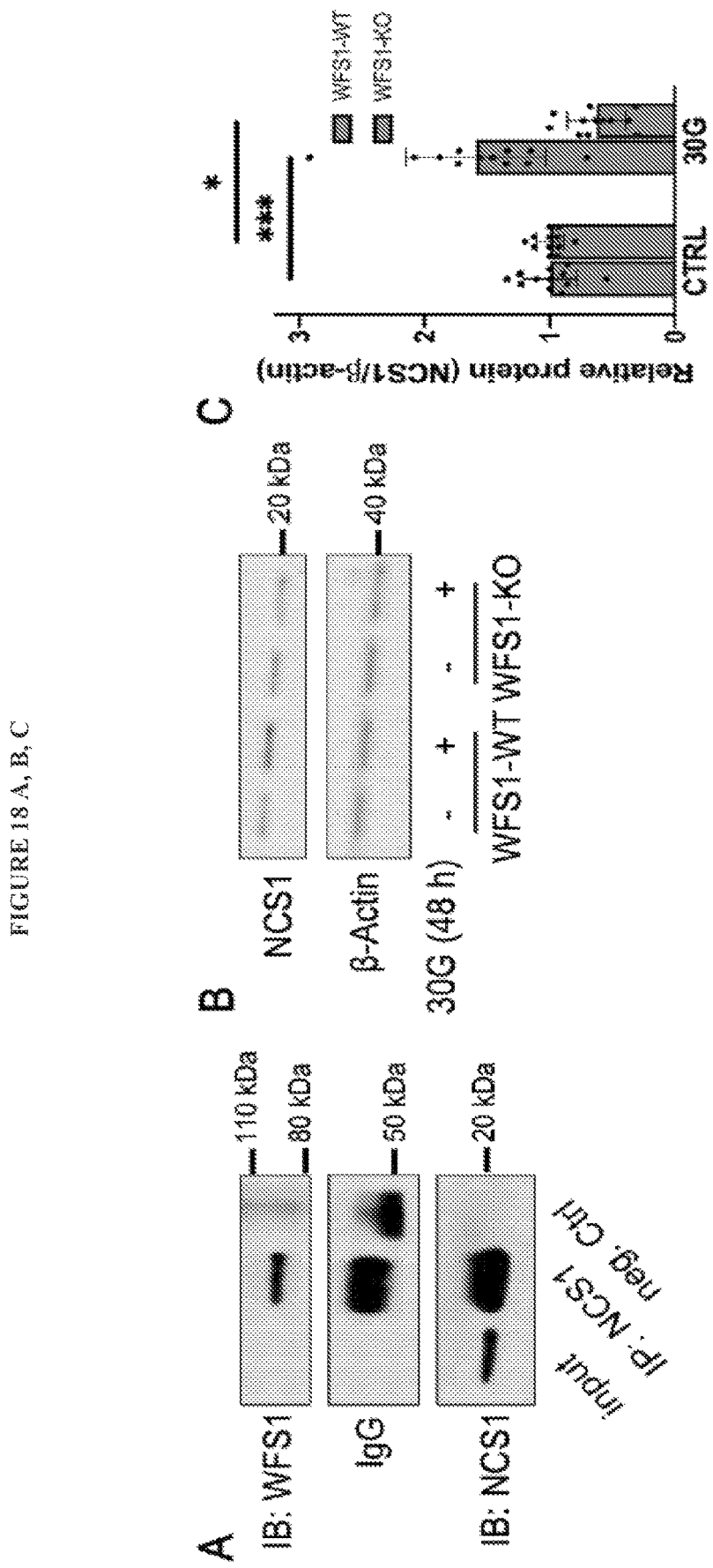
FIGURE 18 A, B, C

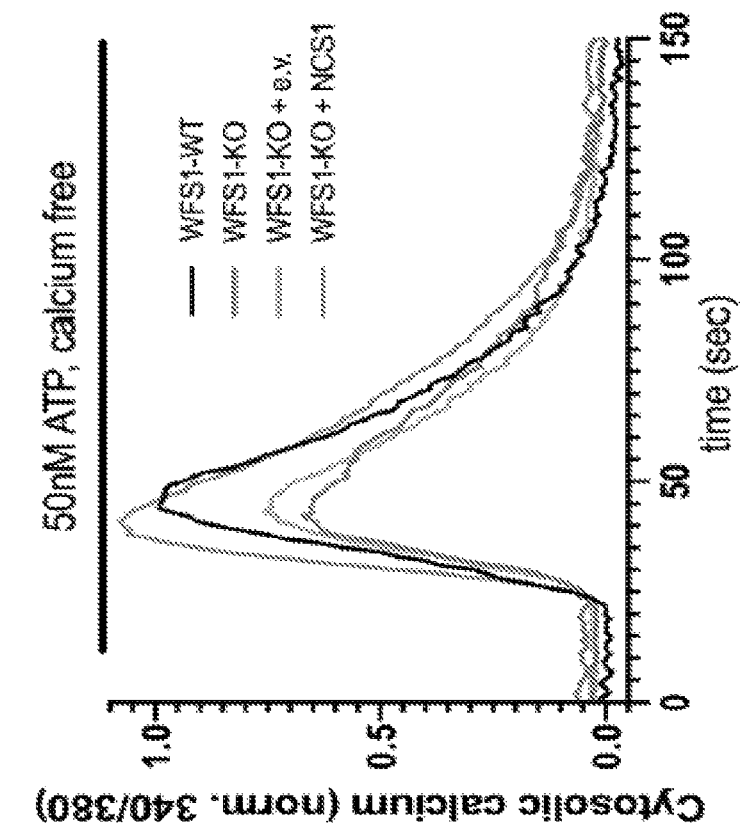
FIGURE 18 D, E

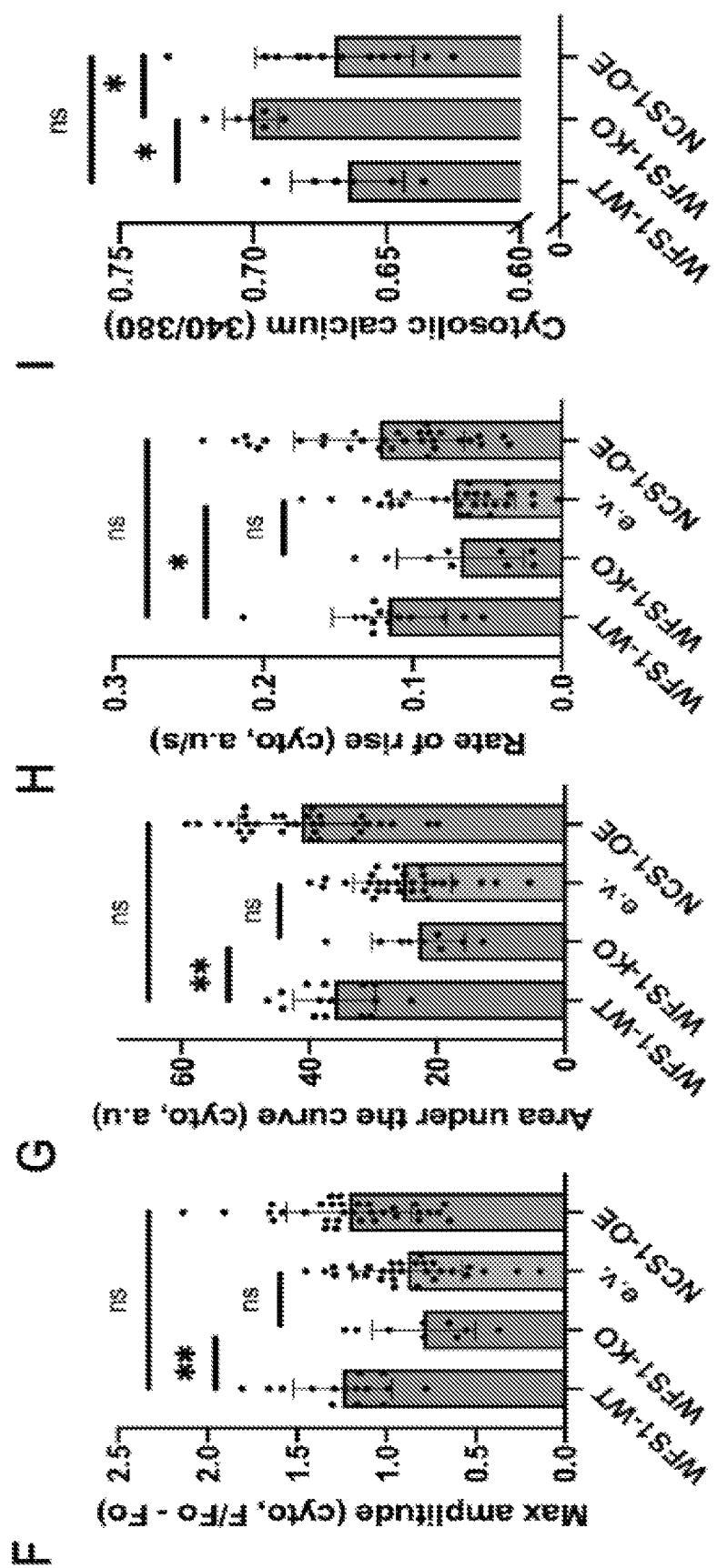
FIGURE 18 F, G, H, I

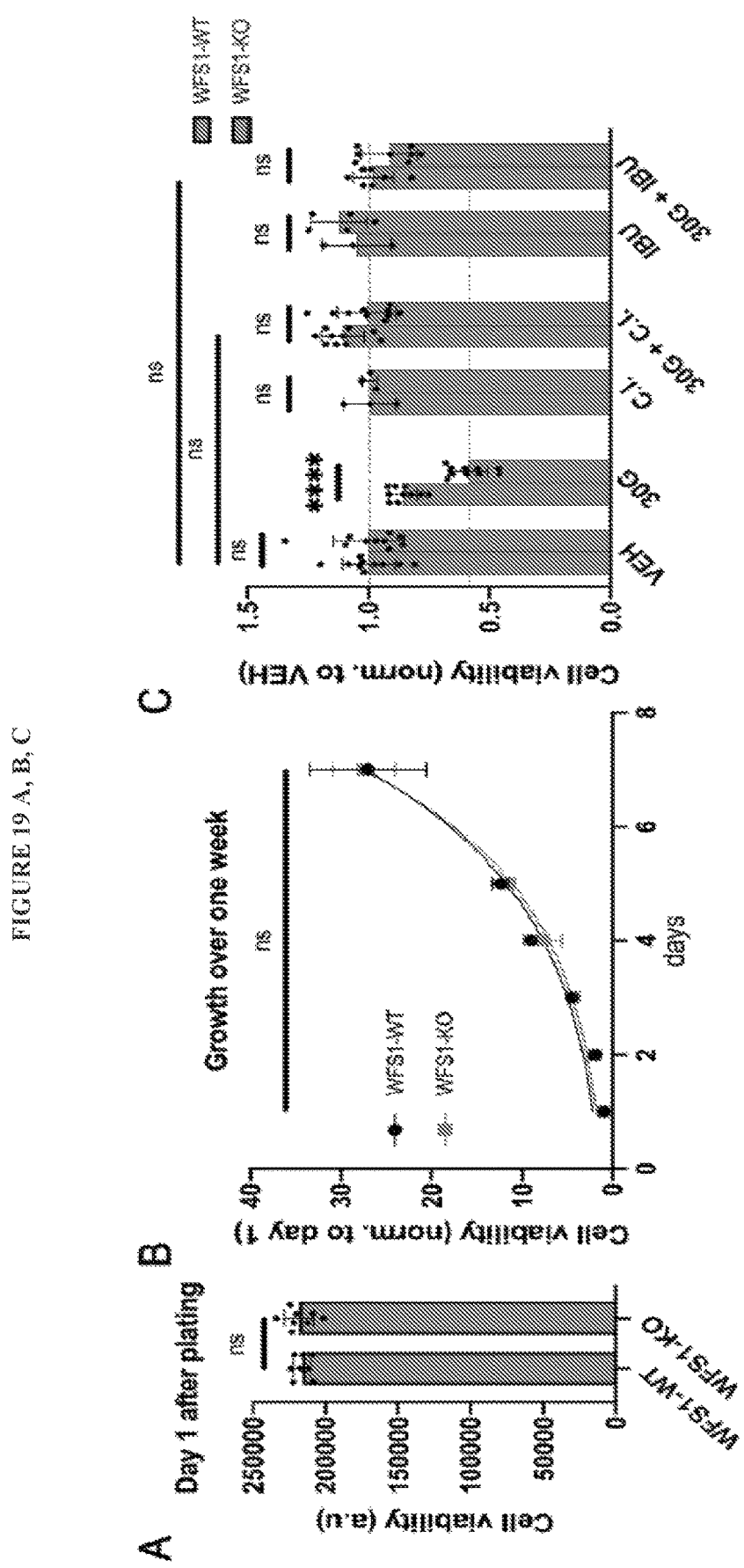
FIGURE 19 A, B, C

FIGURE 19 D, E
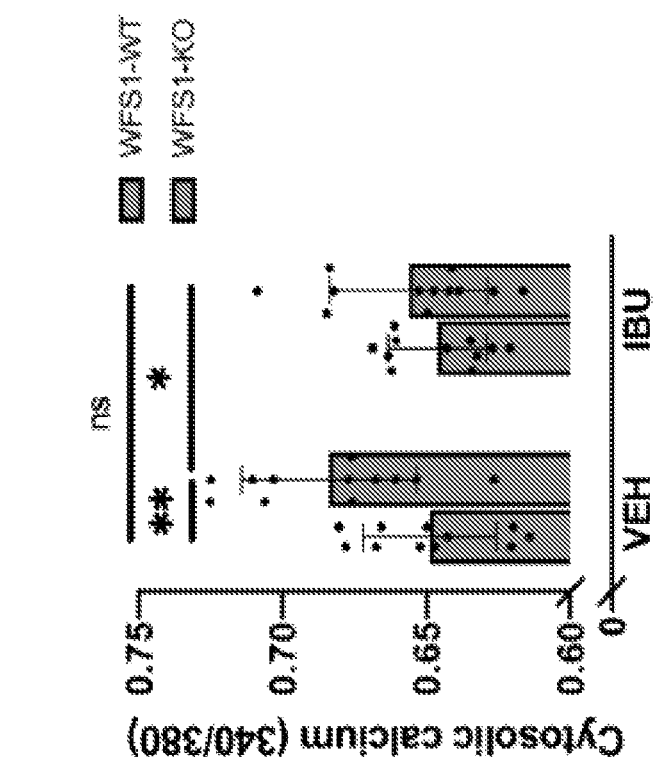
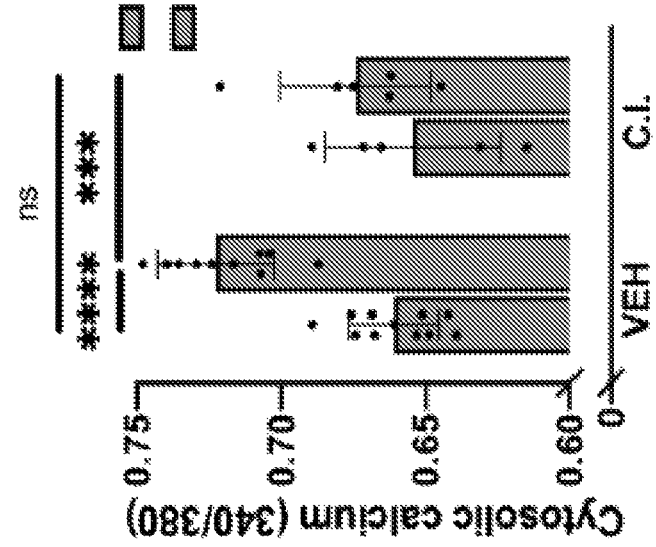

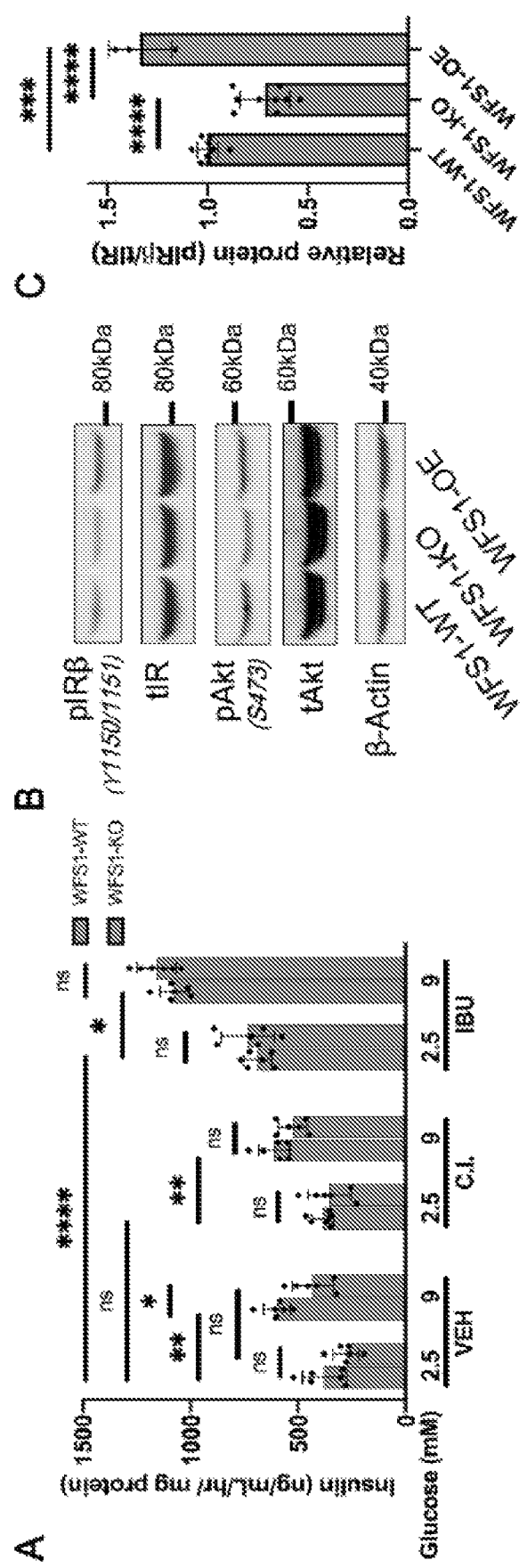
FIGURE 20 A, B, C

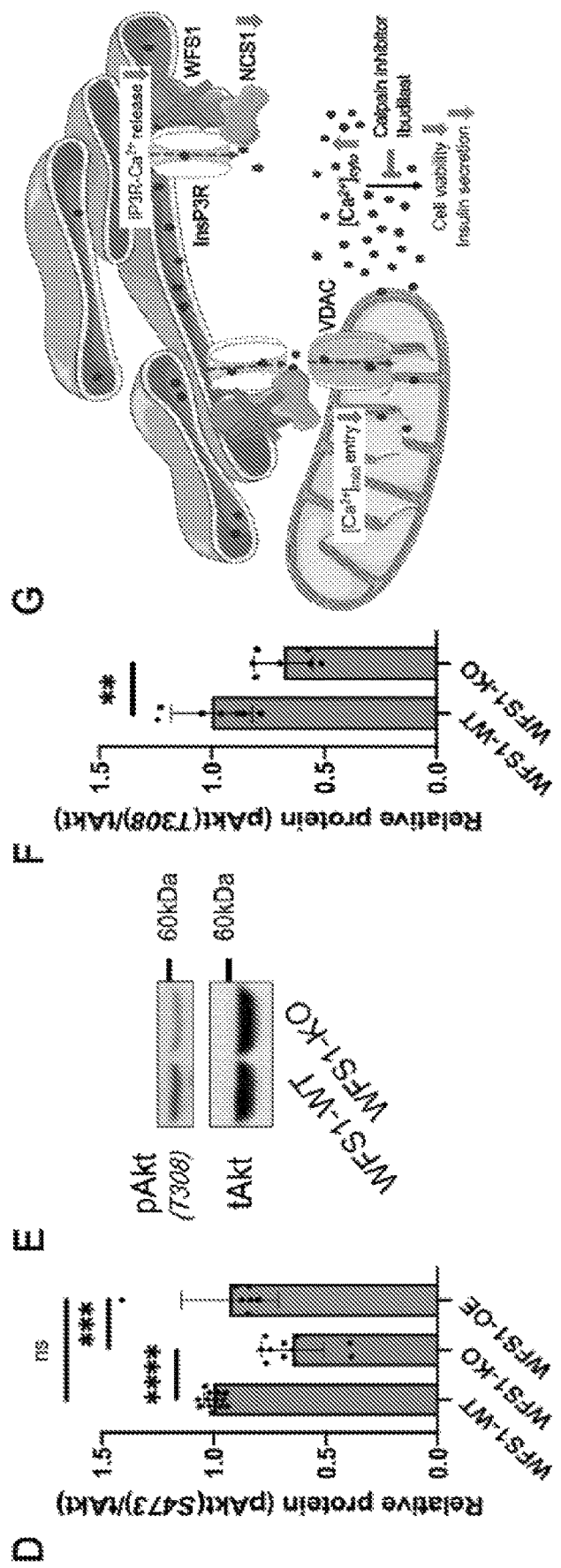
FIGURE 20 D, E, F, G

TREATMENT FOR WOLFRAM SYNDROME

This application is a US National Phase filing of PCT application no. PCT/US20/34539 filed on May 26, 2020, which claims the benefit of priority of U.S. Provisional Application Ser. No. 62/860,033, of identical title, filed Jun. 11, 2019, the entire contents of each of said applications are incorporated by reference in its entirety herein.

RELATED APPLICATIONS AND GRANT SUPPORT

This invention was made with government support under P01DK057751, DK112921, DK020579, TR002065 and F30DK111070 awarded by the National Institutes of Health. The government has certain rights in the invention.

FIELD OF THE INVENTION

The present invention is directed to a novel treatment for Wolfram Syndrome, to methods of treatment in order to delay, inhibit, ameliorate and/or reduce the likelihood of symptomology of a patient with Wolfram Syndrome.

Background and Overview of the Invention

Wolfram syndrome is an orphan, autosomal recessive neuroendocrinological disease in which patients experience loss of physical and psychological functions. The cardinal manifestations include diabetes mellitus, diabetes insipidus, bilateral optic atrophy, hearing and vision loss along with progressive motor, autonomic and psychiatric abnormalities. The course of Wolfram syndrome is progressive, and the prognosis is poor and typically fatal by mid-adulthood. Only palliative treatments exist, there are no therapies to slow progression.

More specifically, Wolfram syndrome is an aggressive multisystem neurodegenerative and endocrinological disease, also known by the acronym DIDMOAD (diabetes insipidus, insulin-deficient diabetes mellitus, optic atrophy and deafness). (14) Wolfram syndrome is caused by mutations in the protein wolframin and is inherited in an autosomal recessive pattern. Patients typically are first identified around age 6 by glucosuria and diabetes mellitus, followed by marked loss of peripheral vision and color perception due to optic nerve atrophy around age 11 (15). 70% of Wolfram syndrome patients suffer from central diabetes insipidus and neuron-based hearing loss. Urinary tract manifestations are another main clinical finding for patients affecting the majority of this population. More than half of patients develop neurological or psychiatric disorders, most commonly manifested as problems with balance and coordination (ataxia), seizures, and peripheral neuropathy beginning in early adulthood (16). Psychiatric disorders associated with Wolfram syndrome include psychosis, episodes of severe depression, and impulsive and aggressive behavior. Brain stem atrophy is also a prominent feature and it is this effect that leads to death, secondary to central apnea (15). Wolfram syndrome is often fatal by mid-adulthood (17) due to complications arising from the many features of the condition (3).

The inventor of the present application previously identified drugs that inhibit NCS1 function as part of a study of chemotherapy induced peripheral neuropathy (CIPN). Examples from all classes of the drugs that are effects in CIPN were tried. The inventor was completely surprised that only one of the compounds was effective in maintaining cell viability and function in cells with protein mutations that cause Wolfram Syndrome. This drug has never been considered as a candidate for therapy in Wolfram Syndrome.

Using the inventor's extensive knowledge of the calcium signaling complex that includes neuronal calcium sensor 1 (NCS1), the current novel therapy for Wolfram Syndrome has been identified. The present invention represents the first therapy for Wolfram Syndrome. No other therapies exist.

Wolfram Syndrome is a rare genetic disorder affecting people who are homozygous for mutations in wolframin. Given the present invention, this may be expanded to patients who are carriers in wolframin (heterozygous). Heterozygous individuals have a 25 fold or higher incidence of mood disorders, another condition that needs new improved therapies.

BRIEF DESCRIPTION OF THE INVENTION

The present invention is directed to a novel treatment for Wolfram Syndrome and to methods for treating, inhibiting, ameliorating, reducing the likelihood and/or delaying the onset of symptoms which occur as a consequence of Wolfram Syndrome and its progression. In addition, in embodiments, the present invention is directed to methods of treating, inhibiting, ameliorating, reducing the likelihood and/or delaying the onset of symptoms which are associated in patients who are heterozygous carriers in wolframin, particular mood disorders, bipolar disorder, depression, severe depression and impulsive verbal and physical aggression which are often exhibited by these individuals.

In an embodiment, the present invention is directed to the use of Ibudilast (AV411) or an analog or derivative thereof, including AV1013, in the treatment of Wolfram Syndrome in a patient or subject in need, the method comprising administering to a patient with Wolfram Syndrome an effective amount of Ibudilast (AV411) or analog or derivative thereof, including AV1013 or a related analog to treat, inhibit, ameliorate, reduce the likelihood and/or delay the onset one or more symptoms associated with Wolfram Syndrome in an individual including premature death, diabetes mellitus, diabetes insipidus, visual impairment, including optical atrophy, color blindness, slow reacting iris, high frequency hearing loss and tonal deafness, emotional agitation, tremors, seizures, peripheral neuropathy, autonomic dysfunction, ataxia, ptosis, nystagmus, endocrinopathies, brainstem atrophy, gastrointestinal disorders, including dysmotility (diarrhea/constipation), urinary tract atony, urinary incontinence, recurrent urinary infections, hydronephrosis, primary gonadal atrophy (especially in men), menstrual irregularities and delayed menarche, among others, including psychiatric disorders such as severe depression, bipolar disorder, impulsive verbal and physical aggression.

In an embodiment, the present invention is directed to the use of Ibudilast (AV411) or an analog or derivative thereof, including AV1013 in the treatment of heterozygous wolframin in a patient or subject in need to treat, inhibit, ameliorate, reduce the likelihood and/or delay the onset of one more symptoms associated with heterozygous wolframin including psychiatric disorders, especially depression or severe depression.

These and/or other embodiments are described in the detailed description of the invention which follows.

BRIEF DESCRIPTION OF THE FIGURES

FIG. 16 shows that WFS1 regulates intracellular calcium homeostasis in INS1 cells. (A) Western blot confirming the loss of WFS1 protein in WFS1-KO cells and the re-expression of WFS1 in WFS1-KO cells (WFS1-OE). (B) WFS1-KO cells exhibited significantly elevated resting cytosolic calcium compared to WFS1-WT cells, which could be rescued by re-expressing WFS1. (C) WFS1-KO cells showed significantly higher calpain activity than WFS1-WT cells. (D) Panel shows averaged traces of 8-18 coverslips for each cell type in response to 50 nM ATP. (E-G) Compared to WFS1-WT cells, WFS1-KO cells showed decreased max amplitude, area under the curve, and rate of rise for the cytosolic calcium traces shown in D. Re-expressing WFS1 fully rescued max amplitude and rate of rise and partially rescued area under the curve. (H) Panel shows averaged traces of 15 coverslips for each cell type (both WFS1-WT and WFS1-KO cells stably expressing mito-gCaMP6F) in response to 100 nM ATP. (I-K) Compared to WFS1-WT cells, WFS1-KO cells showed decreased max amplitude, area under the curve, and rate of rise for the mitochondrial calcium traces shown in H.

FIG. 17 shows that WFS1-KO cells show more severely impaired calcium signaling due to hyperglycemia. Cells were incubated for 24 hours with normal medium (CTRL) or medium with 15 mM or 30 mM additional glucose (15G and 30G, respectively) prior to imaging. (A) WFS1-WT cells showed elevated resting cytosolic calcium after incubation with 30G, whereas WFS1-KO cells showed no change. (B) Panel shows averaged traces of 12-25 coverslips for each condition in response to 50 nM ATP. Glucose toxicity caused impairments of ATP-evoked calcium transients in a concentration-dependent manner. However, WFS1-KO cells showed a more impaired response at CTRL and 15G. At 30G, both WFS1-WT and WFS1-KO cells were equally impaired. (C-E) Quantification of max amplitude, area under the curve, and rate of rise for the cytosolic calcium traces shown in B.

FIG. 19 shows that calpain inhibitor XI and ibudilast rescue cell viability and resting cytosolic calcium in WFS1-KO cells. (A) Measurement of cell viability of WFS1-WT and WFS1-KO cells showed no difference under control conditions on day 1. (B) Measurement of growth over 7 days showed no difference between WFS1-WT and WFS1-KO cells. (C) Measurement of cell viability, normalized to CTRL conditions. Treatment combinations as indicated for 48 hours, 30G=30 mM additional glucose, C.I.=calpain inhibitor XI (10 µM), IBU=ibudilast (10 µM). WFS1-KO cells showed a significantly larger reduction in cell viability compared to WFS1-WT cells. Cell viability in both cell lines were rescued by C.I. and IBU. 24 h treatment with (D) calpain inhibitor XI (10 µM) or (E) ibudilast (10 µM) reversed elevated cytosolic calcium in WFS1-KO cells without affecting WFS1-WT cells.

FIG. 2O shows that WFS1-KO cells exhibit decreased insulin secretion, which can be reversed by calpain inhibitor XI and ibudilast. (A) Measurement of glucose-stimulated insulin secretion using insulin ELISA assays, at baseline (2.5 mM glucose) and after stimulation (9 mM glucose). WFS1-WT cells showed significantly higher insulin secretion than WFS1-KO cells under control conditions. Treatment with 10 µM calpain inhibitor XI or 10 µM ibudilast ameliorated the difference between WFS1-WT and WFS1-KO cells. (B) Representative blot showing protein abundance of the insulin signaling pathway. (C-D) Quantification of A (3-10 independent preparations). Compared to WFS1-WT cells, WFS1-KO showed a significant reduction in pIRβ (Y1150/1151) and pAKT (S473). Re-expressing WFS1 in WFS1-KO cells increased levels of pIRβ and pAKT expression at least to WFS1-WT cells. (E) Representative blot showing protein abundance of pAKT (T308). (F) Quantification of D (7 independent preparations). pAKT (T308) was significantly downregulated in WFS1-KO cells. (G) Proposed model. Loss of WFS1 results in global calcium dysregulation which impairs cell viability and insulin secretion. Calpain inhibitor XI and ibudilast can restore proper β-cell function, suggesting them as drug candidates for the treatment of Wolfram syndrome and similar diseases.

FIG. 1S shows that WFS1-WT control and WFS1-KO cells were generated using CRISPR-Cas by the Genome Engineering and iPSC Center at Washington University in St. Louis. (A) gRNA was designed to target an early, conserved exon. (B-C) Sequencing results for the cell lines obtained. WFS1-KO clone #1 was used for all experiments shown in the main figures. Experiments using WFS1-KO clone #2 to validate the findings in clone 1 were included in FIG. 3S. In both clones, insertion and deletion mutations resulted in immature stop codons before a.a. (amino acid) 230 in both alleles. The WT cell line was obtained from a clone that did not show CRISPR modification.

FIG. 2S shows that WFS1 regulates intracellular calcium homeostasis in INS1 cells. (A) WFS1-KO cells showed a significant elevation of cytosolic calcium compared to WFS1-WT cells. (B) Panel shows averaged traces of 5-6 coverslips for each cell line in response to 1 µM thapsigargin. The Fluo-4-AM signal was normalized to intensity at 10 s. (C, D) Quantification of area under the curve and max amplitude for cytosolic calcium traces shown in B, no difference was observed. (E) Panel shows averaged traces of 9-10 coverslips for each cell type in response to 50 nM ATP. The fluo-4-AM signal was normalized to intensity at 10 s. (F-H) Compared to WFS1-WT cells, WFS1-KO cells showed decreased area under the curve, max amplitude, and rate of rise for the cytosolic calcium traces shown in E. (I) Representative blot of InsP3R1 and InsP3R3 protein abundance in WFS1-WT and WFS1-KO cells. (J-K) Quantification of I (from 4-7 independent preparations) showed no difference in InsP3R1 and InsP3R3 expression in both cell lines. (L) Representative blot of subcellular fractionations isolated obtained from HEK293 cells, c.m.=crude mitochondria, containing mitochondria and MAMs. Tubulin was used as a marker for the cytosolic proteins, VDAC for mitochondrial proteins and calreticulin for non-MAM ER-proteins. (M) Representative blot of subcellular fractionations obtained from INS1 WFS1-WT and WFS1-KO cells. Same markers as in L.

FIG. 3S shows the Validation of key findings in a second CRISPR-WFS1-KO INS1 clone. (A) Representative blot confirming loss of WFS1 in WFS1-KO clone 2, and showing protein abundance of pAkt (S473) and tAkt. (B) Quantification of B (from 7 independent preparations). (C) WFS1-KO clone #2 cells exhibited significantly elevated cytosolic calcium compared to WFS1-WT cells. (D) High glucose-induced loss of cell viability in WFS1-KO clone #2 cells was dose-dependently reversed by ibudilast.

FIG. 4S shows NCS1 protein and mRNA levels in WFS1-WT and WFS1-KO cells. (A) Representative blot showing NCS1 expression. (B) Quantification of A (from 6-8 independent preparations), normalized to WT, no difference was observed between cell lines. (C) Quantification of 5 independent qPCR experiments, no difference was observed between the different conditions.

FIG. 5S shows a drug screen for compounds that rescue cell viability in WFS1-KO cells. Compounds were selected to target WFS1, NCS1, and/or calcium signaling. (A) Preliminary screening of various drugs to prevent glucose toxicity. Following treatment with 30 mM additional glucose (30G, 48 h), both WFS1-WT and WFS1-KO cells showed significant cell death as compared to cells cultured in normal medium. However, WFS1-KO cells showed more severe cell death compared to WFS1-WT and WFS1-OE cells at high glucose. Of the 7 compounds tested, only calpain inhibitor XI and ibudilast rescued cell viability back to normal level. (B) Calpain inhibitor XI did not affect cell viability in WFS1-KO cells at baseline. (C) Calpain inhibitor XI dose-dependently reversed high glucose-induced loss of cell viability in WFS1-KO cells. (D) Ibudilast slightly raised cell viability in WFS1-KO cells at baseline. (E) Ibudilast dose-dependently reversed high glucose-induced loss of cell viability in WFS1-KO cells. (F) Lithium did not reverse hyperglycemia-induced loss of cell viability in WFS1-KO cells.

FIG. 6S shows total IR, total Akt, and PP2Ac protein levels in WFS1-WT and WFS1-KO cells. (A) Total IR and (B) total Akt protein levels were not changed, representative blot shown in FIG. 5SA. (C) Representative blot showing protein abundance of PP2Ac in WFS1-WT and WFS1-KO cells. (D) Quantification of C (from 4 independent preparations), no significant difference was observed between cell lines.

DETAILED DESCRIPTION OF THE INVENTION

Figure 1:
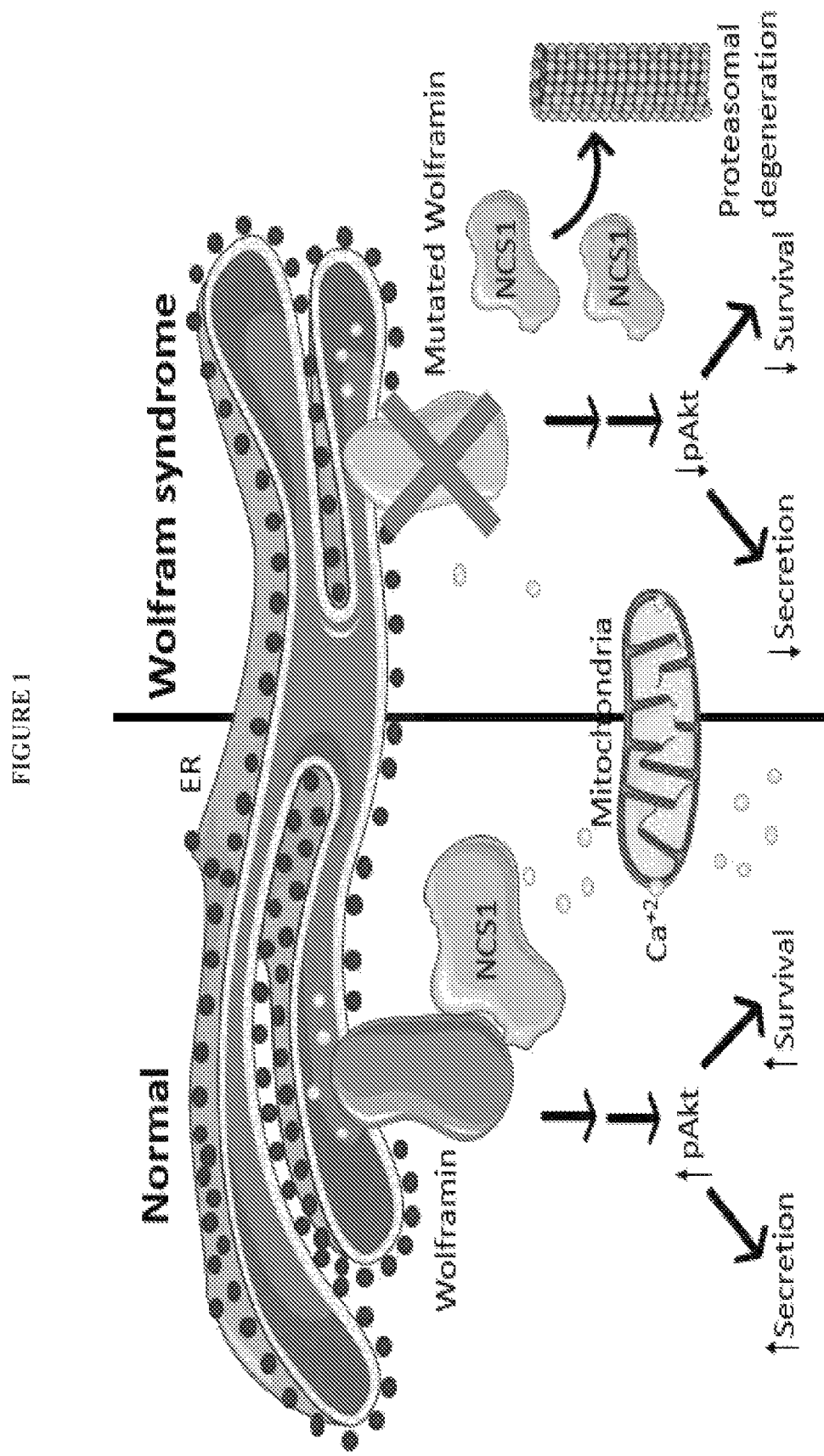
FIG. 1 shows a model for the effects of mutations to wolframin on NCS1, calcium ($Ca^{2+}$) signaling, secretion, and cell survival.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges that may independently be included in the smaller ranges are also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds arm to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal, especially including a domesticated animal and preferably a human, to whom treatment, including prophylactic treatment (prophylaxis), with the compounds or compositions according to the present invention is provided. For treatment of those infections, conditions or disease states which are specific for a specific animal such as a human patient, the term patient refers to that specific animal. In most instances, the patient or subject of the present invention is a human patient of either or both genders.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts (including any pharmaceutically acceptable salt) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "Wolfram's syndrome" is used to describe a rare genetic disorder affecting people who are homozygous for mutations in wolframin. Wolfram syndrome is an inherited condition that is typically associated with childhood-onset insulin-dependent diabetes mellitus and progressive optic atrophy. In addition, many people with Wolfram syndrome also develop diabetes insipidus and sensorineural hearing loss. An older name for the syndrome is DIDMOAD, which refers to diabetes insipidus, diabetes mellitus, optic atrophy, and deafness. Some people have mutations in the same gene that causes Wolfram syndrome but they do not get all the features of the syndrome, so they are said to have WFS1-related disorders. For example, this name would be used to describe someone with severe sensorineural hearing loss caused by WFS1 gene mutations but without diabetes or other features. WFS1-related disorders include sensorineural hearing loss, diabetes mellitus, psychiatric illness/disorders, and variable optic atrophy.

Symptoms/secondary effects of Wolfram's syndrome include premature death, diabetes mellitis, diabetes insipidus, visual impairment, including optical atrophy, color blindness, slow reacting iris, high frequency hearing loss and tonal deafness, emotional agitation, tremors, seizures, peripheral neuropathy, autonomic dysfunction, ataxia, ptosis, nystagmus, endocrinopathies, brainstem atrophy, gastrointestinal disorders, including dysmotility (diarrhea/constipation), urinary tract atony, urinary incontinence, recurrent urinary infections, hydronephrosis, primary gonadal atrophy (especially in men), menstrual irregularities and delayed menarche, among others, including psychiatric disorders such as severe depression, bipolar disorder, impulsive verbal and physical aggression. Therapy pursuant to the present invention involves inhibiting, delaying the onset of and/or ameliorating at least one and preferably numerous symptoms/secondary effects associated with Wolfram's syndrome. Often diabetes mellitis and/or diabetes insipidus or one or more psychiatric disorders are ameliorated pursuant to treatment according to the present invention.

The present invention is also directed to treating individuals who suffer from "heterozygous wolframin", rather than homozygous or full Wolfram syndrome (described above). Individuals with heterozygrous wolframin, far more numerous in numbers than individuals with Wolfram syndrome, often suffer from psychiatric disorders, especially depressive disorders including bipolar disorder, depression, severe depression and impulsive verbal and physical aggression.

The term "ibudilast" or AV411 or a derivative or analog thereof is used to describe certain pyrazolo[1,5α]pyridine compounds which find use in the present invention. Thus, ibudilast compounds useful in the present invention include Ibudilast (AV411), AV1013 (which substitutes a free amine for one of the two methyl groups in the 2-methylbutanone side chain of Ibudilast) as well as pyrazolo[1,5α]pyridine phosphodiesterase inhibitors disclosed in international application publication WO2007146087, the entire contents of which are incorporated by reference herein.

Preferred ibudilast derivative or analogs thereof include ibudilast and related compounds according to the chemical structure:

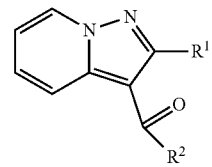

Where $R^1$ is a $C_1$-$C_6$ alkyl, preferably a $C_2$ or $C_3$ alkyl, most often isopropyl; and
$R^2$ is $C_1$-$C_6$ alkyl (preferably a $C_2$-$C_4$ alkyl, most often isopropyl) or,

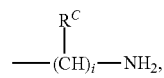

where
each $R^C$ is independently H or $C_1$-$C_3$ alkyl (preferably H or methyl); and
i is 0, 1, 2 or 3 (preferably 0 or 1), or a pharmaceutically acceptable salt, enantiomer or diastereomer thereof.

In preferred compounds, $R^1$ is isopropyl and $R^2$ is isopropyl (ibudilast AV411) or —C(H)(CH$_3$)NH$_2$ (i is 1 and $R^C$ is methyl) (AV1013) or a pharmaceutically acceptable salt or enantiomer thereof.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. Salts of amines are often prepared by acidifying the free amine with an acid, especially a weak acid such as an organic acid to form an ammonium salt (e.g. ammonium lactate, ammonium acetate, ammonium chloride, ammonium sulfate, etc.), among other methods. The term "salt" shall mean any salt consistent with the use of the compounds according to the present invention. In the case where the compounds are used in pharmaceutical indications, including the treatment of Wolfram's syndrome, including heterozygous wolframin, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Compounds according to the present invention may be administered with one or more additional bioactive agents, especially including an additional agent for purposes of treating one or more symptoms or second disease states of Wolfram's syndrome or heterozygous wolframin.

Pharmaceutical compositions comprising combinations of an effective amount of at least one compound disclosed herein, often according to the present invention and one or additional compounds as otherwise described herein, all in effective amounts, in combination with a pharmaceutically effective amount of a carrier, additive or excipient, represents a further aspect of the present invention. These may be used in combination with at least one additional, optional bioactive agents, especially antibiotics as otherwise disclosed herein.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir, among others. The term "parenteral" as used herein includes subcutaneous, intravenous, intramuscular, intra-articular, intra-synovial, intrasternal, intrathecal, intrahepatic, intralesional, intraperitoneal and intracranial injection or infusion techniques. Preferably, the compositions are administered orally (including via intubation through the mouth or nose into the stomach), intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils arc conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as arc natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat symptoms which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional compound which may be used to a symptom of Wolfram syndrome or heterozygous wolframin or a secondary symptom or condition thereof.

Methods of treating patients or subjects in need for a symptom or condition of Wolfram syndrome or heterozygous wolframin as otherwise described herein, comprise administration of an effective amount of a pharmaceutical composition comprising therapeutic amounts of one or more of the compounds described herein and optionally at least one additional bioactive agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dose of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a human) suffering from Wolfram syndrome or heterozygous wolframin can be treated by administering to the patient (subject) an effective amount of a compound according to the present invention including pharmaceutically acceptable salts, solvates or polymorphs, thereof optionally in a pharmaceutically acceptable carrier or diluent, either alone, or in combination with other known antibiotic or pharmaceutical agents, preferably agents which can assist in treating the bacterial infection or ameliorate the secondary effects and conditions associated with the infection. This treatment can also be administered in conjunction with other conventional therapies known in the art.

The present compounds, alone or in combination with other agents as described herein, can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from about 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled and/or sustained release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions or cholestosomes may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

EXAMPLES

First Set

Wolfram Syndrome was previously considered a mitochondrial disease because of its symptoms and the presence of several studies reporting mitochondrial dysfunction. However, new evidence now suggests that Wolfram syndrome is caused primarily by endoplasmic reticulum (ER) dysfunction. The ER is a membrane-delineated intracellular compartment that is involved in many cellular processes including protein and lipid synthesis, calcium storage, detoxification, cell signaling, and apoptosis. It has been shown that pancreatic β cells (18) and neurons are exquisitely sensitive to ER dysfunction, probably because their high rates of protein synthesis. In Wolfram syndrome, pancreatic β cells and neuronal cells are selectively damaged by mutations in the WFS1 gene. This gene encodes a transmembrane protein, wolframin. localized to the ER. We have recently reported that ER calcium depletion leads to elevated ER stress levels, calpain activation, and the initiation of ER stress-associated pancreatic β cell death and neurodegeneration (19).

Several protein binding partners for wolframin have been proposed (20), but more information is needed to appreciate the functional consequences of these interactions. One of these binding proteins, neuronal calcium sensor 1 (NCS1), not only binds to wolframin, but a recent report suggests that nonfunctional wolframin loses its ability to bind to NCS1 (21) making NCS1 susceptible to calpain-dependent proteosomal degradation. A loss of NCS1 would lead to decreased calcium signaling (FIG. 1) which makes cells more susceptible to ER stress (22) and is essential for insulin secretion and cell survival. In Wolfram syndrome, these altered processes lead to changes in glucose tolerance and atrophy of neurons needed for hearing and vision.

Neuronal Calcium Sensor 1 (NCS1) Regulates Calcium Dependent Cell Functions.

NCS1 is a multi-functional calcium-binding protein found in virtually all cell types, especially epithelial cells and neurons (7). Binding of calcium to NCS1 induces a conformational change (23) that exposes a hydrophobic crevice for protein binding. NCS1 has a number of protein partners (7, 24) and these interactions affect a range of cellular processes including those related to transduction (7) and membrane trafficking (24, 25). Most relevant to this project, NCS1 regulates secretion (6), neurotransmitter release (26) and cell survival (27).

Calpain Activation and Wolfram Syndrome.

The inventor identified the calpain cleavage site on NCS1 (31) and showed that mutating residues in the calpain cleavage site prevents loss of NCS1 and maintains calcium homeostasis (32). Calpains, with calpains 1 and 2 being ubiquitously expressed and most well-characterized, form a family of promiscuous proteolytic enzymes that are essential for many biological functions (38). Calpains are found in almost all eukaryotes and some bacteria. Normally inactive, calpains are activated by high calcium levels following insults that trigger calcium flow through plasma membrane-associated channels or release from intracellular stores which includes both the ER and the mitochondria. Once activated, calpains cleave numerous protein substrates including membrane receptors, ion channels, structural proteins, kinases and phosphatases, ultimately leading to calcium dysregulation and cell death (39). Calpain hyperactivation is a major factor underlying neurodegeneration in traumatic brain injury (40), Alzheimer's disease (41), ischemia (42) and other neurodegenerative conditions (39).

After calpain is activated there is cleavage and degradation of a number of substrates, including NCS1, which then diminishes InsP3R-mediated calcium signaling. In addition to changes in calcium homeostasis, calpain hyperactivation facilitates a pro-inflammatory, pro-neurodegenerative environment (43-45). Normally, calpain activity is attenuated by activation of its endogenous inhibitor, calpastatin (CAST). We and other have shown that inhibition of calpain activity with calpain inhibitors or through overexpressing of CAST is effective in rescuing neurodegeneration at the molecular and behavioral levels (46-48). We also showed that overexpressing CAST protected NCS1 level and rescued calcium signaling in neuroblastoma cells treated with paclitaxel (11). However, the lack of inhibitor specificity and the broad range of calpain substrates present a major challenge for using direct calpain inhibitors to rescue neurodegeneration. We have searched for specific agents that prevent calpain activation (e.g., by decreasing calcium elevations) or protect critical proteins needed to prevent Wolfram syndrome.

Significance. Currently, no therapies for Wolfram syndrome exist. Our long-term goal is to establish an effective treatment for Wolfram syndrome and to test whether these strategies will address other diseases in which ER dysfunction is involved. We have recognized a new calcium signaling pathway that influences the progression of Wolfram syndrome. This pathway is known to be targeted by drugs and the effect of treatment can be assessed using non-invasive tests in mice (glucose tolerance test and hearing acuity). These tests, along with visual acuity assessment, can be translatable to human subjects.

Experimental Data

The experimental data presented herein show that wolframin and NCS1 interact and that there are functional consequences of these interactions.

Wolframin/NCS1 Interaction

Figure 2:
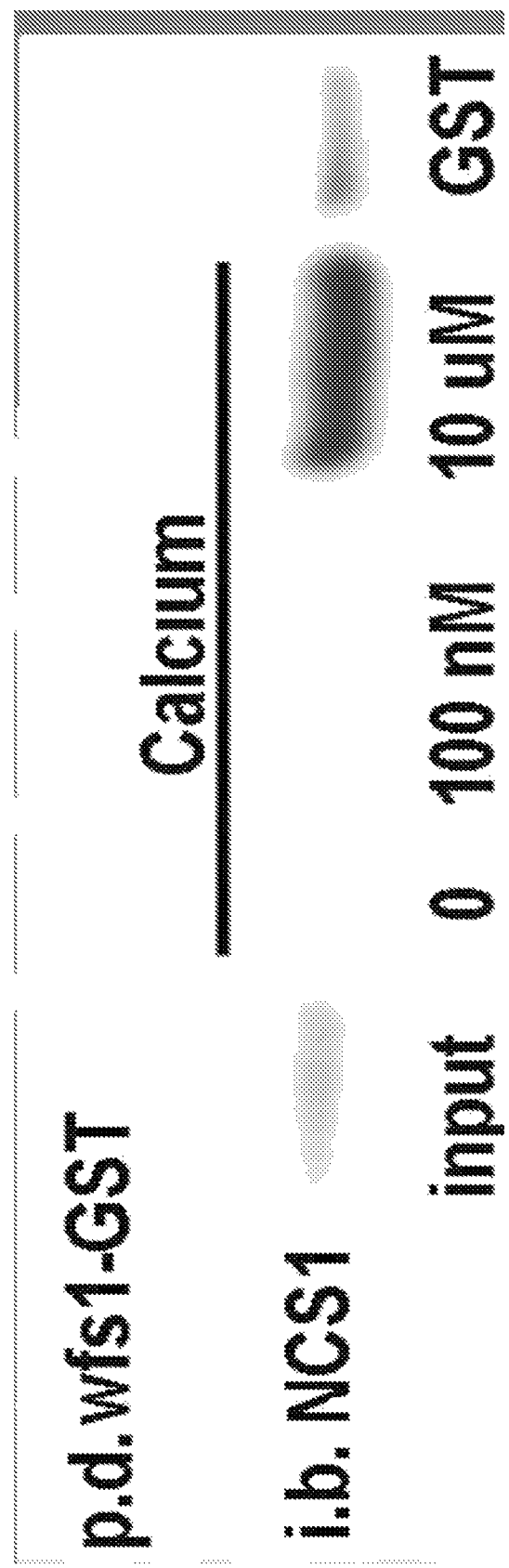
FIG. 2 shows that NCS1 and wolframin bind in a calcium dependent manner. NCS1 and the cytoplasmic domain of wolframin (wfs1-GST) were expressed in bacteria and NCS1 was purified. The cytoplasmic domain of wolframin had a GST tag that was used to pull down the protein complex. Increased free calcium, increased pull down of NCS1. Blot was probed with an antibody against NCS1. p.d.=pull down, i.b.=immunoblot
Figure 2B:
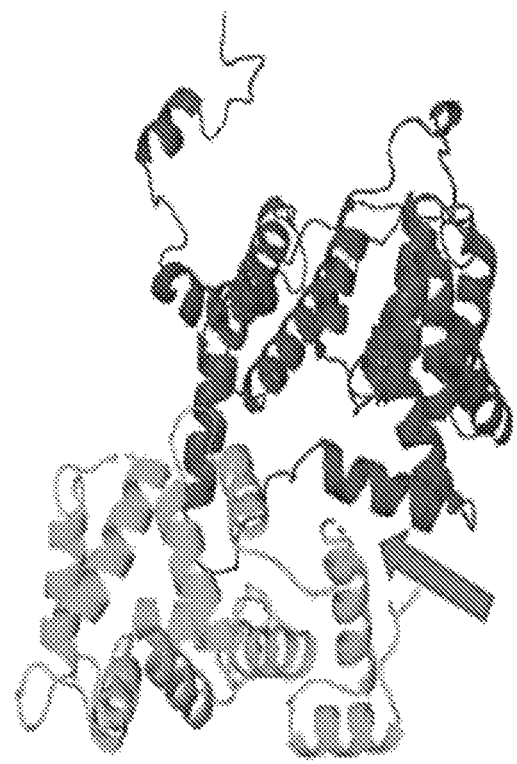
FIG. 2B shows the docking of NCS1 to the cytoplasmic domain of wolframin. NCS1 (green) is the crystal structure (1G81). The wolframin structure (blue) was deduced using the Robetta Server software. The red arrow points to red residues on NCS1 that is the calpain cleavage site.
Figure 3:
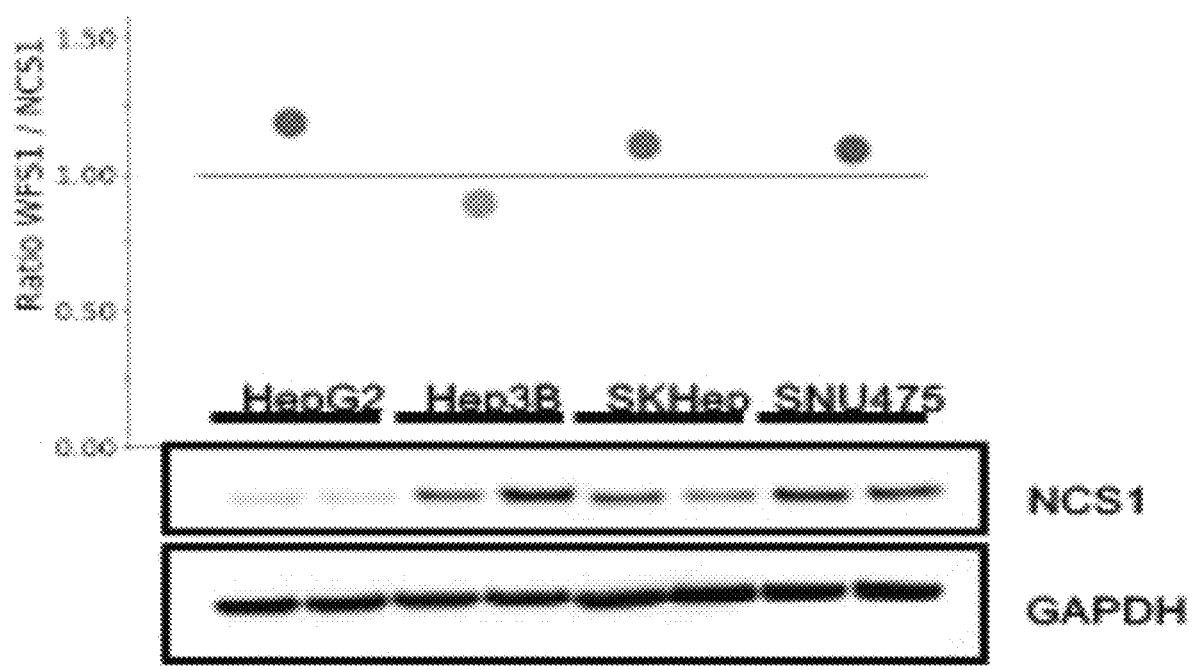
FIG. 3 shows the ratio of WFS1 to NCS1 is constant despite very different levels of NCS1 expression in four different cell lines.
Figure 4:
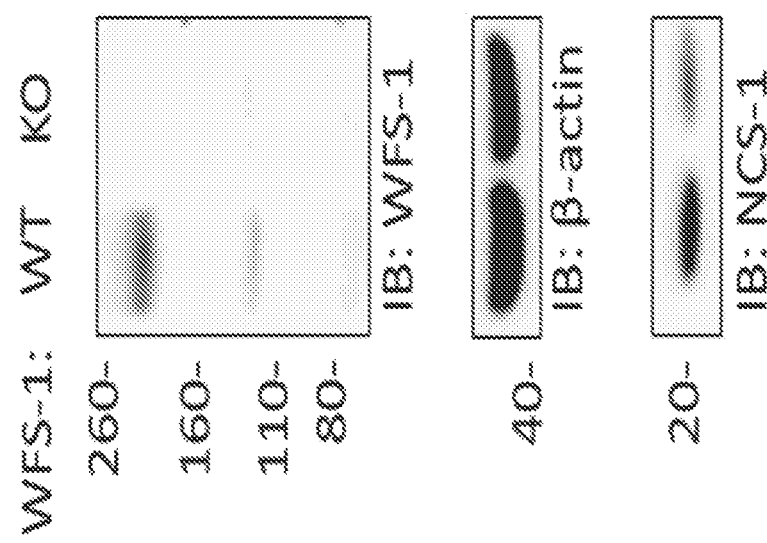
FIG. 4 shows WFS1-KO mouse brain cortex has low NCS1 (right lane) compared to WT tissue. β-actin is shown as a loading control.

Recently, data showed that wolframin interacts directly with NCS1 and it was suggested that this complex is necessary to promote calcium transfer between the ER and mitochondria (4). We tagged the cytoplasmic domain of wolframin to glutathione S-transferase (GST) and showed that NCS1 interacts directly with wolframin in a calcium dependent manner (FIG. 2). From these pull-down experiments we localize binding of NCS1 to the cytoplasmic domain of wolframin (FIG. 2), which is the N-terminal region, residues 1-288. Our in-silico docking experiments using the crystal structure of NCS1 and the structure of wolframin deduced by available software (Robetta Server) are consistent with binding in this region (FIG. 2B). Note that the calpain cleavage site of NCS1 (FIG. 2B, red arrow) appears to be capped by wolframin. Using the Broad Institute cell line information for a separate project, we selected 4 cell lines with different endogenous levels of NCS1. In these cell lines we found that NCS1 and wolframin levels are co-regulated, measured as both mRNA (FIG. 3) and protein levels. In WFS1 patient derived fibroblasts, NCS1 was reduced and resting calcium was reduced (4). NCS1 overexpression in these patient derived cells restored calcium homeostasis and cell functions, measured as mitochondrial respiration (4). To compare with a mouse model of Wolfram syndrome, we examined the levels of wolframin and NCS1 in tissues from WFS1-KO mice. Wolframin was deleted in all tissues examined (brain tissue shown in FIG. 4). As expected from the human cells, NCS1 levels were reduced to at least half of WT levels (FIG. 4). These results provide support for the hypothesis that NCS1 is a component of the pathogenic mechanism for Wolfram syndrome.

Functional Effects of Decreased Wolframin

Figure 5:
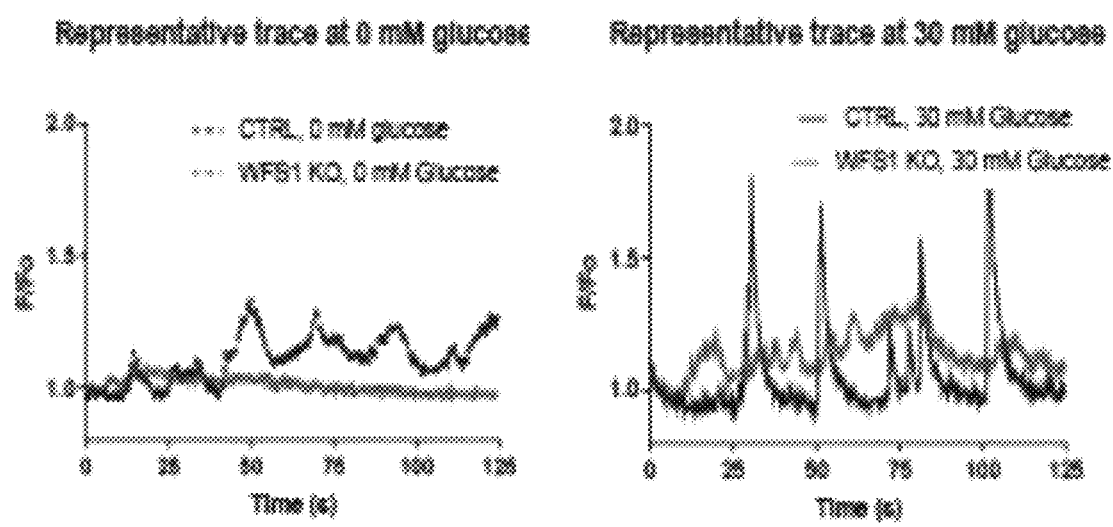
FIG. 5 shows that glucose induces calcium oscillations in INS-1 cells. At low and zero glucose, oscillations are minimal in WT cells and absent in WFS1 KO cells. At 30 mM glucose, WT cells display robust calcium oscillations, but the magnitude and shape of the calcium transients in WFS1 KO Ins1 cells are decreased.
Figure 58:
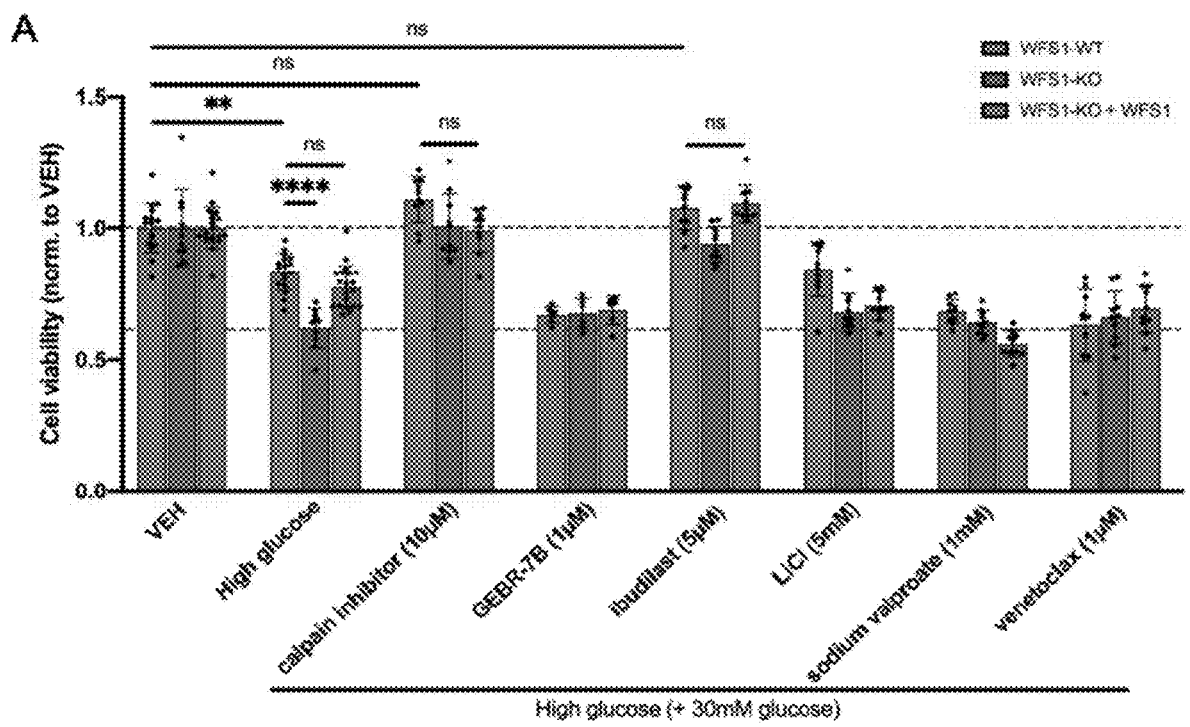

A. Decreased calcium signaling. The addition of glucose stimulates calcium oscillations in INS-1 cells, an insulin-secreting cell line derived from pancreatic tissue (45). This increase in calcium is needed for insulin secretion. Both intracellular calcium release channels and voltage gated calcium channels on the plasma membrane are regulated by NCS1 (7, 24), and both channels are needed to maintain glucose stimulated insulin release (45). INS-1 cells lacking wolframin had a decreased response to the addition of 30 mM glucose, when compared to WT cells. Both the amplitude of each calcium transient and the number of oscillations were diminished (FIG. 5). This blunted response to glucose likely contributes to the decreased insulin secretion, a measure of the pathophysiology of Wolfram syndrome.

Figure 6:
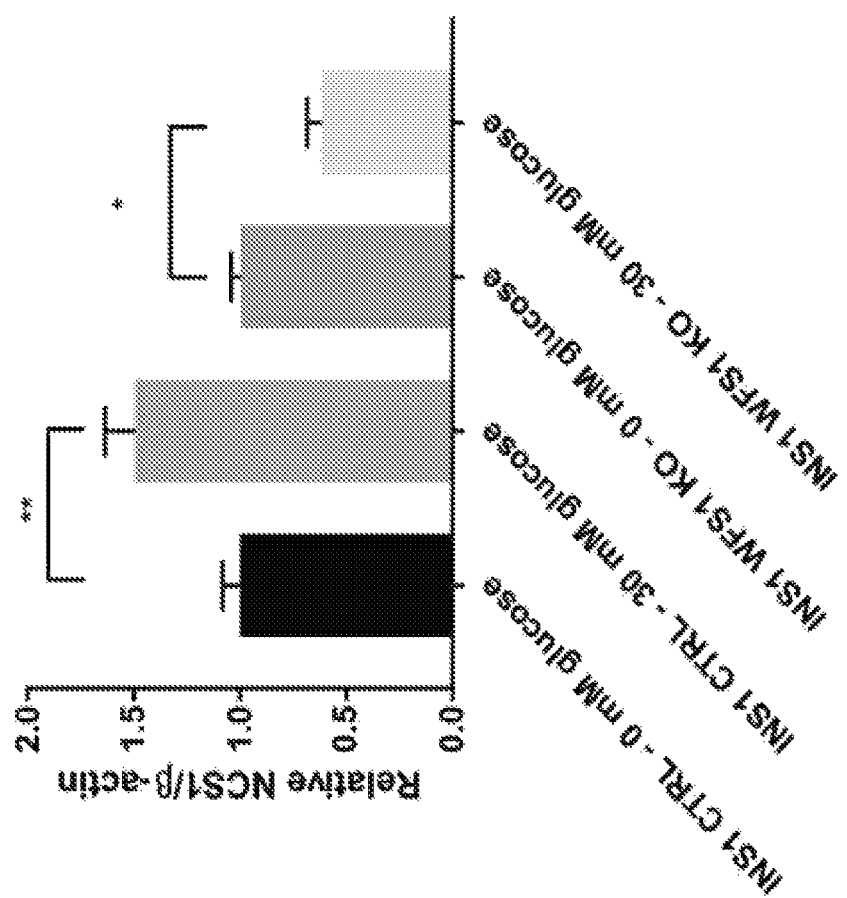
FIG. 6 shows NCS1 levels in INS-1 cells after glucose treatment. Compared to cells treated with 0 mM glucose, NCS1 level was increased in the CTRL cells, but decreased in WFS1 KO cells treated with 30 mM glucose.

B. NCS1 levels change after glucose treatment. INS-1 cells were incubated for 48 hours with 0, 2, or 30 mM glucose. The levels of NCS1 after treatment with 0 or 2 mM glucose were the same in WT and WFS1-KO INS-1 cells. After prolonged exposure to 30 mM glucose. NCS1 was elevated in the WT cells, but decreased in the WFS1-KO cells (FIG. 6). For both cell lines the level of NCS1 was normalized to β-actin so that the percent change is assessed here, rather than the relative level of NCS1 in the WT and NCS1-KO cells. The elevated NCS1 is consistent with our and others studies showing that NCS1 levels are increased with stress (8), presumably to promote cell survival. The lack of elevation of NCS1 in the WFS1-KO cells is consistent with decreased calcium homeostasis and poor survival of pancreatic β-cells.

Figure 7:
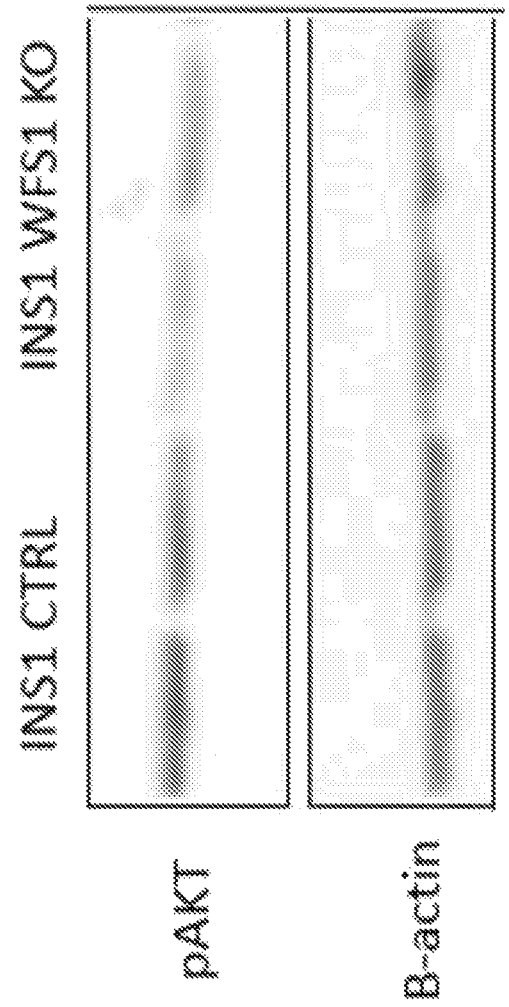
FIG. 7 shows that Wolframin (WFS1) KO decreases phosph-Akt. in INS-1 cells. In the resting state (5 mM glucose) Phosphorylation of AKT (pAKT) was lower than WT.
Figure 8:
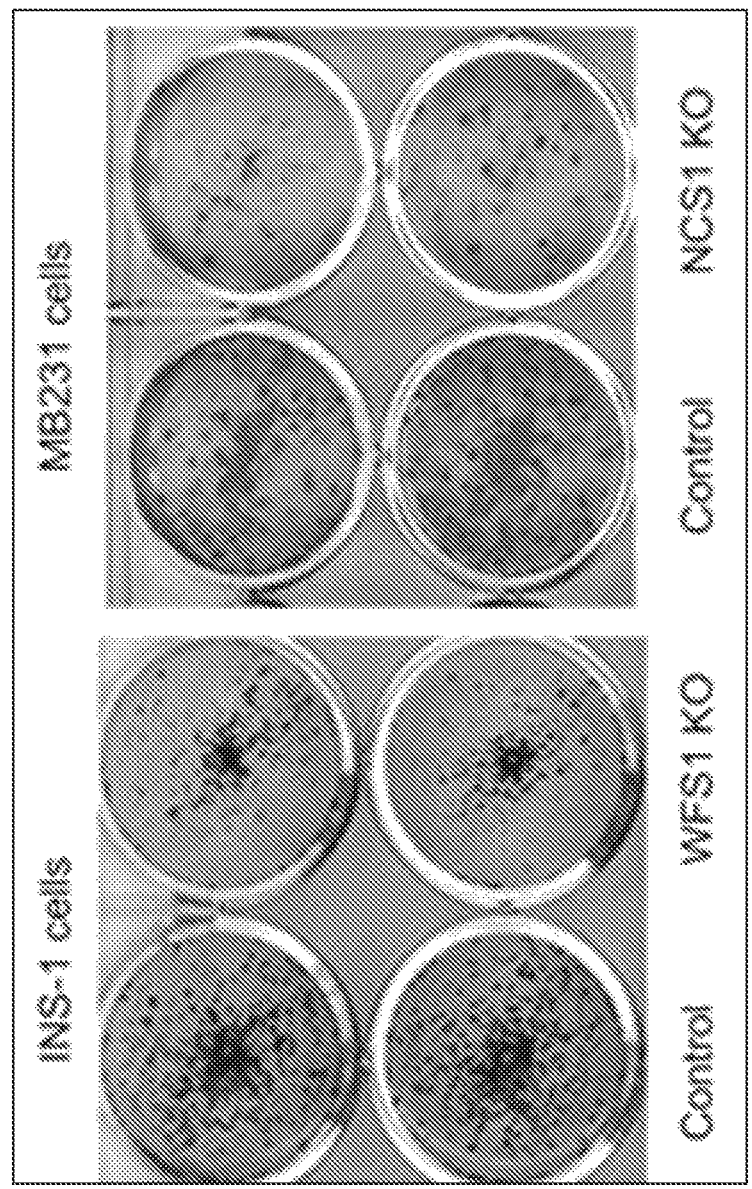
FIG. 8 shows colony formation in wolframin (WFS1, left) or NCS1 (right) KO cells. Cells were plated and maintained in an incubator. After 2 weeks plates were stained and percent coverage by cells were compared. Note that loss of either protein leads to fewer colonies.

C. Changes in pAKT phosphorylation. The level of phosphorylation of AKT was decreased in WFS1-KO INS-1 cells when compared to WT cells (FIG. 7). The decreased pAKT in the WFS1-KO cells is consistent with poor cell survival in Wolfram syndrome.

Figure 9:
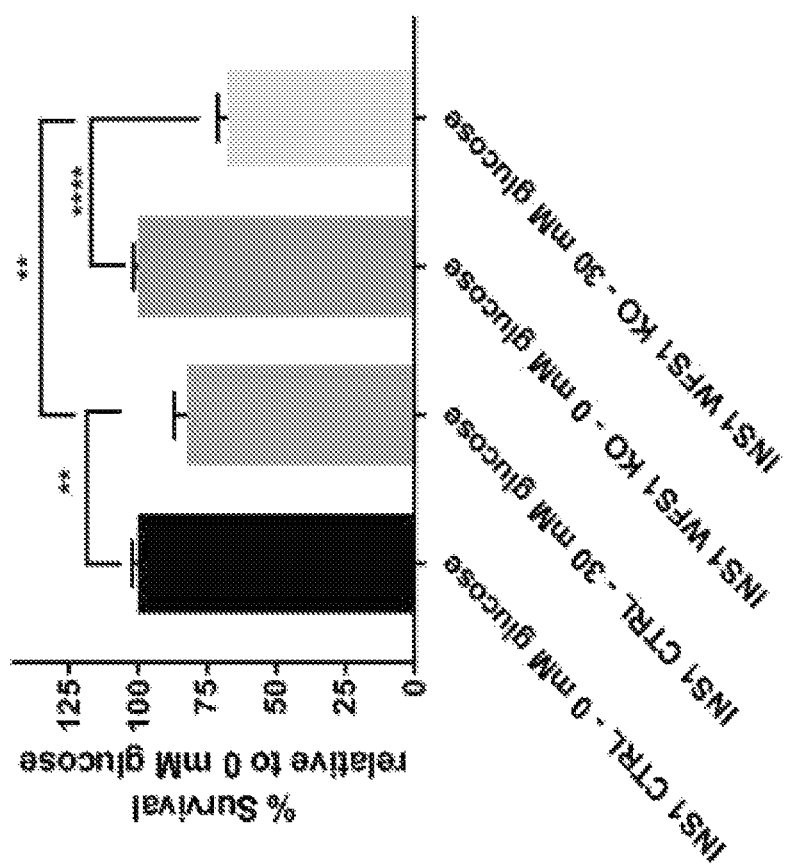
FIG. 9 shows cell survival is diminished in INS-1 cells lacking wolframin (WFS1) after treatment with 30 mM glucose for 48 hours. Survival is normalized to % survival at 0 mM glucose.

Decreased cell survival. The colony formation assay showed that lack of wolframin reduced the number of colonies formed (FIGURE, left panels), as shown using NCS1-KO cells (FIGURE, right panels). Similarly, cell survival is diminished in WFS1-KO cells when compared to WT cells after treatment with 30 mM glucose for 48 hours (FIG. 9)

Figure 10:
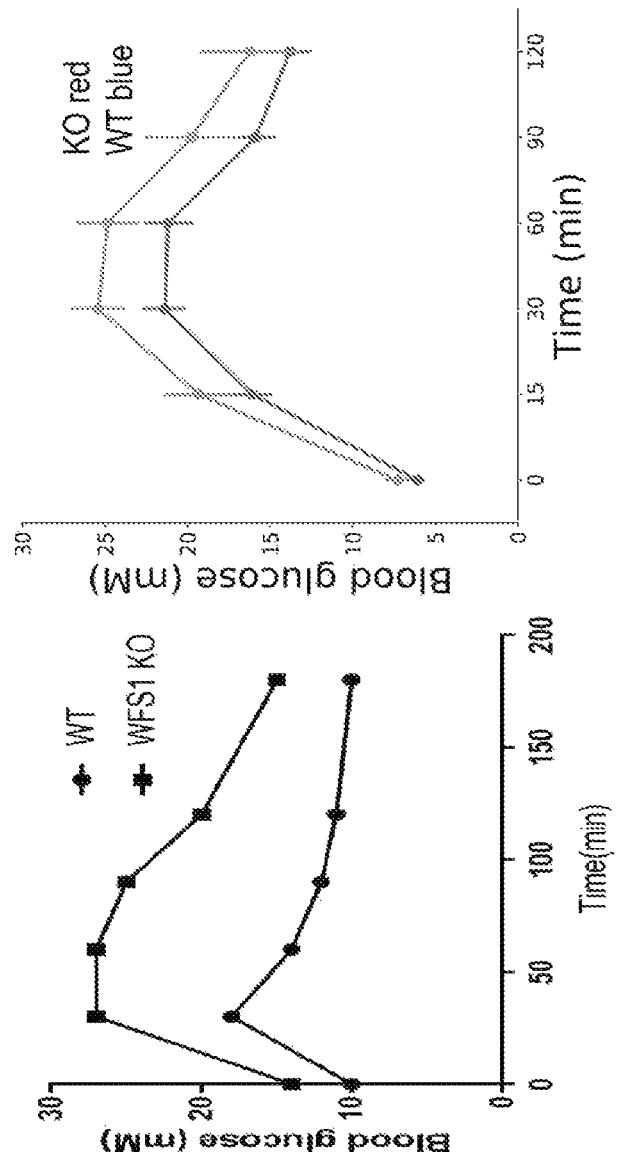
FIG. 10 shows glucose tolerance in WFS1 (left) or NCS1 (right) KO and WT mice. Mice were injected with 2 g glucose and blood samples were collected over time and glucose measured. Note that both WFS1 (left) or NCS1 (right) KO mice achieved higher glucose levels than the WT mice. WFS1 data adapted from reference (49).

Decreased glucose tolerance in mice. After an injection of a bolus of glucose, we found that glucose tolerance was similar in mice lacking either wolframin or NCS1 (FIG. 10). These results show that the two proteins regulate similar metabolic and cellular functions and that protecting NCS1 levels may compensate for the diminished functions associated with loss of wolframin activity in Wolfram syndrome.

Pharmacological Interventions

Figure 11:
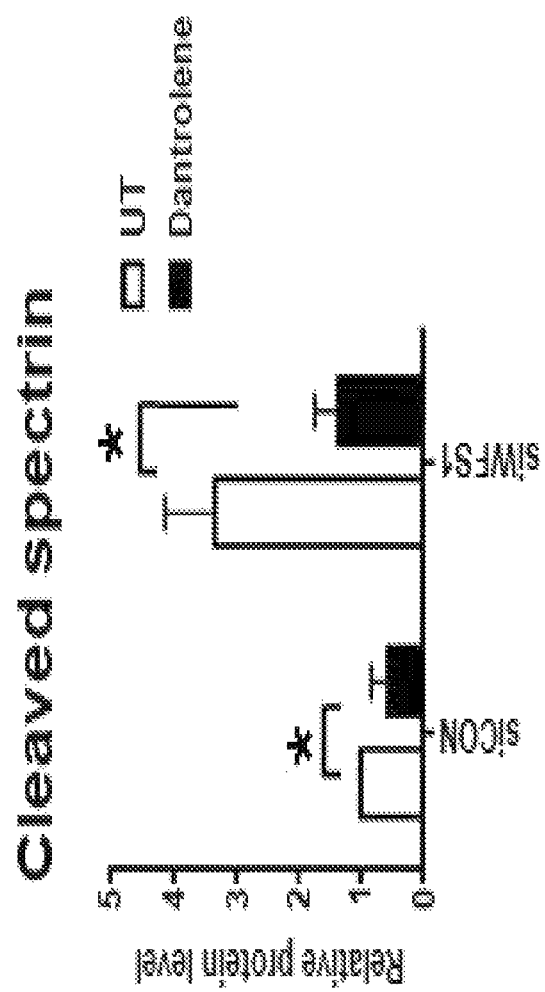
FIG. 11 shows that INS-1 cells were transfected with scrambled siRNA or siRNA against WFS1, pretreated with or without 10 μM dantrolene for 48 h, then incubated in media containing 0.5 μM thapsigargin for 6 h. Thapsigargin treatment induces cell stress. Protein levels of cleaved spectrin were analyzed by immunoblotting and quantitated relative to GAPDH levels. Taken from (56).

The pathway leading to calpain activation provides potential therapeutic targets for Wolfram syndrome. To test this concept, my collaborator Dr. F. Urano (Washington University, St. Louis) performed a small-scale screen to identify chemical compounds. The first compounds that my collaborator tested is dantrolene. This drug is a FDA-approved drug clinically used for malignant hyperthermia (54) and is an inhibitor of the ER-localized ryanodine receptors which will suppress leakage of calcium from the ER (55). Dantrolene restored cytosolic calcium levels in WFS1-deficient cells, suppressed apoptosis (56) and reduced calpain activity in INS-1 cells (FIG. 11) and in brain lysates from WFS1-KO mice (57). These results support the hypothesis that inhibition of calpain activation would help slow the progression of Wolfram syndrome. However, dantrolene has side effects of prolonged use, primarily liver toxicity. Because of these long term effects, new, less toxic compounds are needed to treat Wolfram syndrome.

Calpain antagonists (eg, AK295, calpastatin) also have been tested as a treatment in several human diseases (79). However, direct calpain antagonists are not appropriate as a therapeutic for human subjects because calpains are ubiquitous and necessary for survival. That is, the side effects of inhibition of calpains are worse than the disease to be treated.

Figure 12:
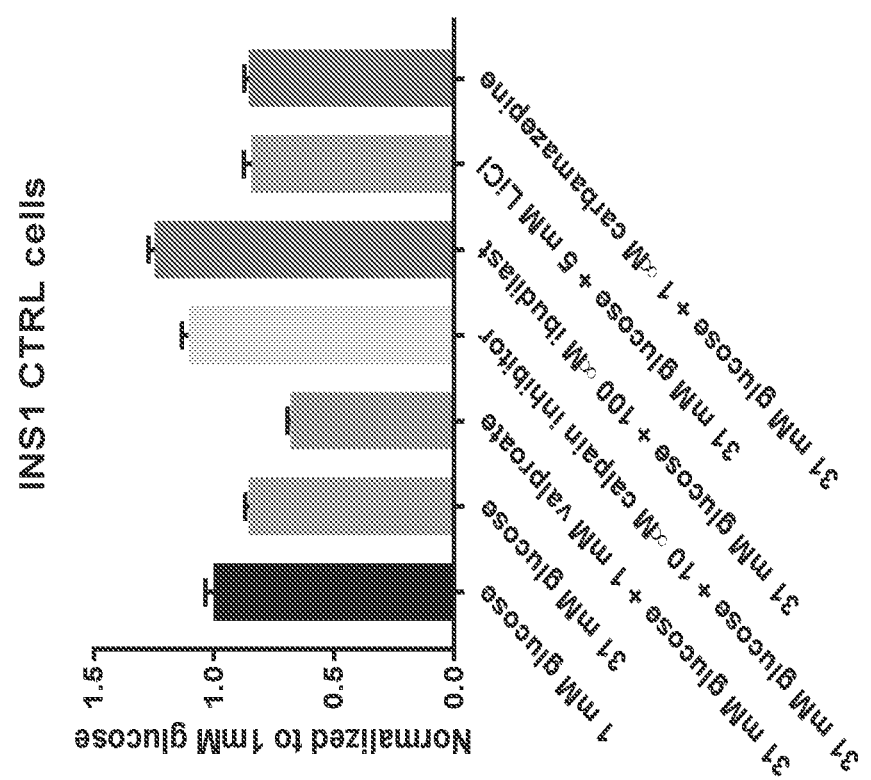
FIG. 12 shows the cell survival (WT) after treatment with 31 mM glucose for 48 hours. Treatment with valproate, lithium, or chlorprmazine had no effect on survival, but calpain inhibitor or ibudilast did. Survival is normalized to % survival at 1 mM glucose.
Figure 13:
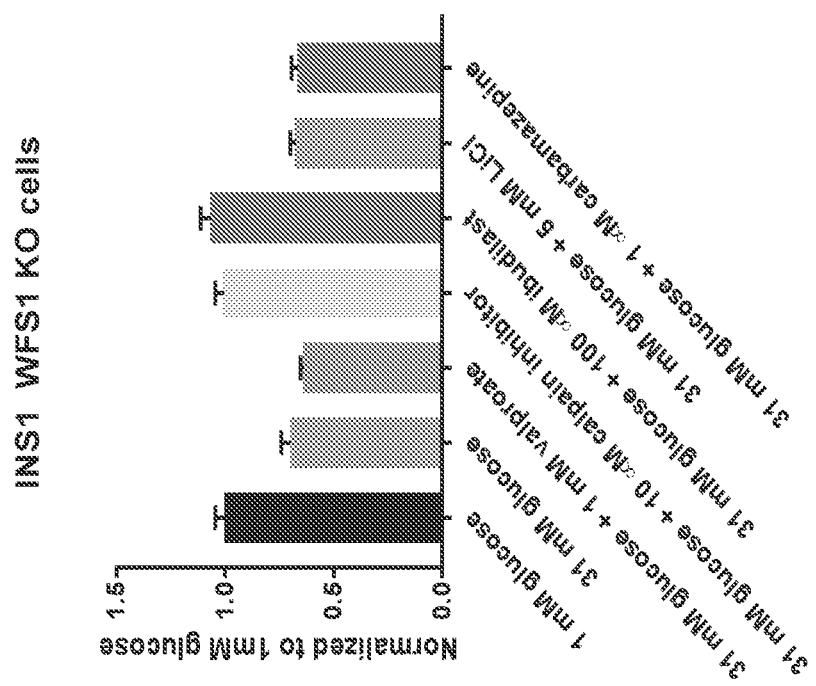
FIG. 13 shows cell survival (WFS1 KO) after treatment with 31 mM glucose for 48 hours. Treatment with valproate, lithium, or chlorprmazine had no effect on survival, but calpain inhibitor or ibudilast did. Survival is normalized to % survival at 1 mM glucose.
Figure 14:
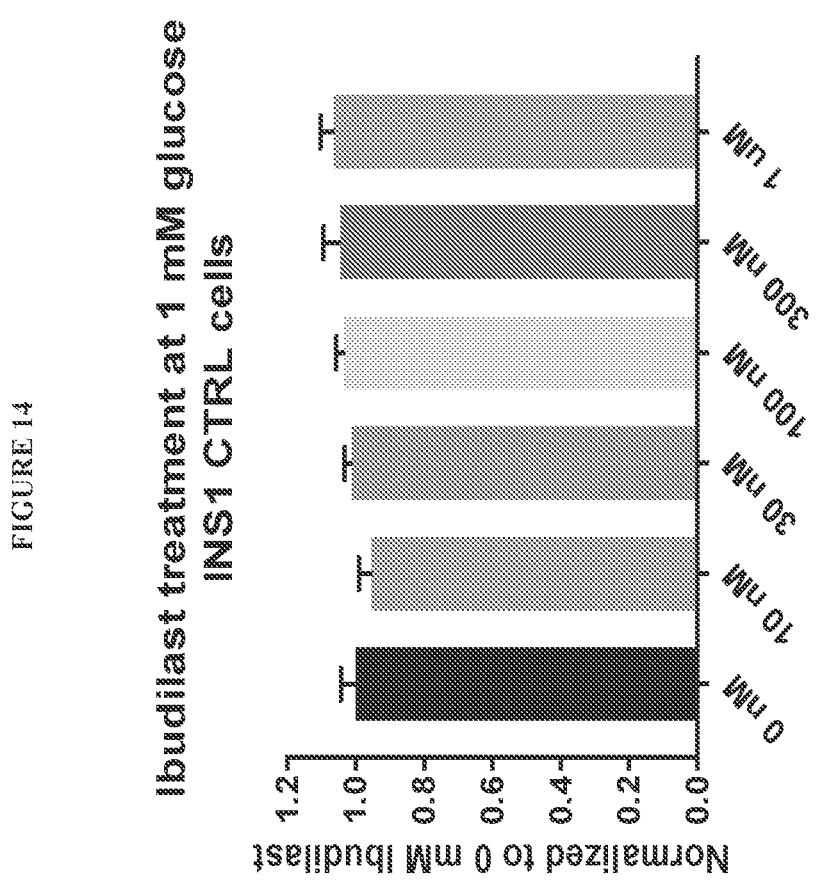
FIG. 14 shows that treatment with ibudilast does not alter cell survival (WT) at low ("normal") glucose levels.
Figure 15:
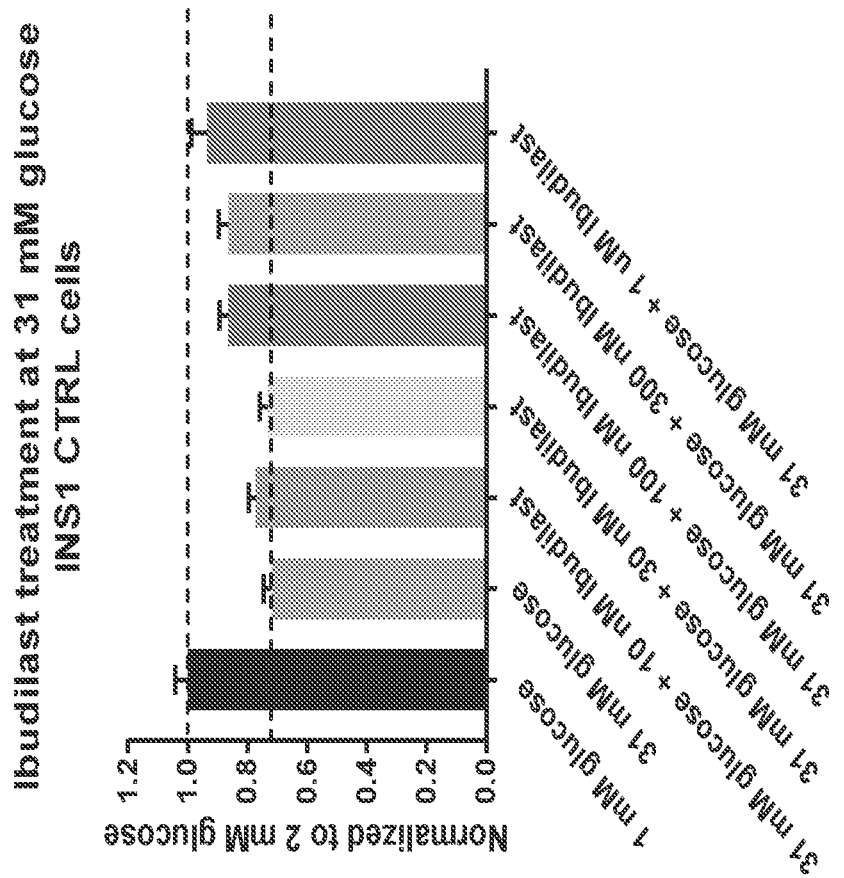
FIG. 15 shows that cell survival (WT) after treatment with 31 mM glucose for 48 hours is decreased. Treatment with ibudilast did protect cell survival. Nearly full protection occurs at 1 uM ibudilast. Survival is normalized to % survival at 1 mM glucose.

The inventor tested drugs known to maintain NCS1-dependent expression and signaling (valproic acid, ibudilast, lithium, chlorpromazine) and calpain inhibitors (AK295). We found that valproic acid, lithium, and chlorpromazine had no effect on glucose induced cell death in WT (FIG. 12) and WFS1 KO cells (FIG. 13). In contrast, ibudilast and the calpain inhibitor rescued viability at high glucose concentration in WT (FIG. 12) and WFS1 KO cells (FIG. 13). Ibudilast had no effect on cell survival in 1 mM glucose, the normal level of glucose (FIG. 14). The half max effect on survival occurred at approximately 300 nM, with nearly full recovery at 1 uM ibudilast (FIG. 15). The concentration range for protection from cell death by high glucose in WFS1 KO cells is similar.

Examples Second Set

Materials and Methods:
Reagents

All chemicals used were obtained from Sigma-Aldrich unless stated otherwise. Calpain inhibitor XI was purchased from Calbiochem, ibudilast from Cayman Chemical Company, and ATP from AmericanBio. Stock of drugs was prepared in 100% DMSO (AmericaBio), aliquoted, and stored at −20° C. For treatment, stock concentrations were diluted in cell medium and DMSO concentration was kept below 0.1% in all experiments.

Generation of Stable Cell Lines and Cell Culturing

The WFS1-KO INS1 832/13 lines were generated by the Genome Engineering and iPSC Center (GEiC) at the Washington University in St. Louis. Briefly, gRNAs were designed to target an early exon that is common to all transcription isoforms, cloned under a U6 promoter and validated for cleavage activity in K562 cells by cotransfecting with a plasmid expressing Cas9 under the CMV promoter (CMV-Cas9-NLS-HA). The most active gRNA (5'-gctgctggagaatgtcgggcagg) construct was then cotransfected with the Cas9 plasmid to INS1 cells using the nucleofection method in solution P3 and the program DS-150, following Lonza's instructions. Transfected pool was genotyped to confirm presence of editing at the target site before it was single cell sorted into 96-well plates. Clones grown from the sorted plates were genotyped at the target site to identify those carrying out-of-frame indels in all alleles. Then positive clones were expanded. Genotype was confirmed when cells were transferred from a 6-well to a T75. A frozen vial was then test thawed to confirm good survival, and the culture was tested for mycoplasma contamination before delivery. WFS1-OE cells were generated by transfecting WFS1-KO clone #1 cells with a pcDNA3.1 plasmid carrying the full-length WFS1 sequence (Addgene, #13011) using Lipofectamine 2000 (Thermo Fisher), followed by 4 weeks of antibiotic selection with 2 mg/mL G418 (AmericanBio). WFS1-WT and WFS1-KO cells stably expressing mito-gCaMP6F (a gift from D. Stefani, University of Padua) were generated by transfection with mito-gCaMP6F using Lipofectamine 2000. GFP-positive cells were subsequently collected using fluorescence-activated cell sorting (FACS). NCS1-OE and empty vector control cells were generated by transfecting WFS1-KO clone #1 cells with a pIRES2-EGFP plasmid (a gift from E. Gracheva, Yale University) with or without full-length NCS1 sequence using Lipofectamine 2000, then collected using FACS. All INS1 cell lines were maintained at 37° C., 5% $CO_2$, in RPMI 1640 supplemented with 10% FBS, 1% HEPES, 1% sodium pyruvate, 50 μM β-mercaptoethanol, and 1% penicillin/streptomycin (Gibco). Cell medium for WFS1-OE, mito-gCaMP6F, NCS1-OE, and the empty vector control was additionally supplemented with 1 mg/mL G418 for maintenance.

Calcium Imaging $2 \times 10^5$ cells were plated on each coverslip 2 days before imaging in INS1 medium without G418. HEPES-buffered saline (140 mM NaCl. 1.13 mM $MgCl_2$, 4.7 mM KCL, 2 mM $CaCl_2$, 10 mM D-glucose, and 10 mM HEPES, adjusted to pH 7.4 with NaOH) was used to prepare calcium dye solution and during imaging. In calcium-free HEPES buffer, $CaCl_2$ was replaced with $MgCl_2$ and 0.1 mM EGTA was added to chelate calcium. Fura-2-AM dye powder (Thermo Fisher) was dissolved to 4 μM in calcium-containing HEPES buffer supplemented with 0.03% Pluronic acid (Thermo Fisher). On the day of imaging, each coverslip was incubated in dye solution for 45 min in the dark at room temperature. Each coverslip was then washed 3 times in HEPES-buffered saline solution before calcium imaging began. Calcium measurements were performed with a Hammamatsu Orca R2 camera attached to a Zeiss microscope with a Sutter Lambda DG4 for excitation ratio imaging. Cells were imaged using sequential excitation at 340/380 nm (Fura-2-AM). Images were acquired with emission bandwidth of 501 to 550 nm every second. The raw 340 and 380 signals for each cell were subtracted by corresponding background signal before a 340/380 ratio was calculated. Max amplitude and area under the curve were calculated using PRISM Statistical Software 8. Rate of rise was quantified as the gradient between 25% and 75% maximum amplitude. All experiments were conducted at room temperature. For calcium imaging at varying glucose concentrations, glucose concentration was maintained throughout the dye and imaging solutions.

For mitochondrial calcium imaging, cells stably expressing mito-gCaMP6F were prepared on coverslips as described above. 2 days after, cells were imaged using sequential excitation at 488 nm, and images were acquired with emission bandwidth of 501 to 555 nm. The experiment was carried out and analyzed similarly to cytosolic calcium recordings, except that after background subtraction, data were normalized to the first 10 s (baseline recording). All figures depicting calcium imaging traces show the average of 8-24 coverslips, each with 40-70 cells, from at least 3 independent recordings.

Western Blot

Cultured cells were lysed in mammalian protein extraction reagent (MPER, Thermo Fisher) and mouse brains were lysed in radioimmunoprecipitation assay (RIPA) buffer containing SDS (Santa Cruz). Both MPER and RIPA were supplemented with Halt protease and phosphatase inhibitor cocktail (Thermo Fisher). After spinning down at 13,000 rpm for 20 min at 4° C. to clear cell lysate, the protein concentration was measured with the bicinchoninic acid assay (Thermo Fisher). Equal amounts of protein were loaded, and electrophoresis was performed in NuPAGE 4-12% gradient bis-tris polyacrylamide protein gels (Thermo Fisher). Proteins were transferred to a PVDF membrane and blocked with 5% milk in phosphate-buffered saline with 0.1% Tween-20 for 1 hour. Membranes were then incubated overnight with primary antibodies (see list of primary antibodies in SI Appendix, Table S1, below) at 4° C. Blots were washed and incubated with secondary antibody for 2 h at room temperature. After washing, the secondary antibody was visualized by Pierce ECL chemiluminescence reagents (Thermo Fisher) or using a LI-COR Odyssey imaging system (L1-COR Biosciences).

Co-Immunoprecipitation

500 μL of 1 μg/μL mouse brain lysate (in RIPA with protease and phosphatase inhibitor) was incubated with 10 μL of NCS1 antibody (FL190, Santa Cruz) or 10 μL of rabbit IgG overnight at 4° C., followed by incubation with 30 μL of Pierce™ protein A/G magnetic beads (Thermo) for 2 h at 4° C. Incubated beads were washed 3 times with cold phosphate buffered saline (PBS) (American Bio), and then eluted by boiling with 20 μL of loading buffer. The eluted fractions were then analyzed via Western blot.

Cell Viability Assay

CellTiter-Glo™ (CTG) assay (Promega) was used to quantify ATP-dependent bioluminescence as an indicator of cell viability. To assess cell viability, INS1 cells were plated in white 96-well plates (Cat. 07-200-628, Fisher Scientific) at a density of $2\times10^3$ cells per well and treated the following day with high glucose and/or the indicated drugs for 48 hours before imaging. After treatment was completed, 100 μL of CTG solution was added to each well and 20 minutes later, reading was performed using a Tecan Infinite M1000 Pro microplate reader using the following setting: 5 s orbital shaking (3 mm, 216 rpm), followed by imaging in luminescence mode with 500 ms integration time.

Calpain Activity Assay

Calpain-Glo™ protease assay (Promega) was used to quantify calpain activity. $1\times10^6$ cells were plated per well on a 12-well plate. 24 h later, cells were lysed in cytobuster (Novagen). Protein concentration was quantified using BCA assay. Calpain assay was carried out on a white 96-well plate in a 100 μl reaction set up. Per well, 25 μg protein were diluted in 50 μl of cytobuster. 50 μl of pure cytobuster was used as a negative control, and 50 μl of cytobuster with 2 mM $CaCl_2$ and 1 μl pure calpain-2 was used as a positive control. Finally, 50 μl of Calpain-Glo solution were added per well and 30 minutes later, reading was done using a Tecan Infinite M1000 Pro microplate reader with the same setting as described for the CTG assay.

Insulin Secretion Assay

For glucose-stimulated insulin secretion studies, INS1 cells were plated on 6-well plates at a density of $6\times10^5$ cells per well. After 24 hours, cells were incubated with drugs for another 24 hours. Two days after plating, the insulin ELISA assays were performed following a previously published protocol [79]. In detail, preincubating cells in DMEM-base (Sigma) supplemented with 2.5 mM glucose for 1.5 h was followed by a 45 min incubation in DMEM-base with either 2.5 mM glucose for basal secretion or 9 mM glucose for stimulated secretion as indicated. 200 μl of supernatant were collected for analysis of insulin concentration using the Rat High Range ELISA kit (80-INSRTH-E01, ALPCO). Cells were washed with ice cold PBS and lysed in 1 mL 0.1% Triton X-100. Insulin levels were normalized to total protein measured by Micro BCA protein assay kit (23235, Thermo Fisher Scientific).

Data Analysis

Data management and calculations were performed using PRISM Statistical Software 7. For comparison between two groups, unpaired, two-tailed student t-test was carried out. For comparison of more than two groups, one-way analysis of variance (ANOVA), followed by Tukey's post hoc test, was performed. A p-value<0.05 was considered to be statistically significant and the following notations were used in all figures: * for p<0.05,  for p<0.01, * for p<0.001, and **** for p<0.0001. All error bars shown are standard deviation (SD). Detailed results of statistical analyses were included in the SI Appendix, Table S2.

Overview

Wolfram syndrome is an orphan, autosomal recessive genetic disorder that affects about 1 in 500,000 people worldwide and is characterized by diabetes insipidus, diabetes mellitus, optic nerve atrophy, and deafness (therefore also known by the acronym "DIDMOAD") [1]. Typically, a progressive childhood-onset of non-autoimmune, insulin-dependent diabetes mellitus is the first diagnosed symptom at around age 6 [2]. There is currently no disease-modifying treatment for Wolfram syndrome, and patients usually die in mid-adulthood [3]. Up to 90% of cases can be attributed to pathogenic variants in the Wolfram syndrome 1 (WFS1) gene, which encodes for the protein wolframin (WFS1) [4]. The remaining cases are due to mutations in the CISD2 gene (a.k.a. WFS2) or other unknown genes [2]. Heterozygous carriers of WFS1 sequence variants make up around 1% of the world's population and are at enhanced risk of psychiatric disorders and hearing loss [5-7]. WFS1 is a transmembrane protein and appears to localize to the endoplasmic reticulum (ER) [8]. It is expressed in most tissues, but at higher levels in the brain, heart, lung, and pancreas. Although the endogenous functions of WFS1 remain unclear, several recent studies suggest that WFS1 regulates ER stress [9, 10], mitochondrial health [11], and calcium homeostasis [12-14].

This study further investigates how WFS1 regulates calcium homeostasis in the context of diabetes mellitus. Calcium is a universal second messenger and its concentration in the different cellular compartments has to be tightly regulated for proper cell functions [15]. In particular, intact calcium homeostasis is integral to the survival of [16, 17] and insulin secretion from pancreatic β-cells [18-20]. Additionally, dysregulation of calcium signaling has been proposed as a mechanism of many diseases such as Alzheimer's disease [21], cancer progression [22], and diabetes mellitus [23, 24].

Here, we showed that knocking-out (KO) WFS1 in rat insulinoma (INS1) cells led to elevated resting cytosolic calcium, reduced stimulus-evoked calcium signaling and consequently, to hypersusceptibility to hyperglycemia and decreased glucose-stimulated insulin secretion. Overexpressing WFS1 or WFS1's interacting partner neuronal calcium sensor-1 (NCS1) reversed the deficits observed in cells lacking WFS1. Moreover, calpain inhibitor XI and ibudilast rescued resting cytosolic calcium, cell viability, and insulin secretion in WFS1-KO cells. These findings further our understanding of Wolfram syndrome and other diseases caused by impaired calcium homeostasis.

Results:

Loss of WFS1 Disrupts Cellular Calcium Homeostasis

Several studies have implicated a role for WFS1 in regulating calcium homeostasis, including resting cytosolic calcium [11, 13], ER calcium storage [12], and agonist-induced ER calcium release [11, 14]. To study the effects of WFS1 depletion on calcium homeostasis in pancreatic β-cells, we compared stable INS1 832/13 rat insulinoma cell lines with normal expression (WFS1-WT) or loss of WFS1 (WFS1-KO). Two WFS1-KO clones were created using clustered regularly interspaced short palindromic repeats (CRISPR) with a gRNA targeting an early, conserved exon (SI Appendix, FIG. 1S). All experimental results shown were obtained from WFS1-KO clone #1, and key findings were validated in WFS1-KO clone #2 (SI Appendix, FIG. 3S). WFS1-WT cell line was obtained from a clone with no CRISPR modification in the same preparation. We also generated stable WFS1-overexpressing (WFS1-OE) cells on the WFS1-KO background for validation experiments. Loss of WFS1 in WFS1-KO cells as well as the successful re-expression of WFS1 was verified using Western blot (FIG. 16A). To confirm a previous observation that INS1 cells with reduced WFS1 expression show higher resting cytosolic calcium [13], we measured resting cytosolic calcium in both cell lines using the ratiometric, cytosolic calcium dye Fura-2-AM. As expected, WFS1-KO cells showed an elevation in resting cytosolic calcium at baseline compared to WFS1-WT cells, which was normalized by re-expressing WFS1 (FIG. 16B). Similar results were obtained using the non-ratiometric, cytosolic calcium dye Fluo-4-AM (SI Appendix. FIG. 2SA). We also found that calpain activity was elevated in WFS1-KO cells (FIG. 16C), suggesting that our WFS1-KO cells recapitulate the deficits observed in an earlier WFS1-knockdown cell model [13].

WFS1-KO cells show decreased InsP3R-dependent ER calcium release. Because the loss of WFS1 expression has been linked to increased ER stress [9, 10] and reduced ER calcium release [11, 14], we next investigated agonist-induced calcium release from the ER in WFS1-WT and WFS1-KO cells. To measure ER calcium release via the inositol 1,4,5-trisphosphate-receptor (InsP3R), we used adenosine triphosphate (ATP) as the agonist for cells in calcium-free buffer. Measurements with Fura-2-AM dye showed that WFS1-KO cells showed reduced ATP-induced InsP3R-dependent ER calcium release into the cytosol (FIG. 16D). Compared to the WFS1-WT cells, WFS1-KO cells exhibited a significant reduction in the max amplitude, area under the curve, and rate of rise (FIGS. 16E-G). Similar observations were made when cells were loaded with Fluo-4-AM dye (SI Appendix, FIGS. 2SE-H). Reintroducing WFS1 into WFS1-KO cells fully rescued the max amplitude and rate of rise (FIGS. 16E-G), and partially rescued the area under the curve (FIG. 16F). Several effects of the loss of WFS1 on ER calcium filling have been described in different cell lines [12, 14]. In INS1 cells, ER calcium loading, as assessed by treatment with 1 μM thapsigargin, was not altered following the loss of WFS1 (SI Appendix, FIGS. 2SB-D). Furthermore, the protein expressions of InsP3R1 and InsP3R3 were not different between WFS1-WT and WFS1-KO cells (SI Appendix, FIGS. 2SI-K).

WFS1-KO cells show decreased ER-mitochondrial calcium transfer. The ER releases calcium via the InsP3R not only into the cytosol but also into mitochondria at specialized interorganellar junctions called mitochondria-associated ER membranes (MAM) [25]. Dysregulations of the MAM have been implicated in Alzheimer's disease [26], diabetes mellitus [27, 28] and Wolfram syndrome [14]. Therefore, we hypothesized that reduced cytosolic InsP3R-dependent calcium transients (FIGS. 16D-G) would be correlated with a reduction in mitochondrial calcium uptake in WFS1-KO cells. As expected, mitochondrial calcium uptake, as measured with the calcium sensor mito-gCaMP6F, was significantly smaller in WFS1-KO cells after stimulation with ATP (FIG. 16 H-K). Using two independent cellular fractionation protocols, we found that WFS1 was present in the crude mitochondrial fraction, which contains MAM proteins (SI Appendix, FIGS. 2SL-M). This observation is consistent with several previously published proteomic analyses of the MAM structure [29-31], supporting that WFS1 plays a role at the MAM.

WFS1-KO Cells Show More Severely Impaired Calcium Signaling Due to Hyperglycemia Chronic hyperglycemia, or glucose toxicity, is a hallmark of diabetes mellitus and impairs β-cell physiology, particularly intracellular calcium signaling [18, 32-34]. To mimic glucose toxicity in Wolfram syndrome, we treated both WFS1-WT and WFS1-KO cells with an additional 30 mM glucose for 24 h before calcium imaging was performed. In the high glucose environment, resting cytosolic calcium in WFS1-WT cells rose significantly to a level comparable to WFS1-KO cells at baseline (FIG. 17A). In contrast, resting cytosolic calcium in WFS1-KO cells treated with extra glucose remained at the same level as in untreated WFS1-KO cells, suggesting that untreated WFS1-KO cells already achieved a maximal resting cytosolic calcium. In response to increasing glucose concentrations (+0, 15, or 30 mM glucose for 24 h), both WFS1-WT and WFS1-KO cells showed a concentration-dependent reduction in ATP-evoked ER-calcium release into the cytosol (FIG. 17B). Nevertheless, WFS1-KO cells showed a lower calcium response at 0 mm and 15 mM additional glucose compared to WFS1-WT cells at the same concentrations. The response for both cell lines converged to a minimal level at the highest glucose concentration. Further analyses of max amplitude, area under the curve, and rate of rise suggested that WFS1-KO cells at baseline showed an ATP-response similar to WFS1-WT cells treated with 15 mM glucose, and WFS1-KO cells treated with 15 mM showed a similar response to WFS1-WT cells treated with 30 mM glucose (FIGS. 17C-E). These observations indicate that at baseline, WFS1-KO cells already show defects in calcium signaling comparable to WFS1-WT cells under diabetic hyperglycemia, which may result in an acceleration of functional impairments following hyperglycemia in WFS1-KO cells.

Figure 18:
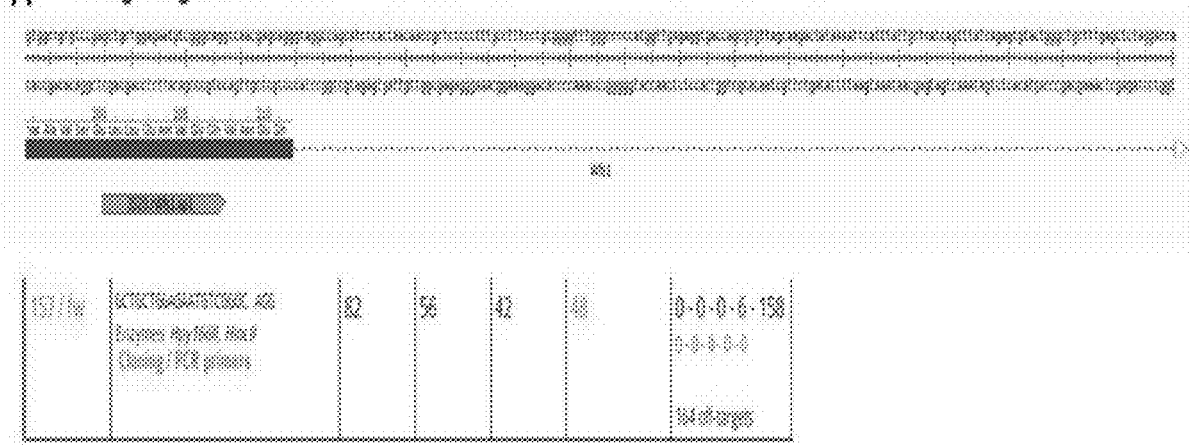
FIG. 18 shows that overexpression of WFS1's interacting partner NCS1 rescues calcium homeostasis in WFS1-KO cells. (A) For co-immunoprecipitation, mouse brain lysate was incubated with NCS1 antibody or rabbit IgG as control. Immunoblots were incubated with antibodies as indicated. (B) Representative blot showing protein abundance of NCS1 in WFS1-WT and WFS1-KO cells treated for 48 h with additional 30 mM glucose (30G). (C) Quantification of B (10-12 independent preparations for each condition), values normalized to CTRL. Whereas WFS1-WT cells showed an increase in NCS1 level, WFS1-KO cells showe++d a decrease. (D) Western blot confirming the overexpression of NCS1 in WFS1-KO cells. (E) Panel shows averaged traces of 9-32 coverslips for each cell type in response to 50 nM ATP. Overexpression of NCS1 rescued ATP-evoked cytosolic calcium response in WFS1-KO cells. (F-I) Quantification of max amplitude, area under the curve, and rate of rise for the cytosolic calcium traces shown in E. (I) Overexpression of NCS1 rescued elevated resting cytosolic calcium in WFS1-KO cells.

Overexpression of WFS1's Interacting Partner NCS1 Rescues Calcium Homeostasis in WFS1-KO Cells Neuronal calcium sensor-1 (NCS1) is a regulator of calcium-dependent signaling pathways [35], such as survival [36] and insulin secretion [37], and was recently implicated in the disease mechanism of Wolfram syndrome in fibroblasts [14]. WFS1 and NCS1 were reported to interact, which we corroborated with co-immunoprecipitation experiments (FIG. 18A). Unlike the previous observation in fibroblasts, we saw no difference in NCS1 protein expression between INS1 WFS1-WT and WFS1-KO cells, suggesting tissue-specific regulation (SI Appendix, FIGS. 4SA-B). As several studies reported that NCS1 protein expression was increased in response to cell stress [36, 38], we assessed NCS1 protein expression following hyperglycemia. We found that glucose toxicity led to an approximately 1.5-fold increase in NCS1 protein expression in WFS1-WT cells after 48 hours (FIGS. 18B-C). In contrast, in WFS1-KO cells, a significant decrease in NCS1 protein expression was observed (FIGS. 18B-C). NCS1 mRNA level was not changed between the different conditions (SI Appendix, FIG. 4SC), indicating that WFS1 likely regulates NCS1 protein levels post-transcriptionally. Next, we overexpressed NCS1 in WFS1-KO cells and showed that NCS1 fully rescued both the ATP-evoked cytosolic calcium release (FIGS. 18E-H) and the resting cytosolic calcium (FIG. 18I). Overexpressing the empty vector with a green fluorescence protein (GFP) marker alone did not affect calcium response in WFS1-KO cells, suggesting that neither the transfection process nor the GFP signal interfered with our measurement. Consistent with a previous study [14], these results indicate that NCS1 plays a role in the disease mechanism of Wolfram syndrome and that NCS1 is a potential target for treatment, as previously described in other conditions [39, 40].

Calpain Inhibitor XI and Ibudilast Rescue Cell Viability and Resting Cytosolic Calcium in WFS1-KO Cells Because intracellular calcium is an important determinant of cell viability, we measured cell viability in WFS1-WT and WFS1-KO cells. A luminescent, ATP-based assay was used. First, we established that knocking-out WFS1 in INS1 cells did not reduce cell viability at baseline (FIG. 19A) or proliferation over one week (FIG. 19B). Following hyperglycemia (additional 30 mM glucose for 48 h), we observed an approximately 40% reduction in cell viability in WFS1-KO cells, whereas cell viability in WFS1-WT cells was only 15% lower than under control conditions (FIG. 19C). WFS1-KO cells could be rescued by WFS1 re-expression (SI Appendix, FIG. S5A). These findings are supported by previous reports showing that WFS1 deficiency causes progressive loss of pancreatic β-cells [41, 42].

Calpain inhibitor and ibudilast rescue cell viability in WFS1-KO cells. In order to reverse hyperglycemia-induced loss of cell viability pharmacologically, 6 different compounds previously shown to affect calcium homeostasis and WFS1- or NCS1-dependent processes were tested in WFS1-WT, WFS1-KO and WFS1-OE cells (SI Appendix. FIG. 5SA). Two compounds, calpain inhibitor XI and ibudilast, fully rescued cell viability back to baseline in all three cell lines. Subsequently, we showed that calpain inhibitor XI and ibudilast did not significantly affect cell viability at baseline (FIG. 19C) and reversed glucose toxicity-induced loss of cell viability in a dose-dependent manner in WFS1-KO cells (SI Appendix, FIGS. 5SB-E). Calpain inhibitor XI is a potent, highly selective, reversible, and active site inhibitor of calpain-1 and -2 [43]. Ibudilast was developed as a phosphodiesterase 4 (PDE4) inhibitor and is approved for the treatment of patients with asthma and post-stroke dizziness in Japan 1441.

Calpain inhibitor and ibudilast rescue resting cytosolic calcium in WFS1-KO cells. To investigate a possible mechanism of drug action, we tested whether calpain inhibitor XI and ibudilast could rescue resting cytosolic calcium following the loss of WFS1. Sustained elevation in resting cytosolic calcium can lead to harmful cellular processes resulting in cell death [15] and impaired insulin secretion [18]. Both calpain inhibitor XI and ibudilast lowered the resting cytosolic calcium in WFS1-KO cells to the level of WFS1-WT cells (FIGS. 19D-E), underscoring that disrupted calcium signaling is an important contributor to Wolfram syndrome pathology and can be targeted with calpain inhibitor XI and ibudilast.

WFS1-KO Cells Show Decreased Insulin Secretion, which can be Reversed by Calpain Inhibitor XI and Ibudilast In addition to reduced 0-cell mass (FIG. 19), decreased glucose-stimulated insulin secretion was observed in studies investigating animal models with WFS1 deficiency and corresponding pancreatic islets [42, 45, 46]. When we measured glucose-stimulated insulin secretion, stimulation with 9 mM glucose significantly increased insulin secretion in WFS1-WT cells, whereas WFS1-KO cells failed to exhibit a significant increase (FIG. 5A). This resulted in a significantly lower insulin secretion rate in WFS1-KO cells compared to WFS1-WT cells at 9 mM glucose. Adding either calpain inhibitor XI or ibudilast reversed the impairment of glucose-stimulated insulin secretion in WFS1-KO cells. Treatment with calpain inhibitor XI did not affect insulin secretion in WFS1-WT cells and rescued secretion in WFS1-KO cells. Similar to another PDE4-inhibitor roflumilast [47], ibudilast enhanced insulin secretion at baseline in both cell lines. Following glucose stimulation, ibudilast ameliorated the difference between WFS1-WT and WFS1-KO cells.

WFS1-KO cells show decreased insulin receptor and protein kinase B/Akt signaling. Studies performed in animal models lacking the insulin receptor (IR) and insulin-like growth factor I (IGFI) receptor indicate that insulin also exerts an important effect on β-cells, and that IR signaling regulates survival and insulin secretion in β cells [48-50]. Therefore, we examined the expression levels of proteins involved in the insulin signaling network. Total IR and proteinkinase B (Akt) were similar between the WFS1-WT. WFS1-KO, and WFS1-OE cells (SI Appendix, FIGS. 6SA-B). Phosphorylation of the insulin receptor (pIRβ-Y1150/1151) and Akt (pS473 and pT308) was significantly reduced in WFS1-KO cells (FIGS. 5B-F). Reintroducing WFS1 in WFS1-KO cells significantly increased pIRβ-Y1150/1151 and rescued pAkt-S473. These data suggest that disruption of JR and Akt signaling plays a role in Wolfram syndrome pathology.

Discussion

WFS1 Regulates Intracellular Calcium Homeostasis

Here, we describe how intracellular calcium is globally dysregulated in WFS1-KO β-cells. Consistent with previous studies in the field [11, 13, 14, 24]. WFS1-KO cells showed elevated resting cytosolic calcium and reduced ATP-evoked calcium transients from the ER to both the cytosol and mitochondria. The exact mechanism of WFS1-dependent InsP3R dysfunction is unclear. However, we were able to rule out reduced expression of InsP3Rs or decreased ER-calcium loading as causes. There remain several possible, not mutually exclusive explanations. First, WFS1 may interact directly with InsP3R [14] and positively regulate InsP3R function similar to NCS1 [51, 52]. Second, WFS1 may function as a calcium-permeable ion channel [53]. Taken together, our data investigating calcium signaling in a cellular disease model of Wolfram syndrome emphasize that WFS1 is a versatile regulator of calcium homeostasis.

WFS1-KO cells are predisposed to hyperglycemia-induced impairments. When cells were challenged with glucose toxicity, WFS1-KO cells showed more severely impaired calcium signaling than WFS1-WT cells. Similar to wildtype rat islets that were cultured in high glucose over one week [32], WFS1-KO cells showed no further increase of resting cytosolic calcium. Therefore, we propose that at baseline, WFS1-KO cells already show signaling impairments like "prediabetic" cells. Such impairments predispose them to more severe hyperglycemia-induced defects, as supported by the lower cell viability we observed in WFS1-KO cells following hyperglycemia. This may explain why Wolfram syndrome patients progressively develop more degenerative symptoms with age.

WFS1-KO cells show impaired IR and AKt signaling. Decreased IR and Akt signaling, likely linked through defects in PI3K and mTORC2 signaling [54], may contribute to impaired insulin secretion [55] and cell viability [56, 57] of WFS1-KO cells. Reduction of protein kinase B/Akt signaling may be due to the elevation of cytosolic calcium [58, 59]. In addition, protein phosphatase 2A (PP2A) reduces the phosphorylation of IR, Akt, and other insulin-signaling molecules and is known to be hyperactivated in diabetic states [60]. Although we saw no changes in the protein expression of the catalytic subunit of PP2A (PP2Ac, SI Appendix, FIGS. 6SC-D), the activity of PP2A is regulated by multiple factors, including calcium [61] and post-translational modifications [60]. Alternatively, the reduction in insulin secretion in WFS1-KO cells may downregulate the insulin signaling pathway. Akt signaling could be a new drug target for Wolfram syndrome as previously investigated in other conditions, including obesity and type 2 diabetes mellitus [62].

Restoring Calcium Homeostasis in WFS1-KO Cells

Neuronal calcium sensor-1 (NCS1). We found that overexpressing NCS1 is a promising strategy to restore calcium homeostasis in INS1 cells. NCS1 may normalize calcium dysregulation through its enhancing effect on InsP3R activity [51, 52] and its function as a calcium sensor [35]. Moreover, a recent study found that NCS1 was mis-localized in adipocytes of a high-fat diet mouse model [63]. Therefore, we speculate that localization or functions of NCS1 are similarly altered in "prediabetic" WFS1-KO cells.

Calpain inhibitor XI and ibudilast. Pharmacological interventions with calpain inhibitor XI and ibudilast rescued resting cytosolic calcium as well as cell viability and glucose-stimulated insulin secretion of WFS1-KO cells. The specific mechanism of action for both drugs in Wolfram syndrome has yet to be determined, but we provide evidence that they act through normalizing calcium homeostasis. Calpain, a calcium-dependent protease, is typically regulated by changes in cytosolic calcium [64]. Our observation that calpain normalized resting cytosolic calcium in WFS1-KO cells suggests feedback signaling between calpain activity and cytosolic calcium. The calpain pathway should be further investigated in β-cells in the context of hyperglycemia because calpain hyperactivity was observed in diabetic cardiomyocytes [65] and overexpression of calpastatin, the endogenous inhibitor of calpain, protected mice against diabetes [66]. We hypothesize that ibudilast normalizes calcium through its interaction with NCS1 [39]. Furthermore, the effect of ibudilast on PDE4—and hence cAMP levels—in WFS1-WT and WFS1-KO cells needs to be investigated because cAMP interacts with calcium signaling pathways and is similarly implicated in cell viability and insulin secretion of β-cells [67-69]. Because it is already approved for use in humans [44], ibudilast appears to be a safe drug candidate for Wolfram syndrome. In addition to restoring β-cell function, ibudilast may also reduce neurodegenerative symptoms of Wolfram syndrome as it is known to reduce neurotoxic symptoms [70-72] and is currently in clinical trial for multiple sclerosis [73] and amyotrophic lateral sclerosis [74].

Proposed Model and Future Directions

Dysregulations in calcium signaling have been implicated in the pathogenesis of diabetes mellitus [24, 75] and neurodegeneration [76, 77], the two hallmarks of Wolfram syndrome. Here, we propose a disease model for Wolfram syndrome where global dysregulation of intracellular calcium homeostasis disrupts associated pathways including calpain, NCS1, and Akt, and consequently causes reduced cell viability and insulin secretion (FIG. 5G). Calpain inhibitor XI and ibudilast reversed deficits caused by the loss of WFS1, which makes them promising drug candidates for the treatment of Wolfram syndrome. This effect should be recapitulated in cell lines expressing WFS1-variants as seen in patients, and then further tested in an animal model of Wolfram syndrome [45, 46]. To advance our understanding of the disease mechanism of Wolfram syndrome, the link between disrupted calcium and the IR/Akt pathway should be further investigated. Importantly, the IR signaling network is increasingly recognized as an essential and druggable pathway both in β-cells and the brain [78]. Because Wolfram syndrome was proposed as a model system for diabetes mellitus and neurodegenerative diseases [2], we expect that the findings presented in this manuscript will be relevant to many fields of research.

Supporting Information (SI Appendix):

Supplementary Methods:

Calcium Imaging with Fluo-4-AM

Buffers were prepared following the same protocol as described for calcium imaging with Fura-2-AM. Fura-4-AM dye powder (Termmo Fisher) was dissolved to 4 μM in calcium-containing HEPES buffer supplemented with 0.03% Pluronic acid (Thermo Fisher).

For measurements of ER-calcium release, cells were plated at a density of $2\times10^5$ cells per coverslip. After 2 days, calcium imaging was carried out as described for Fura-2-AM. Following stimulation with 50 nM ATP, cells were imaged using sequential excitation at 488 nm, and images were acquired with emission bandwidth of 501 to 555 nm. After background subtraction, data were normalized to the first 10 seconds of baseline recording. Subsequent data quantification was performed as described for Fura-2-AM. All figures depicting calcium imaging traces show the average of 8-12 coverslips, each with 40-70 cells, from at least 3 independent recordings.

For measurements of cytosolic calcium, $2.5\times10^4$ cells were plated per well on a black, clear-bottom 96-well plate. After 2 days, wells were carefully washed two times with calcium-containing HEPES-buffered saline solution. Then, cells were incubated in Fluo-4-AM dye solution for 45 min in the dark at room temperature. After washing off the dye, cells were kept in calcium-containing HEPES-buffered saline solution and imaged a Tecan Infinite M1000 Pro microplate reader using the following setting: 2 s linear shaking (2 mm, 654 rpm), followed by imaging in fluorescence mode with 40 μs integration time.

mRNA Analysis mRNA was isolated from INS1 cells grown to confluency using the RNeasy Mini kit (Qiagen) and reverse-transcribed to complementary DNA (cDNA) using High-Capacity cDNA Reverse Transcription Kit (Applied Biosystems). For real-time reverse transcription PCR, 40 ng of cDNA was used as transcript in a reaction with POWER SYBR Green MasterMix (Life Technologies) in a 7500 Fast machine (Applied Biosystems). Each sample was run as three technical replicates on a 96-well plate. Fold change in mRNA transcript levels was determined by using the 2-ΔΔCt method [1]. 18S was used as a control. The following primers were used: rat 18S (fwd. 5' CATTCG-AACGTCTGCCCTAT 3'; rev, 5' G7T CTCAGG-CTCCCTCTCC 3'), rat NCS1 fwd. 5' GGAGACCCCAC-CAAGTTCG 3' rev. S' A4CTCGATCCTGCCATCC7TTG 3').

Subcellular Fractionation

Subcellular fractionation to obtain homogenate, membrane, cytosolic, and mitochondrial fraction was carried out following the protocol provided by Abcam (R. Patten). Lysis buffer contained 250 mM Sucrose, 20 mM HEPES (pH 7.4), 10 mM KCl, 1.5 mM $MgCl_2$, 1 mM EDTA, and 1 mM EGTA. Cell lysate obtained from a 15 cm dish of confluent INS1 cells was passed through a 25G needle and centrifuged repeatedly resulting in the different fractions step by step. Additionally, we prepared crude mitochondrial extracts from HEK293 lysate using a mitochondrial extraction kit (Thermo Fisher, #89874). A cell suspension in HEK cell media (DMEM high glucose, 5% FBS, 1% PenStrep) was collected using TryLE and pelleted at 850×g for 2 min. Between steps of centrifuging and vortexing, the reagents provided in the kit were added to the pellet step by step. Finally, mitochondria were lysed in 2% CHAPS with tris buffer. For further analysis, fractionation samples were prepared for Western Blot (see above).

TABLE S1

List of primary antibodies used

| Antibody | Source | Identifier |
|---|---|---|
| WFS1 | Proteintech | 11558-1-AP |
| β-Actin | Cell Signaling | 8H10D10 |
| NCS1 | Santa Cruz | FL-190 |
| phospho-Akt (pAkt) (S473) | Cell Signaling | #4060 |
| phospho-Akt (pAkt) (T308) | Cell Signaling | #9275 |
| total-Akt (tAkt) | Cell Signaling | #2920 |
| Phospho-IGF-I Receptor β(Tyr1135/1136)/Insulin Receptor β (Tyr1150/1151) (pIRβ) | Cell Signaling | #3024 |
| total-Insulin-Receptor (tIR) | Gift from Dr. G. Shulman | |
| Calreticulin | Cell Signaling | #12238 |
| Inositol trisphosphate receptor isoform 1 (InsP3R1) | Homemade production | |
| Inositol trisphosphate receptor isoform 3 (InsP3R3) | BD biosciences | 610312 |
| α-Tubulin | Abcam | ab7291 |
| VDAC | Abcam | ab34726 |
| PP2A c subunit | Cell signaling | #2259 |

TABLE S2

Detailed statistical analysis for FIGS. 1S-5S. All data were included in statistical testing, relevant p-values are shown below.

| FIG. | Statistical test | P-value | Post-hoc test pairwise comparison |
|---|---|---|---|
| 1B | One-way ANOVA | p = 0.0006 | WFS1-WT vs. WFS1-KO: p = 0.0004<br>WFS1-WT vs. WFS1-OE: p = 0.1463<br>WFS1-KO vs. WFS1-OE: p = 0.009 |
| 1C | Two-tailed student t-test | p = 0.0002 | |
| 1E | One-way ANOVA | p = 0.0005 | WFS1-WT vs. WFS1-KO: p = 0.0004<br>WFS1-WT vs. WFS1-OE: p = 0.1568<br>WFS1-KO vs. WFS1-OE: p = 0.0096 |
| 1F | One-way ANOVA | p < 0.0001 | WFS1-WT vs. WFS1-KO: p < 0.0001<br>WFS1-WT vs. WFS1-OE: p < 0.0001<br>WFS1-KO vs. WFS1-OE: p = 0.0456 |
| 1G | One-way ANOVA | p = 0.0215 | WFS1-WT vs. WFS1-KO: p = 0.0345<br>WFS1-WT vs. WFS1-OE: p = 0.8356<br>WFS1-KO vs. WFS1-OE: p = 0.0420 |
| 1H | Two-tailed student t-test | p = 0.0021 | |
| 1I | Two-tailed student t-test | p = 0.0037 | |
| 1J | Two-tailed student t-test | p = 0.0001 | |
| 2A | One-way ANOVA | p = 0.0002 | WFS1-WT CTRL vs. WFS1-KO CTRL: p = 0.0005<br>WFS1-WT CTRL vs. WFS1-WT 30G: p = 0.0319<br>WFS1-KO CTRL vs. WFS1-KO 30G: p = 0.9214<br>WFS1-WT 30G vs. WFS1-KO 30G: p = 0.1954 |
| 2C | One-way ANOVA | p < 0.0001 | WFS1-WT CTRL vs. WFS1-WT 15G: p < 0.0001<br>WFS1-WT CTRL vs. WFS1-WT 30G: p < 0.0001<br>WFS1-WT 15G vs. WFS1-WT 30G: p = 0.0040<br>WFS1-KO CTRL vs. WFS1-KO 15G: p = 0.0219<br>WFS1-KO CTRL vs. WFS1-KO 30G: p < 0.0001<br>WFS1-KO 15G vs. WFS1-KO 30G: p = 0.6517<br>WFS1-WT CTRL vs. WFS1-KO CTRL: p < 0.0001<br>WFS1-WT 15G vs. WFS1-KO 15G: p = 0.0466<br>WFS1-WT 30G vs. WFS1-KO 30G: p = 0.9469<br>WFS1-WT 15G vs. WFS1-KO CTRL: p = 0.9996<br>WFS1-WT 30G vs. WFS1-KO 15G: p = 0.9841 |
| 2D | One-way ANOVA | p < 0.0001 | WFS1-WT CTRL vs. WFS1-WT 15G: p < 0.0001<br>WFS1-WT CTRL vs. WFS1-WT 30G: p < 0.0001<br>WFS1-WT 15G vs. WFS1-WT 30G: p = 0.0072<br>WFS1-KO CTRL vs. WFS1-KO 15G: p = 0.0062<br>WFS1-KO CTRL vs. WFS1-KO 30G: p < 0.0001<br>WFS1-KO 15G vs. WFS1-KO 30G: p = 0.5243<br>WFS1-WT CTRL vs. WFS1-KO CTRL: p < 0.0001<br>WFS1-WT 15G vs. WFS1-KO 15G: p = 0.0618<br>WFS1-WT 30G vs. WFS1-KO 30G: p = 0.7928<br>WFS1-WT 15G vs. WFS1-KO CTRL: p = 0.9998<br>WFS1-WT 30G vs. WFS1-KO 15G: p = 0.9946 |
| 2E | One-way ANOVA | p < 0.0001 | WFS1-WT CTRL vs. WFS1-WT 15G: p = 0.1663<br>WFS1-WT CTRL vs. WFS1-WT 30G: p < 0.0001<br>WFS1-WT 15G vs. WFS1-WT 30G: p = 0.0005<br>WFS1-KO CTRL vs. WFS1-KO 15G: p = 0.1327<br>WFS1-KO CTRL vs. WFS1-KO 30G: p = 0.0006<br>WFS1-KO 15G vs. WFS1-KO 30G: p = 0.7635<br>WFS1-WT CTRL vs. WFS1-KO CTRL: p < 0.0001<br>WFS1-WT 15G vs. WFS1-KO 15G: p = 0.0060<br>WFS1-WT 30G vs. WFS1-KO 30G: p = 0.9514<br>WFS1-WT 15G vs. WFS1-KO CTRL: p = 0.4714<br>WFS1-WT 30G vs. WFS1-KO 15G: p = 0.9956 |

TABLE S2-continued

Detailed statistical analysis for FIGS. 1S-5S. All data were included in statistical testing, relevant p-values are shown below.

| FIG. | Statistical test | P-value | Post-hoc test pairwise comparison |
|---|---|---|---|
| 3C | One-way ANOVA | $p < 0.0001$ | WFS1-WT CTRL vs. WFS1-WT 30G: $p = 0.0003$ |
| | | | WFS1-KO CTRL vs. WFS1-KO 30G: $p = 0.0366$ |
| 3F | One-way ANOVA | $p < 0.0001$ | WFS1-WT vs. WFS1-KO: $p = 0.0062$ |
| | | | WFS1-WT vs. e.v.: $p = 0.0029$ |
| | | | WFS1-KO vs. e.v.: $p = 0.8839$ |
| | | | WFS1-WT vs. NCS1-OE: $p = 0.9820$ |
| | | | WFS1-KO vs. NCS1-OE: $p = 0.0046$ |
| | | | e.v. vs. NCS1-OE: $p = 0.0006$ |
| 3G | One-way ANOVA | $p < 0.0001$ | WFS1-WT vs. WFS1-KO: $p = 0.0019$ |
| | | | WFS1-WT vs. e.v.: $p = 0.0007$ |
| | | | WFS1-KO vs. e.v.: $p = 0.8635$ |
| | | | WFS1-WT vs. NCS1-OE: $p = 0.2083$ |
| | | | WFS1-KO vs. NCS1-OE: $p < 0.0001$ |
| | | | e.v. vs. NCS1-OE: $p < 0.0001$ |
| 3H | One-way ANOVA | $p = 0.0003$ | WFS1-WT vs. WFS1-KO: $p = 0.0934$ |
| | | | WFS1-WT vs. e.v.: $p = 0.0354$ |
| | | | WFS1-KO vs. e.v.: $p = 0.9928$ |
| | | | WFS1-WT vs. NCS1-OE: $p = 0.9789$ |
| | | | WFS1-KO vs. NCS1-OE: $p = 0.0186$ |
| | | | e.v. vs. NCS1-OE: $p = 0.0009$ |
| 3I | One-way ANOVA | $p = 0.0298$ | WFS1-WT vs. WFS1-KO: $p = 0.0449$ |
| | | | WFS1-WT vs. NCS1-OE: $p = 0.9111$ |
| | | | WFS1-KO vs. NCS1-OE: $p = 0.0462$ |
| 4A | Two-tailed student t-test | $p = 0.6171$ | |
| 4C | One-way ANOVA | $p < 0.0001$ | WFS1-WT CTRL vs. WFS1-WT 30G: $p = 0.1259$ |
| | | | WFS1-WT CTRL vs. WFS1-WT 30G + CI: $p = 0.4930$ |
| | | | WFS1-WT CTRL vs. WFS1-WT 30G + IBU: $p > 0.9999$ |
| | | | WFS1-KO CTRL vs. WFS1-KO 30G: $p < 0.0001$ |
| | | | WFS1-KO CTRL vs. WFS1-KO 30G + CI: $p > 0.9999$ |
| | | | WFS1-KO CTRL vs. WFS1-KO 30G + IBU: $p = 0.8563$ |
| | | | WFS1-WT 30G vs. WFS1-KO 30G: $p < 0.0001$ |
| | | | WFS1-WT CI vs. WFS1-KO CI: $p > 0.9999$ |
| | | | WFS1-WT IBU vs. WFS1-KO IBU: $p = 0.9980$ |
| | | | WFS1-WT 30G + CI vs. WFS1-KO 30G + CI: $p = 0.5953$ |
| | | | WFS1-WT 30G + IBU vs. WFS1-KO 30G + IBU: $p = 0.9861$ |
| 4D | One-way ANOVA | $p < 0.0001$ | WFS1-WT CTRL vs. WFS1-KO CTRL: $p < 0.0001$ |
| | | | WFS1-WT CTRL vs. WFS1-WT C.I.: $p = 0.9940$ |
| | | | WFS1-WT CTRL vs. WFS1-KO C.I.: $p = 0.6244$ |
| | | | WFS1-KO CTRL vs. WFS1-KO C.I.: $p = 0.0007$ |
| 4E | One-way ANOVA | $p = 0.0029$ | WFS1-WT CTRL vs. WFS1-KO CTRL: $p = 0.0097$ |
| | | | WFS1-WT CTRL vs. WFS1-WT IBU: $p = 0.9942$ |
| | | | WFS1-WT CTRL vs. WFS1-KO IBU.: $p = 0.9002$ |
| | | | WFS1-KO CTRL vs. WFS1-KO IBU: $p = 0.0484$ |
| 5A | One-way ANOVA | $p < 0.0001$ | WFS1-WT CTRL 2.5G vs. WFS1-KO CTRL 2.5G: $p = 0.6053$ |
| | | | WFS1-WT 9G CTRL vs. WFS1-KO 9G CTRL: $p = 0.0328$ |
| | | | WFS1-WT CTRL 2.5G vs. WFS1-WT CTRL 9G: $p = 0.0008$ |
| | | | WFS1-KO CTRL 2.5G vs. WFS1-KO CTRL 9G: $p = 0.0664$ |
| | | | WFS1-WT CTRL 2.5G vs. WFS1-WT C.I. 2.5G: $p > 0.9999$ |
| | | | WFS1-WT CTRL 9G vs. WFS1-WT C.I. 9G: $p > 0.9999$ |
| | | | WFS1-WT C.I. 2.5G vs. WFS1-KO C.I. 2.5G: $p > 0.9999$ |
| | | | WFS1-WT C.I. 9G C.I. vs. WFS1-KO C.I. 9G: $p = 0.8072$ |
| | | | WFS1-WT C.I. 2.5G vs. WFS1-WT C.I. 9G: $p = 0.0006$ |
| | | | WFS1-KO C.I. 2.5G vs. WFS1-KO C.I. 9G: $p = 0.0236$ |
| | | | WFS1-WT CTRL 2.5G vs. WFS1-WT IBU 2.5G: $p = 0.0005$ |
| | | | WFS1-WT CTRL 9G vs. WFS1-WT IBU 9G: $p = 0.0244$ |
| | | | WFS1-WT IBU 2.5G vs. WFS1-KO IBU 2.5G: $p > 0.9999$ |
| | | | WFS1-WT IBU 9G C.I. vs. WFS1-KO IBU 9G: $p = 0.9998$ |
| | | | WFS1-WT IBU 2.5G vs. WFS1-WT IBU 9G: $p = 0.0355$ |
| | | | WFS1-KO IBU 2.5G vs. WFS1-KO IBU 9G: $p = 0.0010$ |
| 5C | One-way ANOVA | $p < 0.0001$ | WFS1-WT vs. WFS1-KO: $p < 0.0001$ |
| | | | WFS1-WT vs. WFS1-OE: $p = 0.0003$ |
| | | | WFS1-KO vs. WFS1-OE: $p < 0.0001$ |
| 5D | One-way ANOVA | $p < 0.0001$ | WFS1-WT vs. WFS1-KO: $p < 0.0001$ |
| | | | WFS1-WT vs. WFS1-OE: $p = 0.4867$ |
| | | | WFS1-KO vs. WFS1-OE: $p = 0.0005$ |
| 5F | Two-tailed student t-test | $p = 0.0026$ | |

REFERENCE FOR SUPPLEMENTAL INFORMATION SI

1. Schmittgen, T. D. and K J. Livak, *Analyzing real-time PCR data by the comparative C(T) method.* Nat Protoc, 2008. 3(6): p. 1101-8.

REFERENCES FIRST SET

1. Kinsley B T, Swift M, Dumont R H, Swift R G. Morbidity and mortality in the Wolfram syndrome. Diabetes care. 1995; 18(12):1566-70. Epub 1995/12/01. PubMed PMID: 8722052.

2. Urano F. Wolfram Syndrome: Diagnosis, Management, and Treatment. Curr Diab Rep. 2016; 16(1):6. Epub 2016/01/09. doi: 10.1007/s11892-015-0702-6. PubMed PMID: 26742931; PubMed Central PMCID: PMCPMC4705145.
3. Barrett T G, Bundey S E, Macleod A F. Neurodegeneration and diabetes: UK nationwide study of Wolfram (DIDMOAD) syndrome. Lancet. 1995; 346(8988):1458-63. Epub 1995/12/02. PubMed PMID: 7490992.
4. Angebault C, Fauconnier J, Patergnani S, Rieusset J, Danese A, Affortit C A, Jagodzinska J, Megy C, Quiles M. Cazevieille C, Korchagina J. Bonnet-Wersinger D, Milea D, Hamel C. Pinton P, Thiry M, Lacampagne A. Delprat B, Delettre C. ER-mitochondria cross-talk is regulated by the Ca(2+) sensor NCS1 and is impaired in Wolfram syndrome. Sci Signal. 2018; 11(553). Epub 2018/10/26. doi: 10.1126/scisignal.aaq1380. PubMed PMID: 30352948.
5. Fujimoto A, Furuta M. Totoki Y, Tsunoda T, Kato M, Shiraishi Y, Tanaka H, Taniguchi H, Kawakami Y, Ueno M, Gotoh K. Ariizumi S. Wardell C P, Hayami S, Nakamura T. Aikata H. Arihiro K. Boroevich K A, Abe T, Nakano K. Maejima K, Sasaki-Oku A, Ohsawa A, Shibuya T, Nakamura H, Hama N. Hosoda F, Arai Y, Ohashi S, Urushidate T. Nagae G, Yamamoto S, Ueda H, Tatsuno K. Ojima H, Hiraoka N, Okusaka T, Kubo M, Marubashi S, Yamada T, Hirano S. Yamamoto M, Ohdan H, Shimada K, Ishikawa O, Yamaue H, Chayama K, Miyano S, Aburatani H, Shibata T, Nakagawa H. Whole-genome mutational landscape and characterization of noncoding and structural mutations in liver cancer. Nat Genet. 2016; 48(5):500-9. Epub 2016/04/12. doi: 10.1038/ng.3547. PubMed PMID: 27064257.
6. Hilfiker S. Neuronal calcium sensor-1: a multifunctional regulator of secretion. Biochem Soc Trans. 2003; 31(Pt 4):828-32. Epub 2003/07/31. doi: 10.1042/. PubMed PMID: 12887315.
7. Weiss J L, Hui H, Burgoyne R D. Neuronal calcium sensor-1 regulation of calcium channels, secretion, and neuronal outgrowth. Cellular and molecular neurobiology. 2010; 30(8):1283-92. Epub 2010/11/26. doi: 10.1007/s10571-010-9588-7. PubMed PMID: 21104311.
8. Moore L M, England A. Ehrlich B E, Rimm D L. Calcium Sensor, NCS-1, Promotes Tumor Aggressiveness and Predicts Patient Survival. Molecular cancer research: MCR. 2017; 15(7):942-52. Epub 2017/03/10. doi: 10.1158/1541-7786.mcr-16-0408. PubMed PMID: 28275088: PubMed Central PMCID: PMCPmc5500411.
9. Apasu J E, Schuette D, LaRanger R, Steinle J A, Nguyen L D, Grosshans H K, Zhang M. Cai W L, Yan Q, Robert M E, Mak M, Ehrlich B E. Neuronal calcium sensor 1 (NCS1) promotes motility and metastatic spread of breast cancer cells in vitro and in vivo. FASEB journal: official publication of the Federation of American Societies for Experimental Biology. 2018:fj201802004R. Epub 2018/12/29. doi: 10.1096/fj.201802004R. PubMed PMID: 30592625.
10. Benbow J H, Mann T, Keeler C. Fan C, Hodsdon M E, Lolis E, DeGray B. Ehrlich B E. Inhibition of paclitaxel-induced decreases in calcium signaling. The Journal of biological chemistry. 2012; 287(45):37907-16. Epub 2012/09/19. doi: 10.1074/jbc.M112.385070. PubMed PMID: 22988235; PubMed Central PMCID: PMCPMC3488062.
11. Benbow J H, Mann T, Keeler C, Fan C, Hodsdon M, Lolis E, Degray B, Ehrlich B E. Inhibition of Paclitaxel-Induced Decreases in Calcium Signaling. The Journal of biological chemistry. 2012. Epub 2012/09/19. doi: 10.1074/jbc.M112.385070. PubMed PMID: 22988235.
12. Benbow J H, Degray B, Ehrlich B E. Protection of neuronal calcium sensor 1 in cells treated with Taxol. The Journal of biological chemistry. 2011. Epub 2011/08/03. doi: M11.265751 [pii]10.1074/jbc.M111.265751. PubMed PMID: 21808066.
13. Urano F. Wolfram syndrome iPS cells: the first human cell model of endoplasmic reticulum disease. Diabetes. 2014; 63(3):844-6. Epub 2014/02/22. doi: 10.2337/db13-1809. PubMed PMID: 24556864: PubMed Central PMCID: PMCPMC3931391.
14. Maleki N, Bashardoust B, Zakeri A, Salehifar A, Tavosi Z. Diabetes mellitus, diabetes insipidus, optic atrophy, and deafness: A case of Wolfram (DIDMOAD) syndrome. Journal of current ophthalmology. 2016; 27(3-4):132-5. doi: 10.1016/j.joco.2015.11.003. PubMed PMID: 27239592.
15. Urano F. Wolfram Syndrome: Diagnosis, Management, and Treatment. Current diabetes reports. 2016; 16(1):6-. Epub 01/07. doi: 10.1007/s11892-015-0702-6. PubMed PMID: 26742931.
16. Barrett T G, Bundey S E. Wolfram (DIDMOAD) syndrome. Journal of medical genetics. 1997; 34(10):838-41. Epub 1997/11/14. PubMed PMID: 9350817; PubMed Central PMCID: PMCPmc1051091.
17. de Heredia M L, Cleries R. Nunes V. Genotypic classification of patients with Wolfram syndrome: insights into the natural history of the disease and correlation with phenotype. Genetics in medicine: official journal of the American College of Medical Genetics. 2013; 15(7):497-506. Epub 2013/02/23. doi: 10.1038/gim.2012.180. PubMed PMID: 23429432.
18. Wang B, Boeckel G R. Huynh L, Nguyen L, Cao W. De La Cruz E M, Kaftan E J, Ehrlich B E. Neuronal Calcium Sensor 1 Has Two Variants with Distinct Calcium Binding Characteristics. PloS one. 2016; 11(8):e0161414-e. doi: 10.1371/journal.pone.0161414. PubMed PMID: 27575489.
19. Fonseca S G, Gromada J, Urano F. Endoplasmic reticulum stress and pancreatic beta-cell death. Trends in endocrinology and metabolism: TEM. 2011; 22(7):266-74. Epub 2011/04/05. doi: 10.1016/j.tem.2011.02.008. PubMed PMID: 21458293; PubMed Central PMCID: PMCPmc3130122.
20. Yurimoto S, Hatano N, Tsuchiya M, Kato K, Fujimoto T, Masaki T, Kobayashi R, Tokumitsu H. Identification and Characterization of Wolframin, the Product of the Wolfram Syndrome Gene (WFS1), as a Novel Calmodulin-Binding Protein. Biochemistry. 2009; 48(18):3946-55. doi: 10.1021/bi900260y.
21. Angebault C, Fauconnier J. ER-mitochondria cross-talk is regulated by the Ca(2+) sensor NCS1 and is impaired in Wolfram syndrome2018; 11(553). doi: 10.1126/scisignal.aaq1380. PubMed PMID: 30352948.
22. Nakamura T Y, Nakao S, Wakabayashi S. Neuronal Ca(2+) sensor-1 contributes to stress tolerance in cardiomyocytes via activation of mitochondrial detoxification pathways. Journal of molecular and cellular cardiology. 2016; 99:23-34. Epub 2016/08/25. doi: 10.1016/j.yjmcc.2016.08.013. PubMed PMID: 27555477.
23. Bourne Y, Dannenberg J, Pollmann V, Marchot P, Pongs O. Immunocytochemical localization and crystal structure of human frequenin (neuronal calcium sensor 1). The Journal of biological chemistry. 2001; 276(15):11949-55. Epub 2000/12/08. doi: 10.1074/jbc.M009373200. PubMed PMID: 11092894.

24. Haynes L P, Fitzgerald D J, Wareing B, O'Callaghan D W, Morgan A, Burgoyne R D. Analysis of the interacting partners of the neuronal calcium-binding proteins L-CaBP1, hippocalcin, NCS-1 and neurocalcin delta. Proteomics. 2006:6(6):1822-32. Epub 2006/02/14. doi: 10.1002/pmic.200500489. PubMed PMID: 16470652.

25. Zhao X, Vamai P, Tuymetova G, Balla A. Toth Z E, Oker-Blom C, Roder J, Jeromin A, Balla T. Interaction of neuronal calcium sensor-1 (NCS-1) with phosphatidylinositol 4-kinase beta stimulates lipid kinase activity and affects membrane trafficking in COS-7 cells. The Journal of biological chemistry. 2001:276(43):40183-9. Epub 2001/08/30. doi: 10.1074/jbc.M104048200. PubMed PMID: 11526106.

26. Sippy T, Cruz-Martin A, Jeromin A, Schweizer F E. Acute changes in short-term plasticity at synapses with elevated levels of neuronal calcium sensor-1. Nature neuroscience. 2003:6(10):1031-8. Epub 2003/08/30. doi: 10.1038/nn 1117. PubMed PMID: 12947410: PubMed Central PMCID: PMCPmc3132582.

27. Nakamura T Y, Lee K, Artman M, Rudy B, Coetzee W A. The role of Kir2.1 in the genesis of native cardiac inward-rectifier K+ currents during pre- and postnatal development. Annals of the New York Academy of Sciences. 1999; 868:434-7. Epub 1999/07/22. PubMed PMID: 10414316.

28. Schlecker C, Boehmerle W, Jeromin A, DeGray B, Varshney A. Sharma Y, Szigeti-Buck K. Ehrlich B E. Neuronal calcium sensor-1 enhancement of InsP3 receptor activity is inhibited by therapeutic levels of lithium. J Clin Invest. 2006:116(6):1668-74. PubMed PMID: 16691292.

29. Boehmerle W, Splittgerber U, Lazarus M B, McKenzie K M, Johnston D G, Austin D J, Ehrlich B E. Paclitaxel induces calcium oscillations via an inositol 1,4,5-trisphosphate receptor and neuronal calcium sensor 1-dependent mechanism. Proceedings of the National Academy of Sciences of the United States of America. 2006; 103(48): 18356-61. Epub 11/17. doi: 10.1073/pnas.0607240103. PubMed PMID: 17114292.

30. Boehmerle W, Zhang K, Sivula M, Heidrich F M, Lee Y. Jordt S E, Ehrlich B E. Chronic exposure to paclitaxel diminishes phosphoinositide signaling by calpain-mediated neuronal calcium sensor-1 degradation. Proc Natl Acad Sci USA. 2007; 104(26):11103-8. Epub 2007/06/22. doi: 10.1073/pnas.0701546104. PubMed PMID: 17581879; PubMed Central PMCID: PMCPmc1904151.

31. Blachford C, Celic A, Petri E T, Ehrlich B E. Discrete proteolysis of neuronal calcium sensor-1 (NCS-1) by mu-calpain disrupts calcium binding. Cell calcium. 2009: 46(4):257-62. Epub 2009/09/08. doi: 10.1016/j.ccca.2009.08.002. PubMed PMID: 19732951; PubMed Central PMCID: PMCPmc2763996.

32. Benbow J H, DeGray B, Ehrlich B E. Protection of neuronal calcium sensor 1 protein in cells treated with paclitaxel. The Journal of biological chemistry. 2011; 286(40):34575-82. Epub 2011/08/03. doi: 10.1074/jbc.M111.265751. PubMed PMID: 21808066; PubMed Central PMCID: PMCPmc3186436.

33. Bononi A. Missiroli S. Poletti F, Suski J M, Agnoletto C, Bonora M. De Marchi E, Giorgi C, Marchi S, Patergnani S, Rimessi A, Wieckowski M R, Pinton P. Mitochondria-associated membranes (MAMs) as hotspot Ca(2+) signaling units. Advances in experimental medicine and biology. 2012; 740:411-37. Epub 2012/03/29. doi: 10.1007/978-94-007-2888-2_17. PubMed PMID: 22453952.

34. Nakamura T Y, Jeromin A, Mikoshiba K, Wakabayashi S. Neuronal calcium sensor-1 promotes immature heart function and hypertrophy by enhancing Ca2+ signals. Circulation research. 2011; 109(5):512-23. Epub 2011/07/09. doi: 10.1161/circresaha.111.248864. PubMed PMID: 21737792.

35. Marchi S, Patergnani S, Pinton P. The endoplasmic reticulum-mitochondria connection: one touch, multiple functions. Biochimica et biophysica acta. 2014:1837(4): 461-9. Epub 2013/11/12. doi: 10.1016/j.bbabio.2013.10.015. PubMed PMID: 24211533.

36. Giorgi C, Missiroli S, Patergnani S, Duszynski J, Wieckowski M R, Pinton P. Mitochondria-associated membranes: composition, molecular mechanisms, and physiopathological implications. Antioxidants & redox signaling. 2015; 22(12):995-1019. Epub 2015/01/06. doi: 10.1089/ars.2014.6223. PubMed PMID: 25557408.

37. Joshi A U, Komfeld O S, Mochly-Rosen D. The entangled ER-mitochondrial axis as a potential therapeutic strategy in neurodegeneration: A tangled duo unchained. Cell calcium. 2016; 60(3):218-34. Epub 2016/05/24. doi: 10.1016/j.ceca.2016.04.010. PubMed PMID: 27212603; PubMed Central PMCID: PMCPmc5012927.

38. Goll D E, Thompson V F, Li H, Wei W, Cong J. The calpain system. Physiological reviews. 2003:83(3):731-801. Epub 2003/07/05. doi: 10.1152/physrev.00029.2002. PubMed PMID: 12843408.

39. Camins A, Verdaguer E, Folch J, Pallas M. Involvement of calpain activation in neurodegenerative processes. CNS Drug Rev. 2006:12(2):135-48. doi: 10.1111/j.1527-3458.2006.00135.x. PubMed PMID: 16958987.

40. Liu S, Yin F, Zhang J, Qian Y. The role of calpains in traumatic brain injury. Brain Inj. 2014; 28(2):133-7. doi: 10.3109/02699052.2013.860479. PubMed PMID: 24456052.

41. Trinchese F. Fa M. Liu S, Zhang H, Hidalgo A, Schmidt S D, Yamaguchi H, Yoshii N, Mathews P M, Nixon R A, Arancio O. Inhibition of calpains improves memory and synaptic transmission in a mouse model of Alzheimer disease. The Journal of clinical investigation. 2008:118 (8):2796-807. doi: 10.1172/JC134254. PubMed PMID: 18596919; PubMed Central PMCID: PMC2441853.

42. Curcio M, Salazar I L, Mele M, Canzoniero L M, Duarte C B. Calpains and neuronal damage in the ischemic brain: The swiss knife in synaptic injury. Prog Neurobiol. 2016: 143:1-35. doi: 10.1016/j.pneurobio.2016.06.001. PubMed PMID: 27283248.

43. Nakagawa T, Yuan J. Cross-talk between two cysteine protease families. Activation of caspase-12 by calpain in apoptosis. The Journal of cell biology. 2000; 150(4):887-94. Epub 2000/08/23. PubMed PMID: 10953012; PubMed Central PMCID: PMCPmc2175271.

44. Cui G M, Zhao Y X, Zhang N N, Liu Z S, Sun W C, Peng Q S. Amiloride attenuates lipopolysaccharide-accelerated atherosclerosis via inhibition of NHE1-dependent endothelial cell apoptosis. Acta pharmacologica Sinica. 2013; 34(2):231-8. Epub 2013/01/01. doi: 10.1038/aps.2012.155. PubMed PMID: 23274414: PubMed Central PMCID: PMCPmc4011619.

45. Gibson T B, Lawrence M C, Gibson C J, Vanderbilt C A, McGlynn K. Arnette D, Chen W, Collins J, Naziruddin B, Levy M F, Ehrlich B E, Cobb M H. Inhibition of glucose-stimulated activation of extracellular signal-regulated protein kinases 1 and 2 by epinephrine in pancreatic beta-cells. Diabetes. 2006:55(4):1066-73. Epub 2006/03/29. PubMed PMID: 16567530.

46. Menzies F M, Garcia-Arencibia M, Imarisio S, O'Sullivan N C, Ricketts T, Kent B A, Rao M V, Lam W, Green-Thompson Z W, Nixon R A, Saksida L M, Bussey T J, O'Kane C J, Rubinsztein D C. Calpain inhibition mediates autophagy-dependent protection against polyglutamine toxicity. Cell Death Differ. 2015; 22(3):433-44. doi: 10.1038/cdd.2014.151. PubMed PMID: 25257175; PubMed Central PMCID: PMC4326573.

47. Rao M V, McBrayer M K, Campbell J, Kumar A, Hashim A, Sershen H, Stavrides P H, Ohno M, Hutton M, Nixon R A. Specific calpain inhibition by calpastatin prevents tauopathy and neurodegeneration and restores normal lifespan in tau P301L mice. J Neurosci. 2014:34 (28):9222-34. doi: 10.1523/JNEUROSCI.1132-14.2014. PubMed PMID: 25009256; PubMed Central PMCID: PMC4087203.

48. Rao M V, Campbell J, Palaniappan A, Kumar A. Nixon R A. Calpastatin inhibits motor neuron death and increases survival of hSOD1 (G93A) mice. J Neurochem. 2016; 137(2):253-65. doi: 10.1111/jnc.13536. PubMed PMID: 26756888; PubMed Central PMCID: PMC4828294.

49. Terasmaa A, Soomets U, Oflijan J, Punapart M, Hansen M, Matto V, Ehrlich K, Must A, Koks S, Vasar E. Wfs1 mutation makes mice sensitive to insulin-like effect of acute valproic acid and resistant to streptozocin. Journal of physiology and biochemistry. 2011; 67(3):381-90. Epub 2011/04/05. doi: 10.1007/s13105-011-0088-0. PubMed PMID: 21461749.

50. Zhang K, Heidrich F M, DeGray B, Boehmerle W. Ehrlich B E. Paclitaxel accelerates spontaneous calcium oscillations in cardiomyocytes by interacting with NCS-1 and the InsP3R. Journal of molecular and cellular cardiology. 2010; 49(5):829-35. Epub 2010/08/31. doi: 10.1016/j.yjmcc.2010.08.018. PubMed PMID: 20801127: PubMed Central PMCID: PMCpmc2965648.

51. Boehmerle W, Splittgerber U. Lazarus M B, McKenzie K M, Johnston D G, Austin D J, Ehrlich B E. Paclitaxel induces calcium oscillations via an inositol 1,4,5-trisphosphate receptor and neuronal calcium sensor 1-dependent mechanism. Proc Natl Acad Sci USA. 2006; 103(48): 18356-61. Epub 2006/11/23. doi: 10.1073/pnas.0607240103. PubMed PMID: 17114292; PubMed Central PMCID: PMCpmc1838755.

52. Moore L, England A, Ehrlich B E, Rimm D. Neuronal Calcium Sensor-1, NCS-1, Promotes Tumor Aggressiveness and Predicts Survival. Molecular Cancer Research. 2017:15(7):942-52. Epub March 2017. doi: doi 10.1158/1541-7786.MCR-16-0408.

53. Schuette D, Moore L M, Robert M E, Taddei T H, Ehrlich B E. Hepatocellular Carcinoma Outcome is Predicted by Expression of Neuronal Calcium Sensor 1. Cancer Epidemiol Biomarkers Prev. 2018. Epub 2018/05/24. doi: 10.1158/1055-9965.EPI-18-0167. PubMed PMID: 29789326.

54. Dykes M H. Evaluation of a muscle relaxant: dantrolene sodium (Dantrium). Jama. 1975; 231(8):862-4. Epub 1975/02/24. PubMed PMID: 1089167.

55. Luciani D S, Gwiazda K S, Yang T L, Kalynyak T B, Bychkivska Y, Frey M H, Jeffrey K D, Sampaio A V, Underhill T M, Johnson J D. Roles of IP3R and RyR Ca2+ channels in endoplasmic reticulum stress and beta-cell death. Diabetes. 2009; 58(2):422-32. Epub 2008/11/27. doi: 10.2337/db07-1762. PubMed PMID: 19033399; PubMed Central PMCID: PMCpmc2628616.

56. Burgoyne R D, Haynes L P. Sense and specificity in neuronal calcium signalling. Biochimica et biophysica acta. 2015:1853(9):1921-32. Epub 2014/12/03. doi: 10.1016/j.bbamcr.2014.10.029. PubMed PMID: 25447549; PubMed Central PMCID: PMCPMC4728190.

57. Lu S, Kanekura K, Hara T, Mahadevan J, Spears L D, Oslowski C M, Martinez R. Yamazaki-Inoue M, Toyoda M, Neilson A, Blanner P. Brown C M, Semenkovich C F, Marshall B A, Hershey T. Umezawa A, Greer P A, Urano F. A calcium-dependent protease as a potential therapeutic target for Wolfram syndrome. Proc Natl Acad Sci USA. 2014; 111(49):E5292-301. Epub 2014/11/26. doi: 10.1073/pnas.1421055111. PubMed PMID: 25422446; PubMed Central PMCID: PMCPmc4267371.

58. Kabbani N. Woll M P. Nordman J C, Levenson R. Dopamine receptor interacting proteins: targeting neuronal calcium sensor-1/D2 dopamine receptor interaction for antipsychotic drug development. Curr Drug Targets. 2012; 13(1):72-9. Epub 2011/07/23. PubMed PMID: 21777187.

59. Blachford C, Celic A, Petri E T, Ehrlich B E. Discrete proteolysis of neuronal calcium sensor-1 (NCS-1) by mu-calpain disrupts calcium binding. Cell Calcium. 2009. PubMed PMID: 19732951.

60. Keeler C, Poon G, Kuo I Y, Ehrlich B E, Hodsdon M E. An explicit formulation approach for the analysis of calcium binding to E F-hand proteins using isothermal titration calorimetry. Biophys J. 2013:105(12):2843-53. doi: 10.1016/j.bpj.2013.11.017. PubMed PMID: 24359756: PubMed Central PMCID: PMC3882476.

61. Celic A S, Petri E T, Benbow J, Hodsdon M E, Ehrlich B E, Boggon T J. Calcium-induced conformational changes in C-terminal tail of polycystin-2 are necessary for channel gating. The Journal of biological chemistry. 2012; 287(21):17232-40. Epub 2012/04/05. doi: 10.1074/jbc.M112.354613. PubMed PMID: 22474326; PubMed Central PMCID: PMCpmc3366810.

62. Petri E T, Celic A, Kennedy S D, Ehrlich B E, Boggon T J, Hodsdon M E. Structure of the E F-hand domain of polycystin-2 suggests a mechanism for Ca2+-dependent regulation of polycystin-2 channel activity. Proc Natl Acad Sci USA. 2010:107(20):9176-81. Epub 2010/05/05. doi: 10.1073/pnas.0912295107. PubMed PMID: 20439752: PubMed Central PMCID: PMCpmc2889120.

63. Keeler C, Tettamanzi M C, Meshack S, Hodsdon M E. Contribution of individual histidines to the global stability of human prolactin. Protein science: a publication of the Protein Society. 2009; 18(5):909-20. Epub 2009/04/23. doi: 10.1002/pro.100. PubMed PMID: 19384991: PubMed Central PMCID: PMCpmc2771294.

64. Tettamanzi M C, Keeler C, Meshack S, Hodsdon M E. Analysis of site-specific histidine protonation in human prolactin. Biochemistry. 2008; 47(33):8638-47. Epub 2008/07/26. doi: 10.1021/bi800444t. PubMed PMID: 18652486; PubMed Central PMCID: PMCpmc2766358.

65. Pandalaneni S. Karuppiah V, Saleem M, Haynes L P, Burgoyne R D, Mayans O, Derrick J P, Lian L Y. Neuronal Calcium Sensor-1 Binds the D2 Dopamine Receptor and G-protein-coupled Receptor Kinase 1 (GRK1) Peptides Using Different Modes of Interactions. The Journal of biological chemistry. 2015:290(30):18744-56. doi: 10.1074/jbc.M114.627059. PubMed PMID: 25979333: PubMed Central PMCID: PMCPMC4513130.

66. Keeler C, Jablonski E M, Albert Y B, Taylor B D, Myszka D G, Clevenger C V, Hodsdon M E. The kinetics of binding human prolactin, but not growth hormone, to the prolactin receptor vary over a physiologic pH range. Biochemistry. 2007:46(9):2398-410. Epub 2007/02/07. doi: 10.1021/bi061958v. PubMed PMID: 17279774.

67. Heidarsson P O, Bjerrum-Bohr I, Jensen G A, Pongs O, Finn B E, Poulsen F M, Kragelund B B. The C-terminal tail of human neuronal calcium sensor 1 regulates the conformational stability of the Ca(2)(+)(−) activated state. Journal of molecular biology. 2012; 417(1-2):51-64. Epub 2012/01/10. doi: 10.1016/j jmb.2011.12.049. PubMed PMID: 22227393.
68. Bumpus E, Hershey T, Doty T, Ranck S, Gronski M, Urano F, Foster E R. Understanding activity participation among individuals with Wolfram Syndrome. The British journal of occupational therapy. 2018; 81(6):348-57. Epub 04/13. doi: 10.1177/0308022618757182. PubMed PMID: 29861534.
69. Feriod C N, Oliveira A G, Guerra M T, Nguyen L, Richards K M, Jurczak M J. Ruan H B, Camporez J P, Yang X, Shulman G I, Bennett A M, Nathanson M H, Ehrlich B E. Hepatic Inositol 1,4,5 Trisphosphate Receptor Type 1 Mediates Fatty Liver. Hepatology communications. 2017:1(1):23-35. Epub 2017/10/03. doi: 10.1002/hep4.1012. PubMed PMID: 28966992: PubMed Central PMCID: PMCPmc5613674.
70. Feriod C N, Nguyen L, Jurczak M J, Kruglov E A, Nathanson M H, Shulman G I, Bennett A M, Ehrlich B E. Inositol 1,4,5-trisphosphate receptor type II (InsP3R-II) is reduced in obese mice, but metabolic homeostasis is preserved in mice lacking InsP3R-II. American journal of physiology Endocrinology and metabolism. 2014; 307 (11):E1057-64. Epub 2014/10/16. doi: 10.1152/ajpendo.00236.2014. PubMed PMID: 25315698: PubMed Central PMCID: PMCPmc4254986.
71. Holmes C, Eisenhofer G, Goldstein D S. Improved assay for plasma dihydroxyphenylacetic acid and other catechols using high-performance liquid chromatography with electrochemical detection. Journal of chromatography B, Biomedical applications. 1994; 653(2):131-8. Epub 1994/03/04. PubMed PMID: 8205240.
72. Atcheson R, Lambert D G, Hirst R A. Rowbotham D J. Studies on the mechanism of [3H]-noradrenaline release from SH-SY5Y cells: the role of Ca2+ and cyclic AMP. British journal of pharmacology. 1994:111(3):787-92. Epub 1994/03/01. PubMed PMID: 8019757; PubMed Central PMCID: PMCPmc1910113.
73. Hirata K. Dufour J F, Shibao K, Knickelbein R, O'Neill A F, Bode H P, Cassio D. St-Pierre M V, Larusso N F, Leite M F, Nathanson M H. Regulation of Ca(2+) signaling in rat bile duct epithelia by inositol 1,4,5-trisphosphate receptor isoforms. Hepatology (Baltimore, Md). 2002; 36(2):284-96. Epub 2002/07/27. doi: 10.1053/jhep.2002.34432. PubMed PMID: 12143036; PubMed Central PMCID: PMCPmc2987686.
74. Kuo I Y, Brill, A. L., Lemos, F. O., Jiang, J. Y., Falcone, J. L., Kimmerling, E. P., Cai, Y., Dong, K., Kaplan, D. L., Wallace, D. P., Hofer, A. M., Ehrlich, B. E. Polycystin 2 regulates mitochondrial calcium signaling, bioenergetics, 1 and dynamics through mitofusin 2 Science Signaling 2019.
75. Doyle T, Chen Z, Muscoli C, Bryant L, Esposito E. Cuzzocrea S, Dagostino C, Ryerse J, Rausaria S, Kamadulski A, Neumann W L, Salvemini D. Targeting the Overproduction of Peroxynitrite for the Prevention and Reversal of Paclitaxel-Induced Neuropathic Pain. The Journal of Neuroscience. 2012; 32(18):6149. doi: 10.1523/JNEUROSCI.6343-11.2012.
76. Hayashi T, Rizzuto R, Hajnoczky G, Su T P. MAM: more than just a housekeeper. Trends in cell biology. 2009; 19(2):81-8. Epub 2009/01/16. doi: 10.1016/j.tcb.2008.12.002. PubMed PMID: 19144519; PubMed Central PMCID: PMCPmc2750097.
77. Mo M, Erielyi I, Szigeti-Buck K, Benbow J H, Ehrlich B E. Prevention of paclitaxel-induced peripheral neuropathy by lithium pretreatment. FASEB journal: official publication of the Federation of American Societies for Experimental Biology. 2012; 26(11):4696-709. Epub 2012/08/15. doi: 10.1096/fj.12-214643. PubMed PMID: 22889832; PubMed Central PMCID: PMCPmc3475250.
78. Wang Wi, Shi D, Li L L, Wang S M. [The effect of pre-operative chemotherapy on calpain in cells of gastrointestinal malignant tumors]. Zhonghua wai ke za zhi [Chinese journal of surgery]. 2004:42(15):922-5. Epub 2004/09/15. PubMed PMID: 15363254.
79. Huang Y, Wang K K. The calpain family and human disease. Trends in molecular medicine. 2001; 7(8):355-62. Epub 2001/08/23. PubMed PMID: 11516996.
80. Giehl E, Lemos F O, Huang Y, Giordano F J, Kuo I Y, Ehrlich B E. Polycystin 2-dependent cardio-protective mechanisms revealed by cardiac stress. Pflugers Archiv: European journal of physiology. 2017; 469(11):1507-17. Epub 2017/08/02. doi: 10.1007/s00424-017-2042-7. PubMed PMID: 28762163; PubMed Central PMCID: PMCPmc5792378.
81. Cheatham M A, Huynh K H, Gao J, Zuo J, Dallos P. Cochlear function in Prestin knockout mice. The Journal of physiology. 2004; 560(Pt 3):821-30. Epub 2004/08/21. doi: 10.1113/jphysiol.2004.069559. PubMed PMID: 15319415; PubMed Central PMCID: PMCPmc1665294.
82. Leone S, Recinella L. Chiavaroli A, Ferrante C, Orlando G. Vacca M, Salvatori R, Brunetti L. Behavioural phenotyping, learning and memory in young and aged growth hormone-releasing hormone-knockout mice. Endocrine connections. 2018; 7(8):924-31. Epub 2018/10/10. doi: 10.1530/ec-18-0165. PubMed PMID: 30300535; PubMed Central PMCID: PMCPmc6130317.
83. Sclafani A. Oral, post-oral and genetic interactions in sweet appetite. Physiology & behavior. 2006; 89(4):525-30. Epub 2006/05/02. doi: 10.1016/j.physbeh.2006.03.021. PubMed PMID: 16647093; PubMed Central PMCID: PMCPmc2364709.
84. Wadia R J, Stolar M. Grens C, Ehrlich B E, Chao H H. The prevention of chemotherapy induced peripheral neuropathy by concurrent treatment with drugs used for bipolar disease: a retrospective chart analysis in human cancer patients. Oncotarget. 2017; 9(7):7322-31. doi: 10.18632/oncotarget. 23467. PubMed PMID: 29484113.

REFERENCES SECOND SET

1. Barrett, T. G. and S. E. Bundey, *Wolfram (DIDMOAD) syndrome*, J Med Genet, 1997. 34(10): p. 838-41.
2. Rigoli, L., et al., *Genetic and clinical aspects of Wolfram syndrome 1, a severe neurodegenerative disease*. Pediatr Res, 2018. 83(5): p. 921-929.
3. Urano, F., *Wolfram Syndrome: Diagnosis, Management, and Treatment*, Curr Diab Rep, 2016. 16(1): p. 6.
4. Khanim, F., et al., *WFS1/wolframin mutations, Wolfram syndrome, and associated diseases*. Hum Mutat, 2001. 17(5): p. 357-67.
5. Inoue, K. and J. R. Lupski, *Genetics and genomics of behavioral and psychiatric disorders*. Curr Opin Genet Dev, 2003. 13(3): p. 303-9.
6. Swift, R. G., et al., *Predisposition of Wolfram syndrome heterozygotes to psychiatric illness*. Mol Psychiatry, 1998. 3(1): p. 86-91.

7. Swift, M. and R. G. Swift, *Psychiatric disorders and mutations at the Wolfram syndrome locus.* Biol Psychiatry, 2000. 47(9): p. 787-93.
8. Takeda, K., et al., *WFS1 (Wolfram syndrome 1) gene product: predominant subcellular localization to endoplasmic reticulum in cultured cells and neuronal expression in rat brain.* Hum Mol Genet, 2001. 10(5): p. 477-84.
9. Fonseca. S. G., et al., *WFS1 is a novel component of the unfolded protein response and maintains homeostasis of the endoplasmic reticulum in pancreatic beta-cells.* J Biol Chem, 2005. 280(47): p. 39609-15.
10. Fonseca, S. G., et al., *Wolfram syndrome 1 gene negatively regulates ER stress signaling in rodent and human cells.* J Clin Invest, 2010. 120(3): p. 744-55.
11. Cagalinec, M., et al., *Role of Mitochondrial Dynamics in Neuronal Development: Mechanism for Wolfram Syndrome.* PLoS Biol, 2016. 14(7): p. e1002511.
12. Takei, D., et al., *WFS1 protein modulates the free Ca(2+) concentration in the endoplasmic reticulum.* FEBS Lett, 2006. 580(24): p. 5635-40.
13. Lu, S., et al., *A calcium-dependent protease as a potential therapeutic target for Wolfram syndrome.* Proc Natl Acad Sci USA, 2014. 111(49): p. E5292-301.
14. Angebault, C., et al., *ER-mitochondria cross-talk is regulated by the Ca(2+) sensor NCS1 and is impaired in Wolfram syndrome.* Sci Signal, 2018. 11(553).
15. Orrenius, S., B. Zhivotovsky, and P. Nicotera, *Regulation of cell death: the calcium-apoptosis link.* Nat Rev Mol Cell Biol, 2003. 4(7): p. 552-65.
16. Huang, C. J., et al., *Calcium-activated calpain-2 is a mediator of beta cell dysfunction and apoptosis in type 2 diabetes.* J Biol Chem, 2010. 285(1): p. 33948.
17. Soleimanpour, S. A., et al., *Calcineurin signaling regulates human islet {beta}-cell survival.* J Biol Chem, 2010. 285(51): p. 40050-9.
18. Somesh, B. P., et al., *Chronic glucolipotoxic conditions in pancreatic islets impair insulin secretion due to dysregulated calcium dynamics,* glucose responsiveness and mitochondrial activity. BMC Cell Biol, 2013. 14: p. 31.
19. Qureshi, F. M., et al., *Stress-induced dissociations between intracellular calcium signaling and insulin secretion in pancreatic islets.* Cell Calcium, 2015. 57(5-6): p. 366-375.
20. Gilon, P., et al., *Calcium signaling in pancreatic beta-cells in health and in Type 2 diabetes.* Cell Calcium, 2014. 56(5): p. 340-61.
21. Magi, S., et al., *Intracellular Calcium Dysregulation: Implications for Alzheimer's Disease.* Biomed Res Int, 2016. 2016: p. 6701324.
22. Monteith, G. R., N. Prevarskaya, and S. J. Roberts-Thomson. *The calcium-cancer signalling nexus.* Nat Rev Cancer, 2017. 17(6): p. 367-380.
23. Massry, S. G. and M. Smogorzewski, *Role of elevated cytosolic calcium in the pathogenesis of complications in diabetes mellitus.* Miner Electrolyte Metab, 1997. 23(3-6): p. 253-60.
24. Arruda, A. P. and G. S. Hotamisligil, *Calcium Homeostasis and Organelle Function in the Pathogenesis of Obesity and Diabetes.* Cell Metab, 2015. 22(3): p. 381-97.
25. Raturi, A. and T. Simmen, *Where the endoplasmic reticulum and the mitochondrion tie the knot: the mitochondria-associated membrane (MAM).* Biochim Biophys Acta, 2013. 1833(1): p. 213-24.
26. Area-Gomez, E., et al., *A key role for MAM in mediating mitochondrial dysfunction in Alzheimer disease.* Cell Death Dis, 2018. 9(3): p. 335.
27. Tubbs, E., et al., *Mitochondria-associated endoplasmic reticulum membrane (MAM) integrity is required for insulin signaling and is implicated in hepatic insulin resistance.* Diabetes, 2014. 63(10): p. 3279-94.
28. Thivolet, C., et al., *Reduction of endoplasmic reticulum-mitochondria interactions in beta cells from patients with type 2 diabetes.* PLoS One, 2017. 12(7): p. e0182027.
29. Zhang, A., et al., *Quantitative proteomic analyses of human cytomegalovirus-induced restructuring of endoplasmic reticulum-mitochondrial contacts at late times of infection.* Mol Cell Proteomics, 2011. 10(10): p. M111 009936.
30. Poston, C. N., S. C. Krishnan, and C. R. Bazemore-Walker, *In-depth proteomic analysis of mammalian mitochondria-associated membranes (MAM).* J Proteomics, 2013. 79: p. 219-30.
31. Homer, S. M., et al., *Proteomic analysis of mitochondrial-associated ER membranes (MAM) during RNA virus infection reveals dynamic changes in protein and organelle trafficking.* PLoS One, 2015. 10(3): p. e0117963.
32. Khaldi, M. Z., et al., *Increased glucose sensitivity of both triggering and amplifying pathways of insulin secretion in rat islets cultured for 1 wk in high glucose.* Am J Physiol Endocrinol Metab, 2004. 287(2): p. E207-17.
33. Tsuboi, T., et al., *Sustained exposure to high glucose concentrations modifies glucose signaling and the mechanics of secretory vesicle fusion in primary rat pancreatic beta-cells.* Diabetes, 2006. 55(4): p. 1057-65.
34. Tang, C., et al., *Glucose-induced beta cell dysfunction in vivo in rats: link between oxidative stress and endoplasmic reticulum stress.* Diabetologia, 2012. 55(5): p. 1366-79.
35. Nakamura, T. Y., S. Nakao, and S. Wakabayashi, *Emerging Roles of Neuronal Ca(2+) Sensor-1 in Cardiac and Neuronal Tissues: A Mini Review.* Front Mol Neurosci, 2019. 12: p. 56.
36. Nakamura, T. Y., et al., *Novel role of neuronal Ca2+ sensor-1 as a survival factor up-regulated in injured neurons.* J Cell Biol, 2006. 172(7): p. 1081-91.
37. Gromada, J., et al., *Neuronal calcium sensor-1 potentiates glucose-dependent exocytosis in pancreatic beta cells through activation of phosphatidylinositol 4-kinase beta.* Proc Natl Acad Sci USA, 2005. 102(29): p. 10303-8.
38. Nakamura, T. Y., S. Nakao, and S. Wakabayashi, *Neuronal Ca(2+) sensor-1 contributes to stress tolerance in cardiomyocytes via activation of mitochondrial detoxification pathways.* J Mol Cell Cardiol, 2016. 99: p. 23-34.
39. Benbow, J. H., et al., *Inhibition of paclitaxel-induced decreases in calcium signaling.* J Biol Chem. 2012. 287(45): p. 37907-16.
40. Mansilla. A., et al., *Interference of the complex between NCS-1 and Ric8a with phenothiazines regulates synaptic function and is an approach for fragile X syndrome.* Proc Natl Acad Sci USA, 2017. 114(6): p. E999-E1008.
41. Karasik, A., et al., *Genetically programmed selective islet beta-cell loss in diabetic subjects with Wolfram's syndrome.* Diabetes Care, 1989. 12(2): p. 135-8.
42. Riggs, A. C., et al., *Mice conditionally lacking the Wolfram gene in pancreatic islet beta cells exhibit diabetes as a result of enhanced endoplasmic reticulum stress and apoptosis.* Diabetologia, 2005. 48(11): p. 2313-21.
43. Paquet-Durand, F., et al., *Calpain is activated in degenerating photoreceptors in the rd1 mouse.* J Neurochem, 2006. 96(3): p. 802-14.
44. Rolan, P., M. Hutchinson, and K. Johnson, *Ibudilast: a review of its pharmacology, efficacy and safety in respi-* ratory and neurological disease. Expert Opin Pharmacother. 2009. 10(17): p. 2897-904.
45. Ishihara, H., et al., *Disruption of the WFS1 gene in mice causes progressive beta-cell loss and impaired stimulus-secretion coupling in insulin secretion.* Hum Mol Genet, 2004. 13(11): p. 1159-70.
46. Plaas, M., et al., *Wfp1-deficient rats develop primary symptoms of Wolfram syndrome: insulin-dependent diabetes, optic nerve atrophy and medullary degeneration.* Sci Rep, 2017. 7(1): p. 10220.
47. Waddleton, D., et al., *Phosphodiesterase 3 and 4 comprise the major cAMP metabolizing enzymes responsible for insulin secretion in INS-1 (832/13) cells and rat islets.* Biochem Pharmacol, 2008. 76(7): p. 884-93.
48. Kulkami, R. N., et al., *Tissue-specific knockout of the insulin receptor in pancreatic beta cells creates an insulin secretory defect similar to that in type 2 diabetes.* Cell, 1999. 96(3): p. 329-39.
49. Xuan, S., et al., *Defective insulin secretion in pancreatic beta cells lacking type 1 IGF receptor.* J Clin Invest, 2002. 110(7): p. 1011-9.
50. Leibiger, I. B., B. Leibiger, and P. O. Berggren, *Insulin signaling in the pancreatic beta-cell.* Annu Rev Nutr, 2008. 28: p. 233-51.
51. Schlecker, C., et al., *Neuronal calcium sensor-1 enhancement of InsP3 receptor activity is inhibited by therapeutic levels of lithium.* J Clin Invest, 2006. 116(6): p. 1668-74.
52. Nguyen, L. D., et al., *Characterization of NCS1-InsP3R1 interaction and its functional significance.* J Biol Chem, 2019.
53. Osman, A. A., et al., *Wolframin expression induces novel ion channel activity in endoplasmic reticulum membranes and increases intracellular calcium.* J Biol Chem. 2003. 278(52): p. 52755-62.
54. Yuan, T., et al., *mTORC2 Signaling: A Path for Pancreatic beta Cell's Growth and Function.* J Mol Biol, 2018. 430(7): p. 904-918.
55. Bernal-Mizrachi, E., et al., *Defective insulin secretion and increased susceptibility to experimental diabetes are induced by reduced Akt activity in pancreatic islet beta cells.* J Clin Invest, 2004. 114(7): p. 928-36.
56. Hemmings, B. A. and D. F. Restuccia, *PI3K-PKB Akt pathway.* Cold Spring Harb Perspect Biol, 2012. 4(9): p. a011189.
57. Tuttle, R. L., et al., *Regulation of pancreatic beta-cell growth and survival by the serine/threonine protein kinase Akt1/PKBalpha.* Nat Med. 2001. 7(10): p. 1133-7.
58. Conus, N. M., B. A. Hemmings, and R. B. Pearson, *Differential regulation by calcium reveals distinct signaling requirements for the activation of Akt and p70S6k.* J Biol Chem, 1998. 273(8): p. 4776-82.
59. Kang, J. K., et al., *Increased intracellular Ca(2+) concentrations prevent membrane localization of PH domains through the formation of Ca(2+)-phosphoinositides.* Proc Natl Acad Sci USA. 2017. 114(45): p. 11926-11931.
60. Kowluru, A. and A. Matti, *Hyperactivation of protein phosphatase 2A in models of glucolipotoxicity and diabetes: potential mechanisms and functional consequences.* Biochem Pharmacol, 2012. 84(5): p. 591-7.
61. Ruvolo, P. P., *The broken "Off" switch in cancer signaling: PP2A as a regulator of tumorigenesis, drug resistance, and immune surveillance.* BBA Clin, 2016. 6: p. 87-99.
62. Huang, X., et al., *The PI3K/AKT pathway in obesity and type 2 diabetes.* Int J Biol Sci, 2018. 14(11): p. 1483-1496.
63. Ratai, O., et al., *NCS-1 Deficiency Is Associated With Obesity and Diabetes Type 2 in Mice.* Front Mol Neurosci, 2019. 12: p. 78.
64. Goll, D. E., et al., *The calpain system.* Physiol Rev, 2003. 83(3): p. 731-801.
65. Li, Y., et al., *Calpain activation contributes to hyperglycaemia-induced apoptosis in cardiomyocytes.* Cardiovasc Res, 2009. 84(1): p. 100-10.
66. Gurlo, T., et al., *beta Cell-specific increased expression of calpastatin prevents diabetes induced by islet amyloid polypeptide toxicity.* JCI Insight, 2016. 1(18): p. e89590.
67. Jhala, U. S., et al., *cAMP promotes pancreatic beta-cell survival via CREB-mediated induction of IRS2.* Genes Dev, 2003. 17(13): p. 1575-80.
68. Landa, L. R., Jr., et al., *Interplay of Ca2+ and cAMP signaling in the insulin-secreting MIN6 beta-cell line.* J Biol Chem, 2005. 280(35): p. 31294-302.
69. Yan, K., et al., *The cyclic AMP signaling pathway: Exploring targets for successful drug discovery (Review).* Mol Med Rep, 2016. 13(5): p. 3715-23.
70. Ledeboer, A., et al., *The glial modulatory drug AV411 attenuates mechanical allodynia in rat models of neuropathic pain.* Neuron Glia Biol. 2006. 2(4): p. 279-91.
71. Hama, A. T., et al., *The antinociceptive effect of the asthma drug ibudilast in rat models of peripheral and central neuropathic pain.* J Neurotrauma, 2012. 29(3): p. 600-10.
72. Mo, M., et al., *Prevention of paclitaxel-induced peripheral neuropathy by lithium pretreatment.* FASEB J, 2012. 26(11): p. 4696-709.
73. Fox, R. J., et al., *Phase 2 Trial of Ibudilast in Progressive Multiple Sclerosis.* N Engl J Med, 2018. 379(9): p. 846-855.
74. U. S. National Library of Medicine. *Evaluation of MN-166 (Ibudilast) for 12 Months Followed by an Open-label Extension for 6 Months in Patients With ALS.* 2019 [cited 2020 Apr. 6].
75. Levy, J., J. R. Gavin, 3rd, and J. R. Sowers, *Diabetes mellitus: a disease of abnormal cellular calcium metabolism?* Am J Med, 1994. %(3): p. 260-73.
76. Mattson, M. P., *Calcium and neurodegeneration.* Aging Cell, 2007. 6(3): p. 337-50.
77. Pcbitskaya, E., E. Popugaeva, and I. Bezprozvanny, *Calcium signaling and molecular mechanisms underlying neurodegenerative diseases.* Cell Calcium, 2018. 70: p. 87-94.
78. Pomytkin, I., et al., *Insulin receptor in the brain: Mechanisms of activation and the role in the CNS pathology and treatment.* CNS Neurosci Ther, 2018. 24(9): p. 763-774.
79. Jesinkey, S. R., et al., *Mitochondrial GYP Links Nutrient Sensing to beta Cell Health. Mitochondrial Morphology, and Insulin Secretion Independent of OxPhos.* Cell Rep, 2019. 28(3): p. 759-772 e10.

The invention claimed is:

1. A method of treating Wolfram syndrome or WFS1 disorder in a patient in need comprising administering to said patient an effective amount of a compound according to the chemical structure:

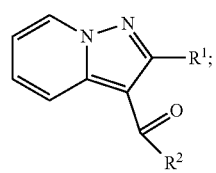

Wherein $R^1$ is a $C_1$-$C_6$ alkyl;

$R^2$ is a $C_1$-$C_6$ alkyl or a

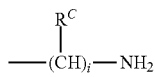

group, where $R^C$ is independently H or $C_1$-$C_3$ alkyl; and i is 0, 1, 2 or 3, or a pharmaceutically acceptable salt, enantiomer or diastereomer thereof.

2. The method according to claim 1 wherein $R^1$ is isopropyl and $R^2$ is isopropyl, or a pharmaceutically acceptable salt thereof.

3. The method according to claim 1 wherein $R^1$ is isopropyl and $R_2$ is isopropyl.

4. The method according to claim 1 wherein $R^1$ is isopropyl and $R^2$ is a —C(H)(CH$_3$)NH$_2$ group.

5. The method according to claim 1 wherein said treatment of Wolfram syndrome or WFS1 disorder results in the delay, inhibition, amelioration of at least one symptom of Wolfram syndrome or WFS1 disorder.

6. The method according to claim 5 wherein said symptom of Wolfram syndrome is premature death, diabetes mellitus, diabetes insipidus, visual impairment, optical atrophy, color blindness, slow reacting iris, high frequency hearing loss, tonal deafness, emotional agitation, tremors, seizures, peripheral neuropathy, autonomic dysfunction, ataxia, ptosis, nystagmus, endocrinopathies, brainstem atrophy, gastrointestinal disorders, dysmotility diarrhea, constipation, urinary tract atony, urinary incontinence, recurrent urinary infections, hidronephrosis, primary gonadal atrophy, menstrual irregularities, delayed menarche or a psychiatric disorder.

7. The method according to claim 6 wherein said symptom is diabetes mellitus or diabetes insipidus.

8. The method according to claim 6 wherein said psychiatric disorder is depression, severe depression, bipolar disorder, impulsive verbal aggression or impulsive physical aggression.

9. A method of treating a psychiatric disorder associated with heterozygous wolfram in in a patient in need comprising administering to said patient a composition comprising an effective amount of ibudilast or AV1013.

10. The method according to claim 9 wherein said psychiatric disorder is depression, severe depression, bipolar disorder, impulsive verbal aggression or impulsive physical aggression.

11. The method according to claim 9 wherein said composition comprises ibudilast.

12. The method according to claim 9 wherein said composition comprises AV1013 or a pharmaceutically acceptable salt or enantiomer thereof.

13. The method according to claim 9 wherein said psychiatric disorder is depression, severe depression or bipolar disorder.

14. The method according to claim 13 wherein said psychiatric disorder is depression or severe depression.

15. The method according to claim 13 wherein said psychiatric disorder is bipolar disorder.

16. The method according to claim 13 wherein said psychiatric disorder is impulsive verbal aggression or impulsive physical aggression.

17. A method of treating Wolfram syndrome in a patient in need comprising administering to said patient an effective amount of ibudilast.

18. The method according to claim 17 wherein said treatment of Wolfram syndrome results in the delay, inhibition, amelioration of at least one symptom of Wolfram syndrome.

19. The method according to claim 18 wherein said symptom of Wolfram syndrome is premature death, diabetes mellitus, diabetes insipidus, visual impairment, optical atrophy, color blindness, slow reacting iris, high frequency hearing loss, tonal deafness, emotional agitation, tremors, seizures, peripheral neuropathy, autonomic dysfunction, ataxia, ptosis, nystagmus, endocrinopathies, brainstem atrophy, gastrointestinal disorders, dysmotility, diarrhea, constipation, urinary tract atony, urinary incontinence, recurrent urinary infections, hydronephrosis, primary gonadal atrophy, menstrual irregularities, delayed menarche or a psychiatric disorder.

20. The method according to claim 19 wherein said symptom is diabetes mellitus or diabetes insipidus.

21. The method according to claim 20 wherein said symptom is diabetes mellitus.

22. The method according to claim 19 wherein said psychiatric disorder is depression, severe depression, bipolar disorder, impulsive verbal aggression or impulsive physical aggression.

23. A method of treating a symptom associated with WFS1 disorder in a patient in need comprising administering to said patient an effective amount of a compound according to the chemical structure:

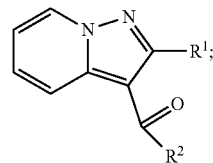

Where $R^1$ is a $C_1$-$C_6$ alkyl group;
$R^2$ is $C_1$-$C_6$ alkyl or a

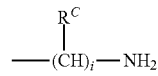

group, where each $R^C$ is independently H or $C_1$-$C_3$ alkyl; and i is 0, 1, 2 or 3, or a pharmaceutically acceptable salt, enantiomer or diastereomer thereof.

24. The method according to claim 23 wherein said compound is ibudilast or AV1013.

25. The method according to claim 23 wherein said compound is ibudilast.

26. The method according to claim 23 wherein said compound is AV1013 or a pharmaceutically acceptable salt or enantiomer thereof.

27. The method according to claim 23 wherein said symptom of WFS1 disorder is sensorineural hearing loss, diabetes mellitus, a psychiatric disorder, and variable optic atrophy.

28. The method according to claim 27 wherein said psychiatric disorder is depression, severe depression, bipolar disorder, impulsive verbal aggression or impulsive physical aggression.

* * * * *